United States Patent [19]
Horvitz et al.

[11] Patent Number: 5,962,301
[45] Date of Patent: Oct. 5, 1999

[54] RELATEDNESS OF HUMAN INTERLEUKIN-1β CONVERTASE GENE TO A C. ELEGANS CELL DEATH GENE, INHIBITORY PORTIONS OF THESE GENES AND USES THEREFOR

[75] Inventors: H. Robert Horvitz, Auburndale; Junying Yuan, Newton; Shai Shaham, Cambridge, all of Mass.

[73] Assignee: Massachusetts Institute of Technology, Cambridge, Mass.

[21] Appl. No.: 08/394,189

[22] Filed: Feb. 24, 1995

Related U.S. Application Data

[60] Continuation-in-part of application No. 08/282,211, Jul. 11, 1994, which is a division of application No. 07/984,182, Nov. 20, 1992, abandoned, which is a continuation-in-part of application No. 07/897,788, Jun. 12, 1992, abandoned.

[51] Int. Cl.$^6$ .............................. C12N 9/64; C12N 9/50
[52] U.S. Cl. .......................................... 435/226; 435/219
[58] Field of Search ................................. 435/226, 219, 435/212; 530/350, 324

[56] References Cited

U.S. PATENT DOCUMENTS

| 5,278,061 | 1/1994 | Bull et al. ................................ 435/212 |
| 5,416,013 | 5/1995 | Black et al. ............................. 435/226 |
| 5,492,824 | 2/1996 | Talanian et al. ........................ 435/226 |

FOREIGN PATENT DOCUMENTS

| 053 3350 | 3/1993 | European Pat. Off. . |
| WO A 91 5577 | 10/1991 | WIPO . |
| WO 91/19007 | 12/1991 | WIPO . |
| WO A 92 07071 | 4/1992 | WIPO . |

OTHER PUBLICATIONS

Jacobson et al., "Breaking the Ice" Current Biology 4(4):337, 1994.
Miller et al., "The IL–1β Converting Enzyme as a Therapeutic Target" Ann. NY Acad. Sci.696:133, 1993.
Miura et al., "Induction of Apoptosis in Fibroblasts by IL–1β–Converting Enzyme, a Mammalian Homolog of the C. elegans Cell Death Gene ced–3" Cell 75:653, 1993.
Wang et al., "Ich–1, and Ice/ced–3–Related Gene, Encodes Both Positive and Negative Regulators of Programmed Cell Death" Cell 78:739, 1994.
Cerretti et al., "Molecular Cloning of the Interleukin–1β Converting Enzyme", Science 256:97–100 (1992).
Thornberry et al., "A Novel Heterodimeric Cysteine Protease is required for Interleukin–1β Processing in Monocytes", Nature 356:768–774 (1992).
Sleath et al., "Substrate Specificity of the Protease that Processes Human Interleukin–1β", J. Biol. Chem. 265(24):14526–14528 (1990).
Kronheim et al., "Purification of Interleukin–1β Converting Enzyme, the Protease that Cleaves the Interleukin–1β Precursor", Archives of Biochemistry and Biophysics 296:698–703 (1992).

Nett et al., "Molecular Cloning of the Murine IL–1β Converting Enzyme cDNA", J. Immun. 149:3254–3259 (1992).
Molineaux et al., "Interleukin 1β (IL–1β) processing in murine macrophages requires a structurally conserved homologue of human IL–1β", Proc. Natl. Acad. Sci. USA 90:1809–1813 (1993).
Ray et al., "Viral Inhibition of Inflammation: Cowpox Virus Encodes an Inhibitor of the Interleukin–1β Converting Enzyme", Cell 69:597–604 (1992).
Pickup et al., "Hemmorrhage in Lesions Caused by Cowpox Virus is Induced by a Viral Protein that is Related to Plasma Protein Inhibitors of Serine Proteases", Proc. Natl. Acad. Sci. USA 83:7698–7702 (1986).
Kumar et al., "Identification of a Set of Genes with Developmentally Down–Regulated Expression in the Mouse Brain", Biochem. Biophys. Res. Com. 185(3):1155–1161 (1992).
Horvitz and Chalfie, "Implications of Nematode Neuronal Cell Death for Human Neurological Disorders" in Neurodegenerative Disorders: Mech. and Prosp. for Therapy, Price et al. (ed.), J. Wiley & Sons, (1991) pp. 5–19.
Brenneman et al., "Cytokine Regulation of Neuronal Survival", J. Neurochem. 58(2):454–460 (1992).
Hogquist et al., "Interleukin 1 is Processes and Released During Apoptosis", Proc. Natl. Acad. Sci. USA 88:8485–8489 (1991).
Colotta et al., "Modulation of Granulocyte Survival and Programmed Cell Death by Cytokines and Bacterial Products", Blood 80(8):2012–2020 (1992).
Mangan et al., "Lipopolysaccharide, Tumor Necrosis Factor–α and IL–1β Prevent Programmed Cell Death (Apoptosis) in Stimulated Human Monocytes", J. Immun. 148(6):1812–1816 (1992).

(List continued on next page.)

*Primary Examiner*—Charles L. Patterson, Jr.
*Assistant Examiner*—Gabriele E. Bugalsky
*Attorney, Agent, or Firm*—Clark & Elbing LLP

[57] ABSTRACT

Described herein is the discovery that human interleukin-1β convertase (ICE) is structurally similar to the protein encoded by the C. elegans cell death gene, ced-3. Comparative and mutational analyses of the two proteins, together with previous observations, suggest that the Ced-3 protein may be a cysteine protease like ICE and that ICE may be a human equivalent of the nematode cell death gene. Another mammalian protein, the murine NEDD-2 protein, was also found to be similar to Ced-3. The NEDD-2 gene is implicated in the development of the murine central nervous system. On the basis of these findings, novel drugs for enhancing or inhibiting the activity of ICE, ced-3, or related genes are provided. Such drugs may be useful for treating inflammatory diseases and/or diseases characterized by cell deaths, as well as cancers, autoimmune disorders, infections, and hair growth and hair loss. Furthermore, such drugs may be useful for controlling pests, parasites and genetically engineered organisms. Furthermore, novel inhibitors of the activity of ced-3, ICE and related genes are described which comprise portions of the genes or their encoded products.

2 Claims, 24 Drawing Sheets

OTHER PUBLICATIONS

Mangan and Wahl, "Differential Regulation of Human Monocyte Programmed Cell Death (Apoptosis) by Chemotactic Factors and Pro–Inflammatory Cytokines", J. Immun. 147(10):3408–3412 (1991).

Mangan et al., "IL–4 Enhances Programmed Cell Death (Apoptosis) in Stimulated Human Monocytes", J. Immun. 148(6):1812–1816 (1992).

McConkey et al., "Interleukin 1 Inhibits T Cell Receptor–Mediated Apoptosis in Immature Thymocytes", J. Biol. Chem. 265(6):3009–3011 (1990).

McConkey et al., "Agents that Elevate cAMP Stimulate DNA Fragmentation in Thymocytes", J. Immun. 145(4):1227–1230 (1990).

Lotem and Sachs, "Hematopoietic Cytokines Inhibit Apoptosis Induced by Transforming Growth Factor β1 and Cancer Chemotherapy Compounds in Myeloid Leukemic Cells", Blood 80(7):1750–1757 (1992).

Estrov et al., "Suppression of Chronic Myelogenous Leukemia Colony Growth by Interleukin–1 (IL–1) Receptor Antagonist and Soluble IL–1 Receptors: A Novel Application . . . ", Blood 78(6):1476–1484 (1991).

Rambaldi et al., "Modulation of Cell Proliferation and Cytokine Production in Acute Myeloblastic Leukemia by Interleukin–1 Receptor Antagonist and Lack of its Expression . . . ", Blood 78(12):3248–3253 (1991).

Fuhlbrigge et al., "Molecular Biology and Genetics of Interleukin–1", Year Immunology 5:21–37 (1989).

Black et al., "Activation of Interleukin–1β by a co–induced Protease", FEBS Letters 247(2):386–390 (1989).

Black et al., "A Pre–aspartate–specific Protease from Human Leukocytes that Cleaves Pro–interleukin–1β", J. Biol. Chem. 264(10):5323–5326 (1989).

Kostura et al., "Identification of a monocyte specific pre––interleukin 1β convertase activity", Proc. Natl. Acad. Sci. USA 86:5227–5231 (1989).

Ledoux et al., "Isolation of nematode homologs of the *C. elegans* cell death gene ced–3'" Neurobiology of Aging 13:S47 (1992).

(Merck & Co. Inc.) Database WPI Week 9318 AN 93–144400 Feb. 1993 Abstract, Derwent Publications Ltd. London, GB.

Yuan, J. Dissertation Abstracts International, vol. 50/10–B, 1989.

ced-3 Genomic Sequence

```
      AGATCTGAAATAAGGTGATAAATTAATAAATTAAGTGTATTTCTGAGGAAATTTGACTGT
   1  ---------+---------+---------+---------+---------+---------+   60
      TTTAGCACAATTAATCTTGTTTCAGAAAAAAGTCCAGTTTTCTAGATTTTTCCGTCTTA
  61  ---------+---------+---------+---------+---------+---------+  120
      TTGTCGAATTAATATCCCTATTATCACTTTTTCATGCTCATCCTCGAGCGGCACGTCCTC
 121  ---------+---------+---------+---------+---------+---------+  180
      AAAGAATTGTGAGAGCAAACGCGCTCCCATTGACCTCCACACTCAGCCGCCAAAACAAAC
 181  ---------+---------+---------+---------+---------+---------+  240
      GTTCGAACATTCGTGTGTTGTGCTCCTTTTCCGTTATCTTGCAGTCATCTTTTGTCGTT
 241  ---------+---------+---------+---------+---------+---------+  300
      TTTTCTTTGTTCTTTTTGTTGAACGTGTTGCTAAGCAATTATTACATCAATTGAAGAAAA
 301  ---------+---------+---------+---------+---------+---------+  360
      GGCTCGCCGATTTATTGTTGCCAGAAAGATTCTGAGATTCTCGAAGTCGATTTTATAATA
 361  ---------+---------+---------+---------+---------+---------+  420
      TTTAACCTTGGTTTTTGCATTGTTTCGTTTAAAAAAACCACTGTTTATGTGAAAAACGA
 421  ---------+---------+---------+---------+---------+---------+  480
      TAGTTTACTAATAAAACTACTTTTAAACCTTTACCTTTACCTCACCGCTCCGTGTTCATG
 481  ---------+---------+---------+---------+---------+---------+  540
      GCTCATAGATTTTCGATACTCAAATCCAAAAATAAATTTACGAGGGCAATTAATGTGAAA
 541  ---------+---------+---------+---------+---------+---------+  600
      CAAAAACAATCCTAAGATTTCCACATGTTTGACCTCTCCGGCACCTTCTTCCTTAGCCCC
 601  ---------+---------+---------+---------+---------+---------+  660
      ACCACTCCATCACCTCTTTGGCGGTGTTCTTCGAAACCCACTTAGGAAAGCAGTGTGTAT
 661  ---------+---------+---------+---------+---------+---------+  720
      CTCATTTGGTATGCTCTTTTCGATTTTATAGCTCTTTGTCGCAATTTCAATGCTTTAAAC
 721  ---------+---------+---------+---------+---------+---------+  760
      AATCCAAATCGCATTATATTTGTGCATGGAGGCAAATGACGGGGTTGGAATCTTAGATGA
 781  ---------+---------+---------+---------+---------+---------+  840
      GATCAGGAGCTTTCAGGGTAAACGCCCGGTTCATTTGTACCACATTTCATCATTTTCCT
 841  ---------+---------+---------+---------+---------+---------+  900
      GTCGTCCTTGGTATCCTCAACTTGTCCCGGTTTTGTTTTCGGTACACTCTTCCGTGATGC
 901  ---------+---------+---------+---------+---------+---------+  960
      CACCTGTCTCCGTCTCAATTATCGTTTAGAAATGTGAACTGTCCAGATGGGTGACTCATA
 961  ---------+---------+---------+---------+---------+---------+ 1020
      TTGCTGCTGCTACAATCCACTTTCTTTTCTCATCGGCAGTCTTACGAGCCCATCATAAAC
1021  ---------+---------+---------+---------+---------+---------+ 1080
      TTTTTTTTCCGCGAAATTTGCAATAAACCGGCCAAAAACTTTCTCCAAATTGTTACGCAA
1081  ---------+---------+---------+---------+---------+---------+ 1140
      TATATACAATCCATAAGAATATCTTCTCAATGTTTATGATTTCTTCGCAGCACTTTCTCT
1141  ---------+---------+---------+---------+---------+---------+ 1200
      TCGTGTGCTAACATCTTATTTTTATAATATTTCCGCTAAAATTCCGATTTTTGAGTATTA
1201  ---------+---------+---------+---------+---------+---------+ 1260
      ATTTATCGTAAAATTATCATAATAGCACCGAAAACTACTAAAAATGGTAAAAGCTCCTTT
1261  ---------+---------+---------+---------+---------+---------+ 1320
                                                        Repeat 1
                                                  ========================
      TAAATCGGCTCGACATTATCGTATTAAGGAATCACAAAATTCTGAGAATGCGTACTGCGC
1321  ---------+---------+---------+---------+---------+---------+ 1380
      AACATATTTGACGGCAAAATATCTCGTAGCGAAAACTACAGTAATTCTTTAAATGACTAC
1381  ---------+---------+---------+---------+---------+---------+ 1440
```

Fig. 3

```
                                                          Repeat 1
     ===============================>        <==========
     TGTAGCGCTTGTGTCGATTTACGGGCTCAATTTTTGAAAATAATTTTTTTTTTCGAATTT
1441 ---------+---------+---------+---------+---------+---------+ 1500
     ============================================================
     TGATAACCCGTAAATCGTCACAACGCTACAGTAGTCATTTARAGGATTACTGTAGTTCTA
1501 ---------+---------+---------+---------+---------+---------+ 1560

==========================================================
     GCTACGAGATATTTTGCGCGCCAAATATGACTGTAATACGCATTCTCTGAATTTTGTGTT
1561 ---------+---------+---------+---------+---------+---------+ 1620
     TCCGTAATAATTTCACAAGATTTTGGCATTCCACTTTAAAGGCGCACAGGATTTATTCCA
1621 ---------+---------+---------+---------+---------+---------+ 1680
     ATGGGTCTCGGCACGCAAAAAGTTTGATAGACTTTTAAATTCTCCTTGCATTTTTAATTC
1681 ---------+---------+---------+---------+---------+---------+ 1740
     AATTACTAAAATTTTCGTGAATTTTTCTGTTAAAATTTTTAAAATCAGTTTTCTAATATT
1741 ---------+---------+---------+---------+---------+---------+ 1800
     TTCCAGGCTGACAAACAGAAACAAAAACACAACAAACATTTTAAAAATCAGTTTTCAAAT
1801 ---------+---------+---------+---------+---------+---------+ 1860
     TAAAAATAACGATTTCTCATTGAAAATTGTGTTTTATGTTTGCGAAAATAAAAGAGAACT
1861 ---------+---------+---------+---------+---------+---------+ 1920
     GATTCAAAACAATTTTAACAAAAAAAAAACCCCAAAATTCGCCAGAAATCAAGATAAAAAA
1921 ---------+---------+---------+---------+---------+---------+ 1980
     TTCAAGAGGGTCAAAATTTTCCGATTTTACTGACTTTCACCTTTTTTTTCGTAGTTCAGT
1981 ---------+---------+---------+---------+---------+---------+ 2040
     GCAGTTGTTGGAGTTTTTGACGAAAACTAGGAAAAAAATCGATAAAAATTACTCAAATCG
2041 ---------+---------+---------+---------+---------+---------+ 2100
     AGCTGAATTTTGAGGACAATGTTTAAAAAAAAACACTATTTTTCCAATAATTTCACTCAT
2101 ---------+---------+---------+---------+---------+---------+ 2160

-------
     TTTCAGACTAAATCGAAAATCAAATCGTACTCTGACTACGGGTCAGTAGAGAGGTCAACC

2161 ---------+---------+---------+---------+---------+---------+ 2220

ATCAGCCGAAGATGATGCGTCAAGATAGAAGGAGCTTGCTAGAGAGGAACATTATGATGT
2221 ---------+---------+---------+---------+---------+---------+ 2280
             M   M   R   Q   D   R   R   S   L   L   E   R   N   I   M   M   F
             1                                   10
                          T(n1040)
                             |
     TCTCTAGTCATCTAAAAGTCGATGAAATTCTCGAAGTTCTCATCGCAAAACAAGTGTTGA
2281 ---------+---------+---------+---------+---------+---------+ 2340
         S   S   H   L   K   V   D   E   I   L   E   V   L   I   A   K   Q   V   L   N
                 20                                  30
                                 |intron 1
     ATAGTGATAATGGAGATATGATTAATGTGAGTTTTTAATCGAATAATAATTTTAAAAAAA
2341 ---------+---------+---------+---------+---------+---------+ 2400
         S   D   N   G   D   M   I   N
                     40
                                           |
     AATTGATAATATAAAGAATATTTTTGCAGTCATGTGGAACGGTTCGCGAGAAGAGACGGG
2401 ---------+---------+---------+---------+---------+---------+ 2460
                                     S   C   G   T   V   R   E   K   R   R   E
                                                         50
```

Fig. 3 (cont.)

```
                            A(n718)
                              |
       AGATCGTGAAAGCAGTGCAACGACGGGGAGATGTGGCGTTCGACGCGTTTTATGATGCTC
2461   ---------+---------+---------+---------+---------+---------+ 2520
         I  V  K  A  V  Q  R  R  G  D  V  A  F  D  A  F  Y  D  A  L
                  60                         70
                                                             |intron 2
       TTCGCTCTACGGGACACGAAGGACTTGCTGAAGTTCTTGAACCTCTCGCCAGATCGTAGG
2521   ---------+---------+---------+---------+---------+---------+ 2580
         R  S  T  G  H  E  G  L  A  E  V  L  E  P  L  A  R  S
                  80                         90

TTTTTAAAGTTCGGCGCAAAAGCAAGGGTCTCACGGAAAAAAGAGGCGGATCGTAATTTT
2581   ---------+---------+---------+---------+---------+---------+ 2640
       GCAACCCACCGGCACGGTTTTTTCCTCCGAAAATCGGAATTATGCACTTTCCCAAATAT
2641   ---------+---------+---------+---------+---------+---------+ 2700
       TTGAAGTGAAATATATTTTATTTACTGAAAGCTCGAGTGATTATTTATTTTTTAACACTA
2701   ---------+---------+---------+---------+---------+---------+ 2760
       ATTTTCGTGGCGCAAAAGGCCATTTTGTAGATTTGCCGAAAATACTTGTCACACACAC
2761   ---------+---------+---------+---------+---------+---------+ 2820
                                         |
       ACACACATCTCCTTCAAATATCCCTTTTTCCAGTGTTGACTCGAATGCTGTCGAATTCGA
2821   ---------+---------+---------+---------+---------+---------+ 2880
                                    V  D  S  N  A  V  E  F  E
                                                  100

GTGTCCAATGTCACCGGCAAGCCATCGTCGGAGCCGCGCATTGAGCCCCGCCGGCTACAC
2881   ---------+---------+---------+---------+---------+---------+ 2940
         C  P  M  S  P  A  S  H  R  R  S  R  A  L  S  P  A  G  Y  T
                 110                         120

TTCACCGACCCGAGTTCACCGTGACAGCGTCTCTTCAGTGTCATCATTCACTTCTTATCA
2941   ---------+---------+---------+---------+---------+---------+ 3000
         S  P  T  R  V  H  R  D  S  V  S  S  V  S  S  F  T  S  Y  Q
                 130                         140

GGATATCTACTCAAGAGCAAGATCTCGTTCTCGATCGCGTGCACTTCATTCATCGGATCG
3001   ---------+---------+---------+---------+---------+---------+ 3060
         D  I  Y  S  R  A  R  S  R  S  R  S  R  A  L  H  S  S  D  R
                 150                         160
                                                          | intron 3
       ACACAATTATTCATCTCCTCCAGTCAACGCATTTCCCAGCCAACCTTGTATGTTGATGCG
3061   ---------+---------+---------+---------+---------+---------+ 3120
         H  N  Y  S  S  P  P  V  N  A  F  P  S  Q  P  S
                         170

Repeat 1
              ======================================================
       AACACTAAATTCTGAGAATGCGCATTACTCAACATATTTGACGCGCAAATATCTCGTAGC
3121   ---------+---------+---------+---------+---------+---------+ 3180

======================================================
       GAAAATACAGTAACCCTTTAAATGACTATTGTAGTGTCGATTTACGGGCTCGATTTTCG
3181   ---------+---------+---------+---------+---------+---------+ 3240
```

Fig. 3 (cont.)

```
            ==>
            AAACGAATATATGCTCGAATTGTGACAACGAATTTTAATTTGTCATTTTTGTGTTTTCTT
     3241   ---------+---------+---------+---------+---------+---------+   3300

Repeat 1
                           <==============================
            TTGATATTTTTGATCAATTAATAAATTATTTCCGTAAACAGACACCAGCGCTACAGTACT
     3301   ---------+---------+---------+---------+---------+---------+   3360

====================================
            CTTTTAAAGAGTTACAGTAGTTTTCGCTTCAAGATATTTTGAAAAGAATTTTAAACATTT
     3361   ---------+---------+---------+---------+---------+---------+   3420

TGAAAAAAAATCATCTAACATGTGCCAAAACGCTTTTTTCAAGTTTCGCAGATTTTTTGA
     3421   ---------+---------+---------+---------+---------+---------+   3480

Repeat 2
            ============================================================
            TTTTTTTCATTCAAGATATGCTTATTAACACATATAATTATCATTAATGTGAATTTCTTG
     3481   ---------+---------+---------+---------+---------+---------+   3540

============================================================
            TAGAAATTTTGGGCTTTTCGTTCTAGTATGCTCTACTTTTGAAATTGCTCAACGAAAAAA
     3541   ---------+---------+---------+---------+---------+---------+   3600

============================================================
            TCATGTGGTTTGTTCATATGAATGACGAAAAATAGCAATTTTTTATATATTTTCCCCTAT
     3601   ---------+---------+---------+---------+---------+---------+   3660

============================================================
            TCATGTTGTGCAGAAAAATAGTAAAAAAGCGCATGCATTTTTCGACATTTTTTACATCGA
     3661   ---------+---------+---------+---------+---------+---------+   3720

======================================>
            ACGACAGCTCACTTCACATGCTGAAGACGAGAGACGCGGAGAAATACCACACATCTTTCT
     3721   ---------+---------+---------+---------+---------+---------+   3780

Repeat 2
            <===========================================================
            GCGTCTCTCGTCTTCAGCATGTGAAATGGGATCTCGGTCGATGTAAAAAAATGTCGAATA
     3781   ---------+---------+---------+---------+---------+---------+   3840

============================================================
            ATGTAAAAAATGCATGCGTTTTTTTACACTTTTCTGCACAAATGAATAGGGGGAAAATGT
     3841   ---------+---------+---------+---------+---------+---------+   3900

============================================================
            ATTAAAATACATTTTTTGTATTTTTCAACATCACATGATTAACCCCATTATTTTTTCGTT
     3901   ---------+---------+---------+---------+---------+---------+   3960

============================================================
            GAGCAACTTAAAAAGTAGAGAATATTAGAGCGAAAACCAAAATTTCTTCAAGATATTACC
     3961   ---------+---------+---------+---------+---------+---------+   4020

===========================================================
            TTTATTGATAATTATAGATGTTAATAAGCATATCTTGAATGAAAGTCAGCAAAAATATGT
     4021   ---------+---------+---------+---------+---------+---------+   4080
```

Fig. 3 (cont.)

```
4081 ---------+---------+---------+---------+---------+---------+ 4140
     TTTTTGCATTTTTCTACATCACATGAATGTAGAAAATTAAAAGGGAAATCAAAATTTCTA
4141 ---------+---------+---------+---------+---------+---------+ 4200
     GAGGATATAATTGAATGAAACATTGCGAAATTAAAATGTGCGAAACGTCAAAAAAGAGGA
4201 ---------+---------+---------+---------+---------+---------+ 4260

|
     AATTTGGGTATCAAAATCGATCCTAAAACCAACACATTTCAGCATCCGCCAACTCTTCAT
4261 ---------+---------+---------+---------+---------+---------+ 4320
                                               S   A   N   S   S   F
                                                          180

TCACCGGATGCTCTTCTCTCGGATACAGTTCAAGTCGTAATCGCTCATTCAGCAAAGCTT
4321 ---------+---------+---------+---------+---------+---------+ 4380
       T   G   C   S   S   L   G   Y   S   S   R   N   R   S   F   S   K   A   S
                       190                             200

CTGGACCAACTCAATACATATTCCATGAAGAGGATATGAACTTTGTCGATGCACCAACCA
4381 ---------+---------+---------+---------+---------+---------+ 4440
         G   P   T   Q   Y   I   F   H   E   E   D   M   N   F   V   D   A   P   T   I
                       210                             220

TAAGCCGTGTTTTCGACGAGAAAACCATGTACAGAAACTTCTCGAGTCCTCGTGGAATGT
4441 ---------+---------+---------+---------+---------+---------+ 4500
         S   R   V   F   D   E   K   T   M   Y   R   N   F   S   S   P   R   G   M   C
                       230                             240

GCCTCATCATAAATAATGAACACTTTGAGCAGATGCCAACACGGAATGGTACCAAGGCCG
4501 ---------+---------+---------+---------+---------+---------+ 4560
       L   I   I   N   N   E   H   F   E   Q   M   P   T   R   N   G   T   K   A   D
                       250                             260

ACAAGGACAATCTTACCAATTTGTTCAGATGCATGGGCTATACGGTTATTTGCAAGGACA
4561 ---------+---------+---------+---------+---------+---------+ 4620
         K   D   N   L   T   N   L   F   R   C   M   G   Y   T   V   I   C   K   D   N
                       270                             280

| intron 4
     ATCTGACGGGAAGGGTACGGCGAAATTATATTACCCAAACGCGAAATTTGCCATTTTGCG
4621 ---------+---------+---------+---------+---------+---------+ 4680
         L   T   G   R Repeat 3
              ==============================>
     CCGAAAATGTGGCGCCCGGTCTCGACACGACAATTTGTGTTAAATGCAAAAATGTATAAT
4681 ---------+---------+---------+---------+---------+---------+ 4740
     TTTGCAAAAAACAAAATTTTGAACTTCCGCGAAAATGATTTACCTAGTTTCGAAATTTTC
4741 ---------+---------+---------+---------+---------+---------+ 4800
     GTTTTTTCCGGCTACATTATGTGTTTTTTCTTAGTTTTTCTATAATATTTGATGTAAAAA
4801 ---------+---------+---------+---------+---------+---------+ 4860
     ACCGTTTGTAAATTTTCAGACAATTTTCCGCATACAAAACTTGATAGCACGAAATCAATT
4861 ---------+---------+---------+---------+---------+---------+ 4920
     TTCTGAATTTTCAAAATTATCCAAAAATGCACAATTTAAAATTTGTGAAAATTGGCAAAC
4921 ---------+---------+---------+---------+---------+---------+ 4980
```

Fig. 3 (cont.)

```
     GGTGTTTCAATATGAAATGTATTTTTAAAAACTTTAAAAACCACTCCGGAAAAGCAATAA
4981 ---------+---------+---------+---------+---------+---------+ 5040
     AAATCAAAACAACGTCACAATTCAAATTCAAAAGTTATTCATCCGATTTGTTTATTTTTG
5041 ---------+---------+---------+---------+---------+---------+ 5100
     CAAAATTTGAAAAAATCATGAAGGATTTAGAAAAGTTTTATAACATTTTTTCTAGATTTT
5101 ---------+---------+---------+---------+---------+---------+ 5160
     TCAAAATTTTTTTTAACAAATCGAGAAAAAGAGAATGAAAAATCGATTTTAAAAATATCC
5161 ---------+---------+---------+---------+---------+---------+ 5220

Repeat 3
         <=========================================================
     ACAGCTTCGAGAGTTTGAAATTACAGTACTCCTTAAAGGCGCACACCCCATTTGCATTGG
5221 ---------+---------+---------+---------+---------+---------+ 5280

============================================================
     ACCAAAAATTTGTCGTGTCGAGACCAGGTACCGTAGTTTTGTCGCAAAAATTGCACCAT
5281 ---------+---------+---------+---------+---------+---------+ 5340
     TGGACAATAAACCTTCCTAATCACCAAAAAGTAAAATTGAAATCTTCGAAAAGCCAAAAA
5341 ---------+---------+---------+---------+---------+---------+ 5400
     ATTCAAAAAAAAAGTCGAATTTCGATTTTTTTTTGGTTTTTTGGTCCCAAAAACCAAAA
5401 ---------+---------+---------+---------+---------+---------+ 5460
     AAATCAATTTTCTGCAAAATACCAAAAAGAAACCCGAAAAAATTTCCCAGCCTTGTTCCT
5461 ---------+---------+---------+---------+---------+---------+ 5520
                                                       |
     AATGTAAACTGATATTTAATTTCCAGGGAATGCTCCTGACAATTCGAGACTTTGCCAAAC
5521 ---------+---------+---------+---------+---------+---------+ 5580
                         G  M  L  L  T  I  R  D  F  A  K  H
                            290                           300

ACGAATCACACGGAGATTCTGCGATACTCGTGATTCTATCACACGGAGAAGAGAATGTGA
5581 ---------+---------+---------+---------+---------+---------+ 5640
      E  S  H  G  D  S  A  I  L  V  I  L  S  H  G  E  E  N  V  I
                              310                           320
     TTATTGGAGTTGATGATATACCGATTAGTACACACGAGATATATGATCTTCTCAACGCGG
5641 ---------+---------+---------+---------+---------+---------+ 5700
      I  G  V  D  D  I  P  I  S  T  H  E  I  Y  D  L  L  N  A  A
                              330                           340
                                                          A(n2433)
                                                          |  | intron 5
     CAAATGCTCCCCGTCTGGCGAATAAGCCGAAAATCGTTTTTGTGCAGGCTTGTCGAGGCG
5701 ---------+---------+---------+---------+---------+---------+ 5760
      N  A  P  R  L  A  N  K  P  K  I  V  F  V  Q  A  C  R  G  E
                              350                           360
                                                     |
     GTTCGTTTTTTATTTTAATTTTAATATAAATATTTTAAATAAATTCATTTTCAGAACGTC
5761 ---------+---------+---------+---------+---------+---------+ 5820
                                                          R  R
     GTGACAATGGATTCCCAGTCTTGGATTCTGTCGACGGAGTTCCTGCATTTCTTCGTCGTG
5821 ---------+---------+---------+---------+---------+---------+ 5880
      D  N  G  F  P  V  L  D  S  V  D  G  V  P  A  F  L  R  R  G
                              370                           380
```

Fig. 3 (cont.)

```
                                                                    T(n1165)
                                                                       |
       GATGGGACAATCGAGACGGGCCATTGTTCAATTTTCTTGGATGTGTGCGGCCGCAAGTTC
5881   ---------+---------+---------+---------+---------+---------+ 5940
         W  D  N  R  D  G  P  L  F  N  F  L  G  C  V  R  P  Q  V  Q
                         390                              400

| intron 6
       AGGTTGCAATTTAATTTCTTGAATGAGAATATTCCTTCAAAAAATCTAAAATAGATTTTT
5941   ---------+---------+---------+---------+---------+---------+ 6000
       ATTCCAGAAAGTCCCGATCGAAAAATTGCGATATAATTACGAAATTTGTGATAAAATGAC
6001   ---------+---------+---------+---------+---------+---------+ 6060

Repeat 4
       ============================================================
       AAACCAATCAGCATCGTCGATCTCCGCCCACTTCATCGGATTGGTTTGAAAGTGGGCGGA
6061   ---------+---------+---------+---------+---------+---------+ 6120

================>
       GTGAATTGCTGATTGGTCGCAGTTTTCAGTTTAGAGGGAATTTAAAAATCGCCTTTTCGA
6121   ---------+---------+---------+---------+---------+---------+ 6180
       AAATTAAAAATTGATTTTTTCAATTTTTTCGAAAAATATTCCGATTATTTTATATTCTTT
6181   ---------+---------+---------+---------+---------+---------+ 6240

A(n717)
                                                                 |
       GGAGCGAAAGCCCCGTCCTGTAAACATTTTTAAATGATAATTAATAAATTTTTGCAGCAA
6241   ---------+---------+---------+---------+---------+---------+ 6300
                                                                 Q

T(n1949)
                           |
       GTGTGGAGAAAGAAGCCGAGCCAAGCTGACATTCTGATTCGATACGCAACGACAGCTCAA
6301   ---------+---------+---------+---------+---------+---------+ 6360
         V  W  R  K  K  P  S  Q  A  D  I  L  I  R  Y  A  T  T  A  Q
                         410                              420

A(n1286)
                    |
       TATGTTTCGTGGAGAAACAGTGCTCGTGGATCATGGTTCATTCAAGCCGTCTGTGAAGTG
6361   ---------+---------+---------+---------+---------+---------+ 6420
         Y  V  S  W  R  N  S  A  R  G  S  W  F  I  Q  A  V  C  E  V
                         430                              440

T(n1129,n1164)
                          |
       TTCTCGACACACGCAAAGGATATGGATGTTGTTGAGCTGCTGACTGAAGTCAATAAGAAG
6421   ---------+---------+---------+---------+---------+---------+ 6480
         F  S  T  H  A  K  D  M  D  V  V  E  L  L  T  E  V  N  K  K
                         450                              460

T(n2430)                                       A(n2426)
               |                                              | | intron 7
       GTCGCTTGTGGATTTCAGACATCACAGGGATCGAATATTTTGAAACAGATGCCAGAGGTA
6481   ---------+---------+---------+---------+---------+---------+ 6540
         V  A  C  G  F  Q  T  S  Q  G  S  N  I  L  K  Q  M  P  E
                         470                              480
```

Fig. 3 (cont.)

```
                                     Repeat 5
                  ==========================================
          CTTGAAACAAACAATGCATGTCTAACTTTTAAGGACACAGAAAAATAGGCAGAGGCTCCT
     6541 ---------+---------+---------+---------+---------+---------+ 6600

=======================>
          TTTGCAAGCCTGCCGCGCGTCAACCTAGAATTTTAGTTTTTAGCTAAAATGATTGATTTT
     6601 ---------+---------+---------+---------+---------+---------+ 6660
          GAATATTTTATGCTAATTTTTTTGCGTTAAATTTTGAAATAGTCACTATTTATCGGGTTT
     6661 ---------+---------+---------+---------+---------+---------+ 6720
          CCAGTAAAAAATGTTTATTAGCCATTGGATTTTACTGAAAACGAAAATTTGTAGTTTTTC
     6721 ---------+---------+---------+---------+---------+---------+ 6780
          AACGAAATTTATCGATTTTTAAATGTAAAAAAAAATAGCGAAAATTACATCAACCATCAA
     6781 ---------+---------+---------+---------+---------+---------+ 6840
          GCATTTAAGCCAAAATTGTTAACTCATTTAAAAATTAATTCAAAGTTGTCCACGAGTATT
     6841 ---------+---------+---------+---------+---------+---------+ 6900
                      Repeat 5
              <===========================================================
          ACACGGTTGGCGCGCGGCAAGTTTGCAAAACGACGCTCCGCCTCTTTTTCTGTGCGGCTT
     6901 ---------+---------+---------+---------+---------+---------+ 6960

T(nl163)
          =====                                            |        |
          GAAAACAAGGGATCGGTTTAGATTTTTCCCCAAAATTTAAATTAAATTTCAGATGACATC
     6961 ---------+---------+---------+---------+---------+---------+ 7020
                                                             M  T  S

CCGCCTGCTCAAAAAGTTCTACTTTTGGCCGGAAGCACGAAACTCTGCCGTCTAAAATTC
     7021 ---------+---------+---------+---------+---------+---------+ 7080
             R  L  L  K  K  F  Y  F  W  P  E  A  R  N  S  A  V  *
                     490                           500
          ACTCGTGATTCATTGCCCAATTGATAATTGTCTGTATCTTCTCCCCAGTTCTCTTTCGC
     7081 ---------+---------+---------+---------+---------+---------+ 7140
          CCAATTAGTTTAAAACCATGTGTATATTGTTATCCTATACTCATTTCACTTTATCATTCT
     7141 ---------+---------+---------+---------+---------+---------+ 7200
          ATCATTTCTCTTCCCATTTTCACACATTTCCATTTCTCTACGATAATCTAAAATTATGAC
     7201 ---------+---------+---------+---------+---------+---------+ 7260
          GTTTGTGTCTCGAACGCATAATAATTTTAATAACTCGTTTTGAATTTGATTAGTTGTTGT
     7261 ---------+---------+---------+---------+---------+---------+ 7320
          GCCCAGTATATATGTATGTACTATGCTTCTATCAACAAAATAGTTTCATAGATCATCACC
     7321 ---------+---------+---------+---------+---------+---------+ 7380
          CCAACCCCACCAACCTACCGTACCATATTCATTTTTGCCGGGAATCAATTTCGATTAATT
     7381 ---------+---------+---------+---------+---------+---------+ 7440
          TTAACCTATTTTTTCGCCACAAAAAATCTAATATTTGAATTAACGAATAGCATTCCCATC
     7441 ---------+---------+---------+---------+---------+---------+ 7500
          TCTCCCGTGCCGGAATGCCTCCCGGCCTTTTAAAGTTCGGAACATTTGGCAATTATGTAT
     7501 ---------+---------+---------+---------+---------+---------+ 7560
          AAATTTGTAGGTCCCCCCCATCATTTCCCGCCCATCATCTCAAATTGCATTCTTTTTTCG
     7561 ---------+---------+---------+---------+---------+---------+ 7620
          CCGTGATATCCCGATTCTGGTCAGCAAAGATCT
     7621 ---------+---------+---------+--- 7653
```

Fig. 3 (cont.)

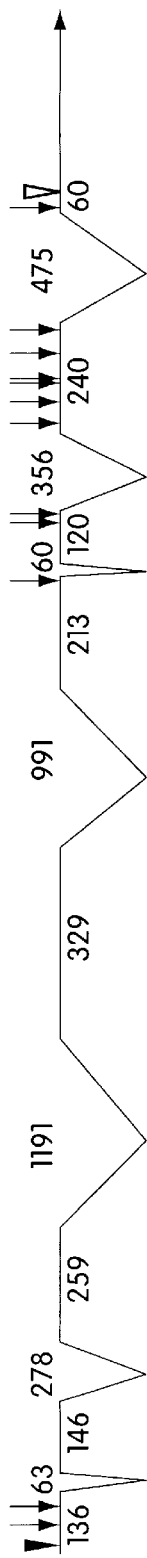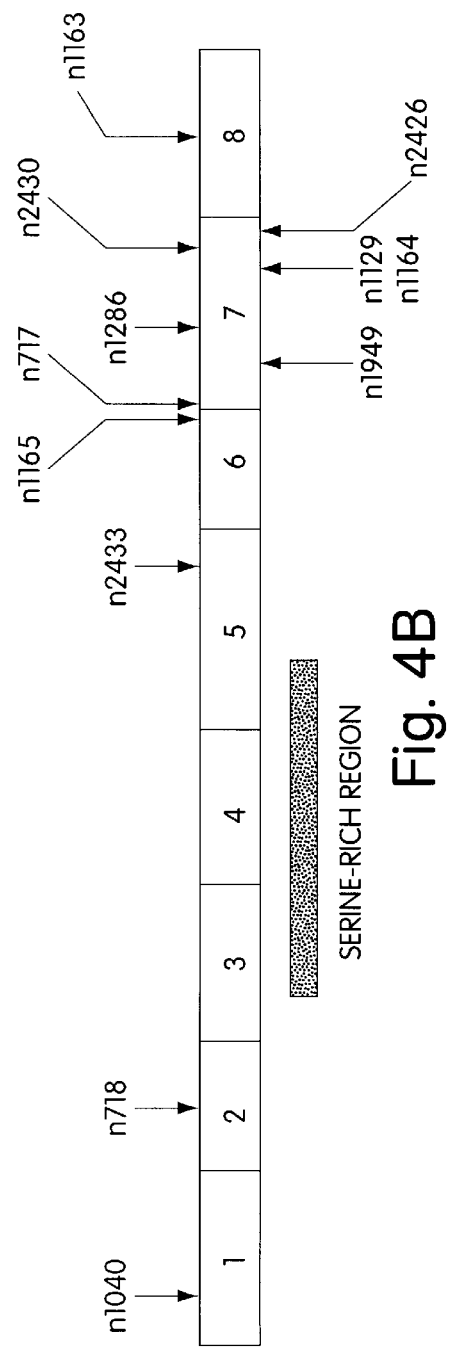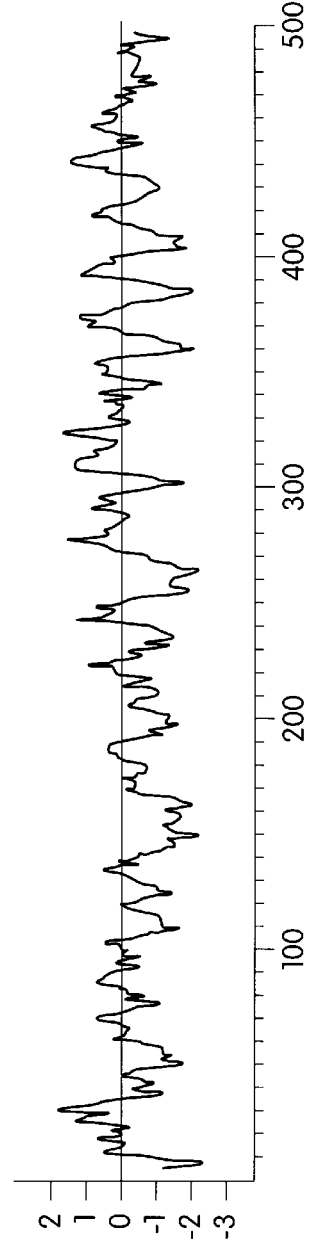
Fig. 4A
Fig. 4B
Fig. 5

Alignment of ced-3 and Human Interleukin -1β convertase

```
ICE     1    MADKVLKEKRKLFIRSM....GEGTINGLLDELLQTRVLNKEEMEKVKRE
             .:  .::|.|:  |.:    :. .::::|: |:...|||.:: :.:. .
Ced-3   1    ...MMRQDRRSLLERNIMMFSSHLKVDEILEVLIAKQVLNSDNGDMIN.S
                                            ↓
                                            F

BGAFQ        =================================================
PBA          =================================================

47   NATVMDKTRALIDSVIPKGAQACQ.ICITYICEEDSYLAGTLGLSADQTS
             :||.:| |.::..|  ..|.  |  : ::  .. :.:.. ||:.|:  |  ..
        47   CGTVREKRREIVKAVQRPGDVAFDAFYDALRSTGHEGLAEVLEPLARSVD
                                    ↓
                                    R
BFAFQ        =================================================
             ================================================= autocleavage site
        96   GNYLNMQ.....................DSQGVLSSF.......
             :|  ::::                     || : :|||
        97   SNAVEFECPMSPASHRRSRALSPAGYTSPTRVHRDSVSSVSSFTSYQDIY
                        serine-rich region
BGAFQ        =================================================
PBA          =================================================

112  ....................PAPQAVQDNPAMPTSSGSEGNVKLCSLE
                                 |:..|....|. :.|| .:..   :| .
        147  SRARSRSRSRALHSSDRHNYSSPPVNAFPSQPSSANSSFTGCSSLGYSSS
BGAFQ        =================================================
PBA          ===

140  EAQRIWKQKSAEIYPIMDK..................SSRTRLAL
             ...:.|..::. | : :.                   ||. :.|
        197  RNRSFSKASGPTQYIFHEEDMNFVDAPTISRVFDEKTMYRNFSSPRGMCL
BGAFQ        =================================================
```

Fig. 6A

```
ICE    167  IICNEEFDSIPRRTGAEVDITGMTMLLQNLGYSVDVKKNLTASDMTTELE
            || ||.|: :| |.|...|  ..:| |:. :||.| .|.|||:.:|  .:
Ced-3  247  IINNEHFEQMPTRNGTKADKDNLTNLFRCMGYTVICKDNLTGRGMLLTIR

BGAFQ       =================================================

217  AFAHRPEHKTSDSTFLVFMSHGIREGICGKKHSEQVPDI.LQLNAIFNML
            .||.:..|  :||.:||::|||   :.|.|      |.|| :  :.|:::|
       297  DFAKHESH..GDSAILVILSHGEENVIIG......VDDIPISTHEIYDLL

BGAFQ       ================================================= active site   autocleavage site
       266  NTKNCPSLKDKPKVIIIQACRGDSPGVVW.FKDSVGVSGNLSLPTTEEFE
            |. |.|.| :|||::::|||||:..: .: . |||:. ..:  .. :: :
       339  NAANAPRLANKPKIVFVQACRGERRDNGFPVLDSVDGVPAFLRRGWDNRD
                                         ↓
                                         S
BGAFQ       ====================================

315  DDAI.............KKAHIEKDFIAFCSSTPDNVSWRHPTMGSVFI
            :. :             :|  . : |:: :..|:: ||||:...|| ||
       389  GPLFNFLGCVRPQVQQVWRKKPSQADILIRYATTAQYVSWRNSARGSWFI
                             ↓                ↓
                            stop             stop 351  GRLIEHMQEYACSCDVEEIF....RKVRFSFEQPDGRAQMPTT.ERVT.L
            . :.| : ..| . || |::   :|| :|: .:|.. :.  | .: |
       439  QAVCEVFSTHAKDMDVVELLTEVNKKVACGFQTSQGSNILKQMPEMTSRL
                  ↓              ↓              ↓ ↓
                  V              V              K F 395  TRCFYLFPGH*.... 404
            : ||::|:
       489  LKKFYFWPEARNSAV 503
```

Fig. 6A (cont.)

Alignment of Ced-3 and Murine NEDD-2

```
Ced-3   251 EHFEQMPTRNGTKADKDNLTNLFRCMGYTVICKDNLTGRGMLLTIRDFAK 300
                                          :|| :.. ::  .
NEDD-2    1 .................................MLTVQVYRT         9

301 HESHGDSAILVILSHGEENVIIGVDDIPISTHEIYDLLNAANAPRLANKP 350
            :: :::  :|  :   |:  :::  : |:: .::|
         10 SQKCSSSKHVV......EVLLD...PLGT.SFCSLL........PP     37

351 KIVFVQACRGERRDNGFPVLDSVDGVPAFLRRGWDNRDGPLFNFLGCVRP 400
             .: : :  ::  |   :  :::   :: :::
         38 PLLLYETDRGVDQQDGKNHTQSPGC.........EESDAGKEELM...   73
                                                   V n1129, n1164
                                                   ↓
        401 QVQQVWRKKPSQADILIRYATTAQYVSWRNSARGSWFIQAVCEVFSTHAK 450
            .: .::|:::: :| . .  | |:  | ||||:|
         74 .....KMRLPTRSDMICGYACLKGNAAMRNTKRGSWYIEALTQVFSERAC 118
                                  n2426 K   F n1163
                                        ↑     ↑
        451 DMDVVELLTEVNK..KVACGFQTSQGSNILKQMPEMTSRLLKKFYFWPEA 498
            ||. |:::: ||    .:  :|: .  :|: . ..|
        119 DMHVADMLVKVNALIKEREGYAPGTEFHRCKEMSEYCSTLCQQLYLFPGY 168

499 RNSAV 503
            . :
        169 PPT... 172
```

Fig. 6B

Alignment of N-terminal regions of ced-3/ICE- related proteins

```
c. briggsae ced-3    MMRQDRWSLLERNILEFSSKLQADLILDVLIAKQVLNSDNGDVINSCRTERDNEKEITVKAVQRRGDEAFDAFYDALRDTGHNDLADVLMPLSR---PNPV
ced-3 protein        MMRQDRRSLLERNIMMFSSHLKVDEILEVLIAKQVLNSDNGDMINSCGTVREKRREIVKAVQRPGDVAFDAFYDALRSTGHEGLAEVLEPLARSVDSNAV  100
C.vulgaris ced-3     M--------------ADKIL----------------------------------------------RAKRKQFINSV---SIGTINGLLDELLEK-------RVLNQEEM----DKI
Mouse ICE.gw         M--------------ADKVL----------------------------------------------KEKRKLFIRSM---GEGTINGLLDELLQT-------RVLNKEEM----EKV
Human ICE.GW
Consensus            M..............AD.IL....................................R.KRK....V...G......V...D.L..T......VL.....Y----..V c. briggsae ced-3    PMECPMSPSSHRRSRALSPPGYASPTRVHRDSISSVSSFTSTYQDVYSRARSSSRPLQSSDRHNYMSAA-TSFPSQPSSANSSFTGCASLGYSSSRN
ced-3 protein        EFECPMSPASHRRSRALSPAGYTSPTRVHRDSVSSVSSVSSFTSYQD-IYSRARSRSRS-RALHSSDRHNYSSPPVNAFPSQPSSANSSFTGCSSLGYSSSRN  198
C.vulgaris ced-3     ----------------------------------------------------STSRSSRPLHTSDRHNYVSPS-NSFQSQPASANSSFTGSSSLGYSSSRT
Mouse ICE.gw         KLA---NITAMDKARDLCDHVSKKGPQASQIFITYICNEDCYL----------AGILELQSAPSAE--TFVAT------EDSKGGHPSSSETKEEQNKED-G
Human ICE.GW         KRE---NATVMDKTRALIDSVIPKGAQACQICITYICEEDSYL----------AGTGLGLSADQTSG--NYLNM------QDSQGVLSSFPAPQAVQDNPAMP
Consensus            ..E.......RAL..................I......SY....S.SRS.R.L.SSDRHNY.S....F.SQP.SANS SFTG.-SLGYSSSR.

c. briggsae ced-3    RSFSKTSAQSQYIFHEEDMNYVDAPTIHRVFDEKTMYRNFSSPRGLCLIINNEEHFEQMPTRNGTKADKDNLTNIFRCMGYTVICKDNLTIGREMLSTIRSF
ced-3 protein        RSFSKASGPTQYIFHEEDMNFVDAPTISRVFDEKTMYRNFSSPRGMCLIINNEHFEQMPTRNGTKADKDNLTNLFRCMGYTVICKDNLTIGRGMLLTIRDF  298
C.vulgaris ced-3     RSYSKASAHSQYIFHEEDMNYVDAPTIHRVFDEKTMYRNFSTPRGLCLIINNEEHFEQMPTRNGTKPDKDNISNLFRCMGYIVHCKDNLTIGRMML-TIRDF
Mouse ICE.gw         TFPGLTGTLKFCPLEKAQKLWKENPS--EIY--PIMNTT-TRTR-LALIICNTFFQHLSPRVGAQVDLREMKLLLEDLGYTVKVKENLTALEMVKEVKEF
Human ICE.GW         TSSGSEGNVKLCSLEEAQRIWKQKSA--EIY--PIMDKS-SRTR--LALIICNEEEFDSIPRRTGAEVDITGMTMLLQNLGYSVDVKKNLTASDMTTELEAF
Consensus            RS.SK.S...QYIFHEEDMN.VDAPTI.RVFDEKTMYRNFSSPRGLCLIINNEEHFEQMPTRNGTK.DKDN.TNLFRCMGYTV.CKDNLIGR.ML.TIR.F c. briggsae ced-3    GRNDMH---GDSAILVILSHGEENVIIG----VNVHEIYDLLNAAANAPRLANKPKLVFVQACRG
ced-3 protein        AKHESH---GDSAILVILSHGEENVIIG----VDDIP--ISTHEIYDLLNAAANAPRLANKPKLVFVQACRG
C.vulgaris ced-3     AKNETH---GDSAILVILSHGEENVIIG----VDDVS--VNVHEIYDLLNAAANAPRLANKPKLVFVQACRG  360
Mouse ICE.gw         AACPEHKTSDSTFLVFMSHGIQEGICGTTYSNEVSDILKVDTIFQMMNYTLNCPSLKDKPKVIIIQACRG
Human ICE.GW         AHRPEHKTSDSTFLVFMSHGIREGICGKKHSEQVPDILQLNAIFNMLNVTKNCPSLKDKPKVIIIQACRG
Consensus            A.....H..CDSAILVILSHGEENVIIG....VDDVS-...VHEIYDLLNAAANAPRLANKPKLVFVQACRG
```

Fig. 6C

Alignment of C-terminal regions of ced-3/ICE/NEDD-2 - related proteins

```
ICE C-terminus        DSPGVVW--  -------- -FKDSVG-- -------- -------- -------V
Mouse ICE C-ter       EKQGVVL--  -------- -LKDSVR-- -------- -------- -------D
C.briggsae C-ter      ERRDNGFP-  -------- -VLDSVDG- -------- -VPSLI-- -RRGWDN
ced-3 cterminus       ERRDNGFP-  -------- -VLDSVDG- -------- -VPAFL-- -RRGWDN 386
C. vulgaris C-terminus ERRDVGFP- -------- -VLDSVDG- -------- -VPALI-- -RRGWDK
nedd-2 protein.gw     MLTVQVYRTS QKCSSSKHVV EVLLDPLGTS FCSLLPPPLL LYETDRGVDQ Consensus             E........  ........ ..LDSV... ........ ..P..... ..RG.D.

ICE C-terminus        SGNL---SLP TTEEFE---D DAIKKA-HIE KDFIAFCSST PDNVSWRHPT
Mouse ICE C-ter       SEE----DFL TDAIFE---D DGIKKA-HIE KDFIAFCSST PDNVSWRHPV
C.briggsae C-ter      RDG-PLFNFL GCVRPQV--Q QVWRKK-PSQ ADMLIAYATT AQYVSWRNSA
ced-3 cterminus       RDG-PLFNFL GCVRPQV--Q QVWRKK-PSQ ADILIAYATT AQYVSWRNSA 432
C. vulgaris C-terminus GDG-P--NFL GCVRPQA--Q QVWRKK-PSQ ADILIAYATT AQYVSWRNSA
nedd-2 protein.gw     QDGKNHTQSP GCEESDAGKE ELMKMRLPTR SDMICGYACL KGNAAMRNTK Consensus             .DG-.--.FL GC........ ....K.-P.. ..D......D ..YA.T....VSWRN..

ICE C-terminus        MGSVTIGRLI EHMQEYACSC DVEEIFRKV- -RF----SFE QPDGRAQMPT
Mouse ICE C-ter       RGSLFIESLI KHMKEYAWSC DLEDIFRKV- -RF----SFE QPEFRLQMPT
C.briggsae C-ter      RGSWFIQAVC EVFSLHAKDM DVVELLTEVN KKVA--CGFQ TSQGSNILKQ
ced-3 cterminus       RGSWFIQAVC EVFSTHAKDM DVVELLTEVN KKVA--CGFQ TSQGSNILKQ 480
C. vulgaris C-terminus RGSWFIQAVC EVFSLHAKDM DVVELLTEVN KKVA--CGFQ TSQGANILKQ
nedd-2 protein.gw     RGSWYIEALT QVFSERACDM HVADMLVKVN ALIKEREGYA PGTEFHRCKE Consensus             RGS.FI.A.. EVFS..A.DM DV.E.L..V. ......GF.. ...G....K.

ICE C-terminus        T-ERVT-LTR CFYLFPGH-- --------  
Mouse ICE C-ter       A-DRVT-LTK RFYLFPGH-- --------  
C.briggsae C-ter      MPELTSRLLK KFYFWPEDRG RNSAV
ced-3 cterminus       MPELTSRLLK KFYFWPEAR- -NSAV 503
C. vulgaris C-terminus MPEMTSRLLK KFYFWPEDRN RSSAV
nedd-2 protein.gw     MSEYCSTLCQ QLYLFPG--- -YPPT Consensus             M.E..S..L.K .FY..P..-- -.....
```

Fig. 6D

Lines

```
1  01  MMRQDRRSLLERNIMMFSSHLKVDEILEVLIAKQVLNSDNGDMINSCGTV  50
2      ......W_.......LE...K.QA.L..D...............V....R.E
3                              TVSISLI..R.......  M.....

1  51  REKRREIVKAVQRPGDVAFDAFYDALRSTGHEGLAEVLEPLARSVDSNAV  100
2      .DNEK........R..E..........D...ND..D..M..S.P   .P.
3

1  101 EFECPMSPASHRRSRALSPAGYTSPTRVHRDSVSSVSSFTS_YQDIYSRA  149
2      PM......S...........P .A.........I........T...V....
3                                                      S 1  150 RSRSR-SRALHSSDRHNYSSPPVNAFPSQPSSANSSFTGCSSLGYSSSRN  198
2      ..S..S..P.Q.......M.AA_TS.....  .........A........
3      T...--..P..T......V..S_.S.Q...A........S.........T 1  199 RSFSKASGPTQYIFHEEDMNFVDAPTISRVFDEKTMYRNFSSPRGMCLI   247
2      .....T.AQS..........Y......H.................L...
3      ..Y....AHS..........Y......H.............T...L...

1  248 INNEHFEQMPTRNGTKADKDNLTNLFRCMGYTVICKDNLTGRGMLLTIRD  297
2      ........................I...................E..S...S
3      ...............P....IS........I.H......... .M.....

1  298 FAKHESHGDSAILVILSHGEENVIIGVDDIPISTHEIYDLLNAANAPRLA  347
2      .GRNDM......................VSVNV................
3      ...N.T......................VSVNV....x...........

1  348 NKPKIVFVQACRGERRDNGFPVLDSVDGVPAFLRRGWDNRDGPLFNFLGC  397
2      ....L......................SLI................
3      ....L............V...........LI.....KG...  .....

1  398 VRPQVQQVWRKKPSQADILIRYATTAQYVSWRNSARGSWFIQAVCEVFST  447
2      ...................M..A......................L
3      ....A..............A..........................L 1  448 HAKDMDVVELLTEVNKKVACGFQTSQGSNILKQMPEMTSRLLKKFYFWPE  497
2      ...............................L...............
3      ...........................A....... L...........

1  498 __ARN__SAV   503
2      DRG..._...
3      __D..RS...
```

Fig. 7

Interleukin-1β convertase cDNA sequence

```
   1  AAAAGGAGAG AAAAGCCATG GCCGACAAGG TCCTGAAGGA GAAGAGAAAG
  51  CTGTTTATCC GTTCCATGGG TGAAGGTACA ATAAATGGCT TACTGGATGA
 101  ATTATTACAG ACAAGGGTGC TGAACAAGGA AGAGATGGAG AAAGTAAAAC
 151  GTGAAAATGC TACAGTTATG GATAAGACCC GAGCTTTGAT TGACTCCGTT
 201  ATTCCGAAAG GGGCACAGGC ATGCCAAATT TGCATCACAT ACATTTGTGA
 251  AGAAGACAGT TACCTGGCAG GGACGCTGGG ACTCTCAGCA GATCAAACAT
 301  CTGGAAATTA CCTTAATATG CAAGACTCTC AAGGAGTACT TTCTTCCTTT
 351  CCAGCTCCTC AGGCAGTGCA GGACAACCCA GCTATGCCCA CATCCTCAGG
 401  CTCAGAAGGG AATGTCAAGC TTTGCTCCCT AGAAGAAGCT CAAAGGATAT
 451  GGAAACAAAA GTCGGCAGAG ATTTATCCAA TAATGGACAA GTCAAGCCGC
 501  ACACGTCTTG CTCTCATTAT CTGCAATGAA GAATTTGACA GTATTCCTAG
 551  AAGAACTGGA GCTGAGGTTG ACATCACAGG CATGACAATG CTGCTACAAA
 601  ATCTGGGGTA CAGCGTAGAT GTGAAAAAAA ATCTCACTGC TTCGGACATG
 651  ACTACAGAGC TGGAGGCATT TGCACACCGC CAGAGCACA AGACCTCTGA
 701  CAGCACGTTC CTGGTGTTCA TGTCTCATGG TATTCGGGAA GGCATTTGTG
 751  GGAAGAAACA CTCTGAGCAA GTCCCAGATA TACTACAACT CAATGCAATC
 801  TTTAACATGT TGAATACCAA GAACTGCCCA AGTTTGAAGG ACAAACCGAA
 851  GGTGATCATC ATCCAGGCCT GCCGTGGTGA CAGCCCTGGT GTGGTGTGGT
 901  TTAAAGATTC AGTAGGAGTT TCTGGAAACC TATCTTTACC AACTACAGAA
 951  GAGTTTGAGG ATGATGCTAT TAAGAAAGCC CACATAGAGA AGGATTTTAT
1001  CGCTTTCTGC TCTTCCACAC CAGATAATGT TTCTTGGAGA CATCCCACAA
1051  TGGGCTCTGT TTTTATTGGA AGACTCATTG AACATATGCA AGAATATGCC
1101  TGTTCCTGTG ATGTGGAGGA AATTTTCCGC AAGGTTCGAT TTTCATTTGA
1151  GCAGCCAGAT GGTAGAGCGC AGATGCCCAC CACTGAAAGA GTGACTTTGA
1201  CAAGATGTTT CTACCTCTTC CCAGGACATT AAAATAAGGA AACTGTATGA
1251  ATGTCTGCGG GCAGGAAGTG AAGAGATCGT TCTGTAAAAG GTTTTTGGAA
1301  TTATGTCTGC TGAATAATAA ACTTTTTTTG AAATAATAAA TCTGGTAGAA
1351  AAATGAAAAA AAAAAAAAA AAA
```

Fig. 8

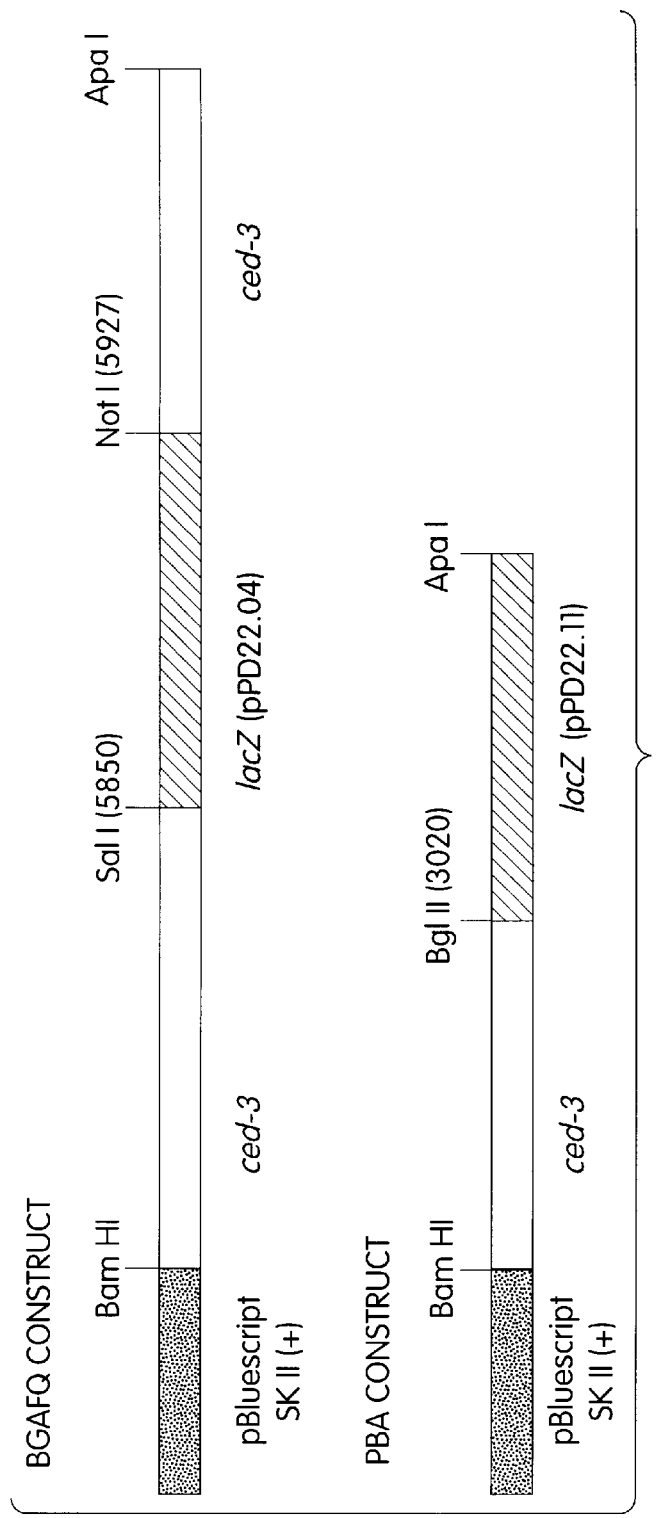
Fig.9A
Fig.9B

![5,962,301]

RELATEDNESS OF HUMAN INTERLEUKIN-1β CONVERTASE GENE TO A C. ELEGANS CELL DEATH GENE, INHIBITORY PORTIONS OF THESE GENES AND USES THEREFOR

RELATED APPLICATION

This application is a continuation-in-part of U.S. Ser. No. 08/282,211, filed Jul. 11, 1994; which is a divisional of 07/984,182, filed Nov. 20, 1992, now abandoned; which is a continuation-in-part of U.S. Ser. No. 07/897,788, filed Jun. 12, 1992, now abandoned. The teachings of U.S. Ser. No. 07/897,788 are incorporated by reference.

GOVERNMENT FUNDING

Work described herein was supported by grants GM24663 and GM24943 from the U.S. Public Health Service. The U.S. Government has certain rights in the invention.

BACKGROUND

Cell death is a fundamental aspect of animal development. Many cells die during the normal development of both vertebrates (Glucksmann, *Biol. Rev. Cambridge Philos. Soc.* 26:59–86 (1951)) and invertebrates (Truman, *Ann. Rev. Neurosci.* 7:171–188 (1984)). These deaths appear to function in morphogenesis, metamorphosis and tissue homeostasis, as well as in the generation of neuronal specificity and sexual dimorphism (reviewed by Ellis et al., *Ann. Rev. Cell Biol.* 7:663–698 (1991)). An understanding of the mechanisms that cause cells to die and that specify which cells are to live and which cells are to die is essential for an understanding of animal development.

The nematode *Caenorhabditis elegans* is an appropriate organism for analyzing naturally-occurring or programmed cell death (Horvitz et al., *Neurosci. Comment.* 1:56–65 (1982)). The generation of the 959 somatic cells of the adult *C. elegans* hermaphrodite is accompanied by the generation and subsequent deaths of an additional 131 cells (Sulston and Horvitz, *Dev. Biol.* 82:110–156 (1977); Sulston et al., *Dev. Biol.* 100:64–119 (1982)). The morphology of cells undergoing programmed cell death in *C. elegans* has been described at both the light and electron microscopic levels (Sulston and Horvitz, *Dev. Biol.* 82:100–156 (1977); Robertson and Thomson, *J. Embryol. Exp. Morph.* 67:89–100 (1982)).

Many genes that affect *C. elegans* programmed cell death have been identified (reviewed by Ellis et al., *Ann. Rev. Cell Biol.* 7:663–698 (1991)). The activities of two of these genes, ced-3 and ced-4, are required for the onset of almost all *C. elegans* programmed cell deaths (Ellis and Horvitz, *Cell* 44:817–829 (1986)). When the activity of either ced-3 or ced-4 is eliminated, cells that would normally die instead survive and can differentiate into recognizable cell types and even function (Ellis and Horvitz, *Cell* 44:817–829 (1986); Avery and Horvitz, *Cell* 51:1071–1078 (1987); White et al., *Phil. Trans. R. Soc. Lond. B.* 331:263–271 (1991)). Genetic mosaic analyses have indicated that the ced-3 and ced-4 genes most likely act in a cell autonomous manner within dying cells, suggesting that the products of these genes are expressed within dying cells and either are cytotoxic molecules or control the activities of cytotoxic molecules (Yuan and Horvitz, *Dev. Biol.* 138:33–41 (1990)).

SUMMARY OF THE INVENTION

This invention is based mainly on two experimental findings and their implications: 1) that human interleukin-1β convertase (ICE), a cysteine protease with specificity for aspartate and which cleaves pro-interleukin-1β substrate in the P1 position to yield the active cytokine which is involved in the inflammatory response in humans, has considerable similarity to the protein encoded by the *C. elegans* cell death gene, ced-3; and 2) that fusion constructs containing amino-terminal portions of the ced-3 gene can prevent cell death in *C. elegans*. As discovered by Applicant, the human ICE and nematode Ced-3 proteins have an overall amino acid identity of 28%. A higher degree of similarity was found in the carboxyl-terminal region, a region shown to be critical for the activities of both proteins. Furthermore, three sequences important for ICE activity, the region surrounding the active cysteine and two autocleavage sites, have been shown to be conserved in the ced-3 gene product.

Thus, significant structural similarity has been shown between two proteins which previously were thought to be unrelated (to have dissimilar physiological roles). This finding leads to several implications, some of which are:

1) that the human ICE gene has an activity similar to that of ced-3 in causing cell death;
2) that the Ced-3 protein is also a cysteine protease with a substrate specificity similar to that of ICE;
3) that mutations in the ICE gene corresponding to mutations in the ced-3 gene will produce similar effects, such as inactivation and constitutive activation;
4) that the ced-3 and ICE genes are members of a family of structurally related genes, referred to herein as the ced-3/ICE family, some of which are likely to be cell death genes and some of which may encode substrate-specific proteases;
5) that inhibitors of ICE, such as peptide aldehydes which contain the ICE recognition site or a substituted recognition site and the cowpox virus CrmA protein, may also be useful for inhibiting cell deaths; and
6) that inhibitors of ced-3, such as inhibitory portions of the gene or encoded product, may also be useful for inhibiting inflammation.

This hitherto unknown connection between a cell death protein and a protease involved in the inflammatory response provides a basis for developing novel drugs and methods for the treatment of acute and chronic inflammatory disease, of leukemias in which IL-1β is implicated, and of diseases and conditions characterized by cell deaths (such as myocardial infarction, stroke, traumatic brain injury, viral and other types of pathogenic infection, neural and muscular degenerative diseases such as ALS and spinal cord injury, aging, hair loss). In addition, drugs which increase cell deaths and which are useful for reducing the size or proliferative capacity of cell populations, such as cancerous cells, infected cells, cells which produce autoreactive antibodies, and hair follicle cells, as well as drugs which incapacitate or kill organisms, such as pests, parasites and recombinant organisms, can be developed using the ced-3, ICE, and other ced-3/ICE genes and their gene products.

This work also provides probes and methods for identifying additional members of the ced-3/ICE gene family. Genes related to ced-3 and ICE are expected to exist in various organisms. Some of these may be cell death genes and/or proteases. The sequences of these related genes and their encoded products can be compared, for instance, using computer-based analysis, to determine their similarities. Structural comparisons, for example, would indicate those regions or features of the genes or encoded products which are likely to be functionally similar and important. Such information can be used to design drugs which mimic or alter the activity of the ced-3, ICE, or other ced-3/ICE genes, and which may, thus, be useful in the various medical and agricultural applications mentioned above.

In addition, another mammalian protein, the murine NEDD-2 protein (also known as Ich-1), was also found to be similar to Ced-3. Interestingly, NEDD-2 is not significantly similar to ICE. Thus, another mammalian cell death gene was identified.

Also described herein is the discovery that fusion constructs which encode an amino-terminal portion of the Ced-3 protein fused to β-galactosidase act as inhibitors of cell death in *C. elegans*. Due to its structural similarity to Ced-3, constructs encoding corresponding portions of the human ICE protein are also expected to inhibit the enzymatic activity of ICE in cleaving interleukin-1β. Thus, inhibitors comprising an amino-terminal portion of the Ced-3 protein, ICE protein or another member of the Ced-3/ICE family and RNAs and DNA constructs which express these protein portions are potentially useful for decreasing cell deaths and/or inflammation involved in various pathologies. Methods for identifying other inhibitory portions of the ced-3 and ICE genes are also described.

Furthermore, deletion of the inhibitory amino-terminal portions of the ced-3 and ICE genes may result in constitutive activation of the genes. Constitutively activated carboxyl-terminal portions of the genes, or their encoded products, may thus be useful in applications where increased cell deaths or an increased inflammatory response are desired.

Also provided are compounds with mutations of the active site cysteine in ICE, Ced-3, CPP-32, or NEDD-2 and methods for inhibition of cell death by administering these compounds. In ICE, the active site cysteine is at position 285, in Ced-3 the active site cysteine is at position 358, in CPP-32 the active site cystein is at position 163, and in NEDD-2 the active cysteine is at position 303. Preferably, the mutation is a missense mutation which changes one or more amino acids, including the active site cysteine. More preferably, the cysteine is replaced by an alanine or a serine. Most preferably, the cysteine is replaced by an alanine.

In another aspect, the invention features a drug for inhibiting the activity of a gene selected from the group consisting of ced-3 and a gene which belongs to the ced-3/ICE gene family, comprising an inhibitor of interleukin-1β convertase. Preferably, the drug reduces cell deaths, or is a peptide aldehyde containing the amino acid sequence Tyr-Val-Xaa-Asp, wherein Xaa is selected from Ala, His, Gln, Lys, Phe, Cha, and Asp; or is Ac-Tyr-Val-Ala-Asp-CHO, also referred to as inhibitor B, or is the cowpox virus CrmA protein or a portion thereof. Preferably, the activity being inhibited is polypeptide ICE activity.

In a related aspect, the invention provides methods for inhibiting cell death by administering inhibitors of ICE or related proteases. Preferably, the peptide is a peptide aldehyde containing the amino acid sequence Tyr-Val-Xaa-Asp, wherein Xaa is selected from Ala, His, Gln, Lys, Phe, Cha, and Asp; or is Ac-Tyr-Val-Ala-Asp-CHO, also referred to as inhibitor B, or is the cowpox virus CrmA protein or a portion thereof, or any protease inhibitor containing an aspartate residue in the position corresponding to the P1 site in the substrate linked to a protease-inactivating chemical moiety. Preferably, the cell death being inhibited is cell death in human nerve cells, including motoneurons. For example, the methods of the invention may be used to prevent or decrease the number of cell deaths due to amyotrophic lateral sclerosis, spinal cord injury, stroke, brain trauma, Parkinsonism, Huntington's disease, Alzheimer's disease, or spinocerebellar degeneration (e.g., cerebello-olivary degeneration of Holmes, Friedreich's ataxia).

In another aspect, the invention features an inhibitor of the activity of the ced-3 gene, which includes a portion of the ced-3 gene sequence. Preferably, the gene portion is a portion of the nucleotide sequence of (SEQ ID NO: 1), selected from the group consisting of:
 a) nucleotides 1 to approximately 5850;
 b) nucleotides 1 to approximately 3020; and
 c) an inhibitory subportion (a) and (b); the gene portion encodes an amino acid sequence of the Ced-3 protein shown in FIG. 6A (SEQ ID NO: 2), selected from the group consisting of:
 a) amino acids 1 to approximately 372;
 b) amino acids 1 to approximately 149; and
 c) an inhibitory subportion of (a) and (b).

The inhibitor of the ced-3 gene may further include a heterologous structural gene fused 3' of the gene portion, e.g., *E. coli* lacZ, or a transcriptional signal and a translational signal suitable for expression of the gene portion in a host cell. Preferably, the transcriptional and the translational signals are those of the ced-3 gene. In related aspects, the invention features inhibitors of the activity of the ced-3 gene, which include RNA encoded by the sense strand of a nucleotide sequence of FIG. 3 (SEQ ID NO: 1), the nucleotide sequence being selected from the group consisting of:
 a) nucleotides 1 to approximately 5850;
 b) nucleotides 1 to approximately 3020; and
 c) an inhibitory subportion of (a) and (b);
 or an inhibitor which is a protein having an amino acid sequence of the Ced-3 protein shown in FIG. 6A (SEQ ID NO: 2), selected from the group consisting of:
 a) amino acids 1 to approximately 372;
 b) amino acids 1 to approximately 149; and
 c) an inhibitory subportion of (a) and (b); or which is a non-peptide mimetic of the inhibitor of the foregoing, sequences from FIG. 6A; or a construct selected from BGAFQ and PBA; or the encoded product of a construct selected from BGAFQ and PBA; or a non-peptide mimetic of the protein encoded by a construct selected from BGAFQ and PBA.

In another related aspect, the invention also features an inhibitor of the activity of the ced-3 gene, comprising protein having an amino acid sequence of ICE shown in FIG. 6A (SEQ ID NO: 4), selected from the group consisting of:
 a) amino acids 1 to 298;
 b) amino acids 1 to 111; and
 c) an inhibitory subportion of (a) and (b); or
  which is a portion of the ICE gene which encodes the ICE, or an inhibitory subportion of said gene; or RNA encoded by the gene portion which encodes ICE; or a non-peptide mimetic of the protein of ICE. In another related aspect, the invention also features an inhibitor of the activity of the ced-3 gene, which includes a portion of the protein product of a gene which is structurally related to the ced-3 gene, and which protein product corresponds to an amino acid sequence of the Ced-3 protein shown in FIG. 6A (SEQ ID NO: 2), selected from the group consisting of:
 a) amino acids 1 to approximately 372;
 b) amino acids 1 to approximately 149; and
 c) an inhibitory subportion of (a) and (b); or
  an inhibitor which is a portion of a gene which is structurally related to the ced-3 gene, and encodes one of the foregoing, ced-3-related amino acid fragments, or an inhibitory subsection of said gene portion; or RNA encoded by the immediately foregoing, gene portion; or a non-peptide mimetic of the foregoing, amino acid fragments which are related to ced-3.

In another aspect, the invention features a method for identifying a portion of the ced-3 gene which inhibits the activity of the ced-3 gene, which method includes the steps of:
 a) injecting wild-type nematodes with a portion of the ced-3 gene under conditions suitable for expression of said gene portion; and
 b) detecting a decrease in programmed cell deaths,
  whereby a decrease in programmed cell deaths is indicative of a portion of the ced-3 gene which inhibits the activity of said gene.

In related aspects, the invention features a method of identifying a portion of a gene which is structurally related to ced-3 and which inhibits the activity of the ced-3 gene, wherein the structurally related DNA is substituted for the ced-3 DNA in the immediately foregoing method. Preferably, the structurally related DNA is ICE-encoding DNA. The invention also includes isolated DNA which is identified by these methods.

In another aspect, the invention features an inhibitor of the activity of the ICE gene which includes a portion of the gene which encodes an amino sequence of ICE shown in FIG. 6A (SEQ ID NO: 4), selected from the group consisting of:
 a) amino acids 1 to approximately 298;
 b) amino acids 1 to approximately 111; and
 c) an inhibitory subportion of (a) and (b).
This inhibitor may further include a heterologous structural gene fused 3' of the gene portion, or a transcriptional signal and a translational signal suitable for expression of the gene portion in a host cell.

In related aspects, the invention features inhibitors of the activity of the ICE gene, which include RNA encoded by the gene which encodes ICE; and inhibitors which are amino acid sequences of ICE shown in FIG. 6A (SEQ ID NO: 4), selected from the group consisting of:
 a) amino acids 1 to approximately 298;
 b) amino acids 1 to approximately 111;
 c) an inhibitory subportion of (a) and (b);
  which is a non-peptide mimetic of the immediately foregoing, amino acid fragments; and a portion of the ced-3 gene. Preferably, the inhibitory portion of the ced-3 gene is a nucleotide sequence of FIG. 3 (SEQ ID NO: 1), selected from the group consisting of:
 a) nucleotides 1 to approximately 5850;
 b) nucleotides 1 to approximately 3020;
 c) an inhibitory subportion of (a) and (b); or
  is a nucleotide sequence which encodes an amino acid sequence of the Ced-3 protein shown in FIG. 6A (SEQ ID NO: 2), selected from the group consisting of:
 a) amino acids 1 to approximately 372;
 b) amino acids 1 to approximately 149; and
 c) an inhibitory subportion of (a) and (b); or
  is an inhibitor which is a nucleotide sequence including a construct selected from BGAFQ and PBA, or which is the encoded products thereof. In one embodiment, the nucleic acid inhibitor further includes a heterologous structural gene fused 3' of the gene portion, or a transcriptional signal and a translational signal suitable for expression of the gene portion in a host cell.

In related aspects, the invention features inhibitors of the activity of the ICE gene, including RNA encoded by the sense strand of a portion of the ced-3 gene, which is a nucleotide sequence of FIG. 3 (SEQ ID NO: 1), selected from the group consisting of:
 a) nucleotides 1 to approximately 5850;
 b) nucleotides 1 to approximately 3020; and
 c) an inhibitory subportion of (a) and (b);
  and an inhibitor which is a protein having an amino acid sequence of the Ced-3 protein shown in FIG. 6A (SEQ ID NO: 4), selected from the group consisting of:
 a) amino acids 1 to approximately 372;
 b) amino acids 1 to approximately 149; and
 c) an inhibitory subportion of (a) and (b); or
  an inhibitor which is a protein having an amino acid sequence of the ced-3 protein shown in FIG. 6A (SEQ ID NO: 4), selected from the group consisting of:
 a) amino acids 1 to approximately 372;
 b) amino acids 1 to approximately 149; and
 c) an inhibitory subportion of (a) and (b); or
  an inhibitor which is a non-peptide mimetic of the immediately foregoing, protein fragments.

In a further related aspect, the invention features an inhibitor of the activity of the ICE gene which includes a portion of the protein product of a gene which is structurally related to said ICE gene, which portion corresponds to an amino acid sequence of the Ced-3 protein shown in FIG. 6A (SEQ ID NO: 2), selected from the group consisting of:
 a) amino acids 1 to approximately 372;
 b) amino acids 1 to approximately 149; and
 c) an inhibitory subportion of (a) and (b); or
  an inhibitor which is a portion of a gene which is structurally related to the ICE gene, which gene encodes one of the immediately foregoing, amino acid sequences, or an inhibitory subsection of such a gene which is structurally related to a gene encoding the foregoing, protein fragments; or RNA encoded by the gene which encodes the foregoing, protein fragments; or a non-peptide mimetic of the foregoing, protein fragments.

In another aspect, the invention features a method for identifying a portion of ICE which inhibits the activity of said ICE, comprising the steps of:
 a) combining a portion of ICE with ICE and a substrate of ICE under conditions suitable for cleavage of the substrate by ICE; and
 b) detecting a decrease in cleavage of the substrate, whereby a decrease in cleavage of the substrate is indicative of a portion of ICE which inhibits the activity of said enzyme.

In a related aspect, the invention features an isolated inhibitory portion of the ICE protein identified by this method and nucleic acid encoding this inhibitory portion.

In another aspect, the invention features a method for identifying a portion of the protein product of a gene which is structurally related to the ced-3 and ICE genes, and which inhibits the activity of ICE, comprising the steps of:
 a) combining a portion of the protein product of a gene which is structurally related to the ced-3 and ICE genes with ICE and a substrate of ICE under conditions suitable for cleavage of the substrate by ICE; and
 b) detecting a decrease in cleavage of the substrate, whereby a decrease in cleavage of the substrate is indicative of a portion of the protein product of a gene which is structurally related to the ced-3 and ICE genes and inhibits the activity of ICE. In related aspects, the invention features an isolated inhibitory portion identified by the method and isolated nucleic acid encoding the inhibitory portion identified by the method.

In other aspects, the invention features inhibitors of the activity of a gene belonging to the ced-3/ICE family of structurally related genes, comprising DNA selected from the group consisting of:

a) a portion of the nucleotide sequence of FIG. 3 (SEQ ID NO: 1), selected from the group consisting of:
  1) nucleotides 1 to approximately 5850;
  2) nucleotides 1 to approximately 3020; and
  3) an inhibitory subportion of (a.1) and (a.2);
b) DNA encoding an amino acid sequence of the Ced-3 protein shown in FIG. 6A (SEQ ID NO: 2), selected from the group consisting of:
  1) amino acids 1 to approximately 372;
  2) amino acids 1 to approximately 149; and
  3) an inhibitory subportion of (b.1) and (b.2);
c) a portion of the ICE gene which encodes an amino acid sequence of ICE shown in FIG. 6A (SEQ ID NO: 4), selected from the group consisting of:
  1) amino acids 1 to approximately 298;
  2) amino acids 1 to approximately 111; and
  3) an inhibitory subportion of (c.1) and c.2);
d) a portion of the ced-3/ICE gene which encodes an amino acid sequence corresponding to a portion of the Ced-3 protein shown in FIG. 6A (SEQ ID NO: 2), which Ced-3 portion selected from the group consisting of:
  1) amino acids 1 to approximately 372;
  2) amino acids 1 to approximately 149; and
  3) an inhibitory subportion of (d.1) and (d.2); and
e) a portion of a ced-3/ICE gene other than the ced-3/ICE gene which encodes an amino acid sequence corresponding to a portion of the Ced-3 protein shown in FIG. 6A (SEQ ID NO: 2), said Ced-3 portion selected from the group consisting of:
  1) amino acids 1 to approximately 372;
  2) amino acids 1 to approximately 149; and
  3) an inhibitory subportion of (e.1) and (e.2); or comprising RNA encoded by the DNA of a)–e), immediately above; or protein encoded by the DNA of a)–e), immediately above; or a non-peptide mimetic of the proteins and fragments encoded by the DNA of a)–e), immediately above.

In another aspect, the invention features a drug for reducing cell deaths, which includes an inhibitor of the activity of the ced-3 gene, selected from the group consisting of:

a) a portion of the ced-3 gene;
b) a product encoded by a portion of the ced-3 gene;
c) a non-peptide mimetic of an inhibitory portion of the Ced-3 protein;
d) a portion of the ICE gene;
e) a product encoded by a portion of the ICE gene;
f) a non-peptide mimetic of an inhibitory portion of the ICE protein;
g) a portion of a gene which is structurally related to the ced-3 gene;
h) a product encoded by the gene portion of (g); and
i) a non-peptide mimetic of the protein encoded by the gene portion of (g).

Preferably, the inhibitor is selected from the group consisting of:

a) DNA having a nucleotide sequence of FIG. 3 (SEQ ID NO: 1), selected from the group consisting of:
  1) nucleotides 1 to approximately 5850;
  2) nucleotides 1 to approximately 3020; and
  3) an inhibitory portion of (a.1) and (a.2);
b) DNA encoding an amino acid sequence of the Ced-3 protein shown in FIG. 6A (SEQ ID NO: 2), selected from:
  1) amino acids 1 to approximately 372;
  2) amino acids 1 to approximately 149; and
  3) an inhibitory portion of (b.1) and (b.2);
c) RNA encoded by DNA of (a);
d) RNA encoded by DNA of (b);
e) protein having an amino acid sequence of the Ced-3 protein shown in FIG. 6A (SEQ ID NO: 2), selected from the group consisting of:
  1) amino acids 1 to approximately 372;
  2) amino acids 1 to approximately 149; and
  3) inhibitory portion of (e.1) and (e.2); and
f) a non-peptide mimetic of the protein of e); or selected from the group consisting of:
g) DNA encoding an amino acid sequence of ICE shown in FIG. 6A (SEQ ID NO: 4), selected from the group consisting of:
  1) amino acids 1 to approximately 298;
  2) amino acids 1 to approximately 111; and
  3) an inhibitory portion of (g.1) and (g.2);
h) RNA encoded by DNA of g);
i) protein having an amino acid sequence of ICE shown in FIG. 6A (SEQ ID NO: 4), selected from the group consisting of:
  1) amino acids 1 to approximately 298;
  2) amino acids 1 to approximately 111; and
  3) an inhibitory portion of (i.1) and (i.2); and
j) a non-peptide mimetic of the protein of i); or selected from the group consisting of:
k) protein encoded by a portion of a gene which is structurally related to the ced-3 gene, said protein portion corresponding to an amino acid sequence of the Ced-3 protein shown in FIG. 6A (SEQ ID NO: 2) selected from the group consisting of:
  1) amino acids 1 to approximately 372;
  2) amino acids 1 to approximately 149; and
  3) an inhibitory portion of (k.1) and (k.2);
l) DNA encoding the protein of (k) or inhibitory subportion thereof;
m) RNA encoding the protein of (k) or inhibitory subportion thereof; and
n) a non-peptide mimetic of the protein of (k).

In a related aspect, the invention features a method for treating a condition characterized by cell deaths, comprising administering the drug of which is an inhibitor of the activity of the ced-3 gene or protein.

In another aspect, the invention features a drug for reducing cell deaths, which includes an inhibitor of the activity of the ICE gene or protein, selected from the group consisting of:

a) a portion of the ICE gene;
b) a product encoded by a portion of the ICE gene;
c) a non-peptide mimetic of an inhibitory portion of the ICE protein;
d) a portion of the ced-3 gene;

e) a product encoded by a portion of the ced-3 gene;

f) a non-peptide mimetic of an inhibitory portion of the Ced-3 protein;

g) a portion of a gene which is structurally related to the ced-3 gene and the ICE gene;

h) a product encoded by the gene portion of (e); and i) a non-peptide mimetic of the protein encoded by (g).

Preferably, the drug is structurally related to the ced-3 gene and the ICE gene, and is selected from the group consisting of:

a) a portion of said related gene;

b) a product encoded by the gene portion of (a);

c) a non-peptide mimetic of the protein product encoded by (a);

d) a portion of the ICE gene;

e) a product encoded by the gene portion of (d);

f) a non-peptide mimetic of a protein product encoded by (d);

g) a portion of the ced-3 gene;

h) a product encoded by the gene portion of (g); and i) a non-peptide mimetic of the protein product encoded by (g).

In another aspect, the invention features an anti-inflammatory drug, comprising an inhibitor of the activity of the ICE gene or protein, or inhibitory portion thereof, selected from the group consisting of:

a) a portion of the ICE gene;

b) a product encoded by a portion of the ICE gene;

c) a portion of the ced-3 gene;

d) a product encoded by a portion of the ced-3 gene;

e) a portion of a gene which is structurally related to the ced-3 gene and ICE gene; and f) a product encoded by a portion of a gene which is structurally related to the ced-3 gene and the ICE gene.

Preferably, the anti-inflammatory drug is an inhibitor selected from the group consisting of:

a) DNA encoding an amino acid sequence of ICE shown in FIG. 6A (SEQ ID NO: 4), selected from the group consisting of:
  1) amino acids 1 to approximately 298;
  2) amino acids 1 to approximately 111; and
  3) an inhibitory portion of (a.1) and (a.2);

b) RNA encoded by DNA of (a) or an inhibitory subportion thereof;

c) protein having an amino acid sequence of ICE shown in FIG. 6A (SEQ ID NO: 4), selected from the group consisting of:
  1) amino acids 1 to approximately 298;
  2) amino acids 1 to approximately 111; and
  3) an inhibitory portion of (c.1) and (c.2);

d) a non-peptide mimetic of the protein of (c); or the inhibitor is selected from the group consisting of:

e) DNA having a nucleotide sequence of FIG. 3 (SEQ ID NO: 1), selected from the group consisting of:
  1) nucleotides 1 to approximately 5850;
  2) nucleotides 1 to approximately 3020; and
  3) an inhibitory portion of (e.1) and (e.2);

f) DNA encoding an amino acid sequence of the Ced-3 protein shown in FIG. 6A (SEQ ID NO: 2), selected from the group consisting of:
  1) amino acids 1 to approximately 372;
  2) amino acids 1 to approximately 149; and
  3) an inhibitory portion of (f.1) and (f.2);

g) RNA encoded by DNA of (e);

h) RNA encoded by DNA of (f);

i) protein having an amino acid sequence of the Ced-3 protein shown in FIG. 6A (SEQ ID NO: 2), selected from the group consisting of:
  1) amino acids 1 to approximately 372;
  2) amino acids 1 to approximately 149; and
  3) an inhibitory portion of (i.1) and (i.2); and k) a non-peptide mimetic of the protein of (i); or the inhibitor is selected from the group consisting of:

l) protein encoded by a portion of a gene which is structurally related to the ced-3 and ICE genes, said protein portion corresponding to an amino acid sequence of ICE shown in FIG. 6A (SEQ ID NO: 4), selected from the group consisting of:
  1) amino acids 1 to approximately 298;
  2) amino acids 1 to approximately 111; and
  3) an inhibitory portion of (1.1) and (1.2);

m) DNA encoding the protein of (1);

n) RNA encoding the protein of (1); and o) a non-peptide mimetic of the protein of (1).

In related aspects, the invention features methods for treating inflammation, which includes administering the drug of a)–o), immediately above.

In another aspect, the invention features a method for altering the occurrence of cell death, which includes altering the activity of a cell death gene which is structurally related to ced-3. Preferably, the structurally related gene is ICE.

In another aspect, the invention features a drug for increasing cell deaths, which includes a molecule, or active portion thereof, selected from:

a) DNA comprising a gene which belongs to the ced3/ICE gene family;

b) RNA encoded by the DNA of (a);

c) protein encoded by the DNA of (a);

d) an agent which is structurally similar to and mimics the activity of the protein of (c);

e) an agonist of the activity of a gene which belongs to the ced-3/ICE gene family;

f) DNA comprising a constitutively activated mutated form of a gene which belongs to the ced-3/ICE gene family;

g) RNA encoded by the DNA of (e);

h) protein encoded by the DNA of (e);

i) an agent which is structurally similar to and mimics the activity of a protein encoded by the DNA of (e); and j) an agonist of the activity of a constitutively activated mutated form of a gene which belongs to the ced-3/ICE gene family.

In a related aspect, the invention features the drug of a)–f), immediately foregoing, wherein the gene which belongs to the ced-3/ICE gene family is ICE. Preferably, where drug is a constitutively activated mutated form of the gene which belongs to the ced-3/ICE gene family encodes a carboxyl-terminal portion of a protein product of the wild-type gene, the carboxyl-terminal portion having a deletion of an amino-terminal portion which corresponds to an amino acid sequence of the Ced-3 protein shown in FIG. 6A (SEQ ID NO: 2), selected from the group consisting of:

k) amino acids 1 to approximately 372;

l) amino acids 1 to approximately 149; and m) an inhibitory subportion of (h) and (l).

More preferably, the protein product of the wild-type gene has sequences corresponding to the autocleavage sites of ICE and the protein product of the wild-type gene is selected from the group consisting of:

n) the uncleaved form of the protein product; and
o) the subunits corresponding to the active subunits of ICE.

In a related aspect, the invention features a method for reducing the proliferative capacity or size of a population of cells, including contacting the cells with the drug for increasing cell deaths selected from the immediately foregoing, group a)–j), under conditions suitable for activity of the drug. Preferably, the population of cells is selected from the group consisting of:

a) cancerous cells;
b) cells which produce autoreactive antibodies;
c) infected cells;
d) hair follicle cells;
e) cells which are critical to the life of a parasite;
f) cells which are critical to the life of a pest; and
g) cells which are critical to the life of a recombinant organism.

In another aspect, the invention features a drug for decreasing cell deaths comprising a molecule selected from the group consisting of:

a) single stranded nucleic acid having all or a portion of the antisense sequence of a gene which is structurally related to ced-3, said nucleic acid which is complementary to the mRNA of the gene;
b) DNA which directs the expression of (a);
c) a mutated form of a gene which is structurally related to ced-3, does not cause cell death and antagonizes the activity of the wild-type gene; and
d) an antagonist of the activity of a gene which is structurally related to ced-3.

Preferably, the structurally related gene is ICE.

In a related aspect, the invention features a method for treating, in a human or other animal, a condition characterized by cell deaths, which method includes administering the drug of a)–d), immediately foregoing, to the human or other animal under conditions suitable for activity of the drug. Preferably, the condition is selected from the group consisting of:

a) myocardial infarction;
b) stroke;
c) degenerative disease;
d) traumatic brain injury;
e) hypoxia;
f) pathogenic infection; and
g) hair loss.

In another aspect, the invention features a diagnostic probe for a disease characterized by cell deaths, comprising a molecule selected from the group consisting of:

a) all or a portion of the ced-3 gene (SEQ ID NO: 1) which is specific to said ced-3 gene;
b) RNA encoded by the ced-3 gene;
c) degenerate oligonucleotides derived from the amino acid sequence of the Ced-3 protein (SEQ ID NO: 2);
d) an antibody directed against the Ced-3 protein;
e) all or a portion of the ICE gene (SEQ ID NO: 3) which is specific to said ICE gene;
f) RNA encoded by the ICE gene;
g) degenerate oligonucleotides derived from the amino acid sequence of ICE (SEQ ID NO: 4);
h) an antibody directed against ICE;
i) a gene which is structurally related to the ced-3 gene, or portion thereof specific to said structurally related gene;
j) RNA encoded by the structurally related gene;
k) degenerate oligonucleotides derived from the amino acid sequence of the protein product of a gene which is structurally related to ced-3; and
d) an antibody directed against the protein product of a gene which is structurally related to ced-3.

In related aspects, the invention provides methods for diagnosis of a diseases characterized by cell deaths, which included detecting an abnormality in the sequence of a gene which is structurally related to ced-3; or which includes detecting an abnormality in the activity of a gene which is structurally related to ced-3. Preferably, the structurally related gene is ICE. In another aspect, the invention provides a diagnostic probe for an inflammatory disease, which includes a molecule selected from the group consisting of:

a) all or a portion of the ced-3 gene shown in FIG. 3 (SEQ ID NO: 1) which is specific to the ced-3 gene;
b) RNA encoded by (a);
c) degenerate oligonucleotides derived from the amino acid sequence of the Ced-3 protein as shown in FIG. 6A (SEQ ID NO: 2);
d) an antibody directed against the Ced-3 protein;
e) a gene which is structurally related to the ced-3 and ICE genes, or portion thereof which is specific for said related gene;
f) RNA encoded by (a);
g) degenerate oligonucleotides derived from the amino acid sequence of the protein encoded by (e); and
h) an antibody directed against the protein encoded by (e).

In a related aspect, the invention features a method for diagnosis of an inflammatory disease, which includes detecting an abnormality in the sequence of a gene which is a member of the ced-3/ICE gene family; or which includes detecting an abnormality in the activity of a gene which belongs to the ced-3/ICE gene family, or an encoded product thereof. Preferably, the gene which is a member of the ced-3/ICE family is ced-3.

In another aspect, the invention features an isolated substrate-specific protease having the amino acid sequence of the Ced-3 protein shown in FIG. 6A (SEQ ID NO: 2). In a related aspect, the invention provides an isolated substrate-specific protease, consisting essentially of a protein product of a gene which is structurally related to the ced-3 and ICE genes. Preferably, the protease cleaves after aspartate residues or is a cysteine protease.

In another aspect, the invention features isolated ICE having an alteration which reduces the activity of the enzyme, the alteration selected from the group consisting of:

a) Lysine to Phe at amino acid 26;
b) Gly to Arg at amino acid 65;
c) Cys to Ala or Ser at amino acid 285;
d) Gly to Ser at amino acid 287;
e) Glu to termination at amino acid 324;
f) Trp to termination at amino acid 340;
g) Ala to Val at amino acid 361;
h) Glu to Lys at amino acid 390; and
i) Thr to Phe at amino acid 393.

The invention also provides methods for inhibiting cell death by administering the ICE polypeptides of a)–i), above.

In related aspects, the invention provides isolated DNA which encodes a mutated ICE having the amino acid alterations specified in a)–h), immediately foregoing, and RNA encoded by this DNA.

In another aspect, the invention features an isolated gene belonging to the ced-3/ICE family of structurally related genes which has a mutation conferring reduced activity of the gene, said mutation resulting in an amino acid alteration corresponding to an amino acid alteration of the Ced-3 protein which inactivates the Ced-3 protein. The product of the gene may be either RNA or protein.

In another aspect, the invention features a constitutively activated cell death protein comprising an amino acid sequence of the Ced-3 protein shown in FIG. 6A (SEQ ID NO: 2), selected from the group consisting of:
 a) the amino acids from approximately 150 to 503;
 b) the amino acids from approximately 373 to 503;
 c) the amino acids from approximately 150 to 372;
 d) (b) and (c) together;
 e) an active subportion of (a), (b), and (c); and
 f) combinations of a)–e).

Preferably, the constitutively activated protein further includes a subportion of the region of Ced-3 from amino acids 1 to 149, as shown in FIG. 6A (SEQ ID NO: 2), which subportion which enhances and does not inhibit the activity of the protein. In related aspects, the invention features drugs for increasing cell deaths, including a molecule selected from the proteins of a)–f), immediately foregoing, or a nucleic acid encoding said protein. In a related aspect, the invention features isolated nucleic acid encoding the proteins a)–f), immediately foregoing.

In another aspect, the invention features constitutively activated cell death protein having an amino acid sequence of ICE shown in FIG. 6A (SEQ ID NO: 4), selected from the group consisting of:
 a) the amino acids from approximately 111 to 404;
 b) the amino acids from approximately 298 to 404;
 c) the amino acids from approximately 111 to 297;
 d) (b) and (c) together;
 e) an active subportion of (a), (b), and (c); and
 f) combinations of these.

In a related aspect, the invention features isolated nucleic acid encoding a protein of a)–f), immediately foregoing.

In another aspect, the invention features a method for identifying a gene which is structurally related to the ced-3 gene and the ICE gene, comprising detecting a gene with:
 a) a probe derived from the ced-3 gene or a product encoded by the ced-3 gene; and
 b) a probe derived from the ICE gene or a product encoded by the ICE gene, and a method for identifying a gene which belongs to the ced-3/ICE family of structurally related genes, comprising detecting a gene with a probe selected from the group consisting of:
  a) a probe derived from a gene which is structurally related to the ced-3 gene and the ICE gene; and
  b) a probe derived from the consensus sequence of a conserved region in genes belonging to the ced-3/ICE gene family.

In related aspects, the invention provides isolated genes identified by these methods. Preferably, the isolated gene has a cell death activity, a protease activity, or both.

In another aspect, the invention provides isolated DNA selected from the group consisting of:
 a) a region of a gene belonging to the ced-3/ICE family of structurally related genes which is conserved among two or more family members; and
 b) the consensus sequence of a conserved region in genes belonging to the ced-3/ICE gene family, or encoded product thereof.

In another aspect, the invention provides a method for identifying a gene which interacts with a ced-3/ICE gene belonging to this family, which includes identifying a mutation which enhances or suppresses the activity of a ced-3/ICE gene in a nematode, whereby the enhancing or suppressing mutation is indicative of a gene which interacts with the ced-3/ICE gene. Preferably, the ced-3/ICE gene is selected from the group consisting of:
 a) a wild-type ced-3 gene;
 b) a mutated ced-3 gene, the nematode being a mutant nematode;
 c) a transgene which is a wild-type form of said ced-3/ICE gene, the nematode being a transgenic nematode having an inactivated endogenous ced-3 gene; and
 d) a transgene which is a mutated form of said ced-3/ICE gene, the nematode being a transgenic nematode having an inactivated endogenous ced-3 gene. In a related aspect, the invention provides an isolated gene identified by the above method.

In another aspect, the invention provides a bioassay for identifying an agent which affects the activity of a gene belonging to the ced-3/ICE family of structurally related genes, comprising the steps of:
 a) introducing an agent into a transgenic nematode which expresses a ced-3/ICE gene; and
 b) detecting an alteration in the occurrence of cell deaths in the transgenic nematode, wherein an alteration indicates that the agent affects the activity of the ced-3/ICE gene.

Preferably, the ced-3/ICE gene is selected from a wild-type gene and a mutated gene. In a related aspect, the invention features an agent identified by the bioassay.

In another aspect, the invention features an isolated protein having cell death activity and the amino acid sequence of the NEDD-2 protein shown in FIG. 6B (SEQ ID NO: 13), or an active portion thereof and isolated nucleic acid encoding the protein. In a related aspect the invention features isolated NEDD-2 protein having an alteration which inactivates the protein, said alteration selected from the group consisting of:
 a) Ala to Val at amino acid 117;
 b) Cys to Ser or Ala at amino acid 303;
 c) Glu to Lys at amino acid 483; and
 d) Ser to Phe at amino acid 486; and
  isolated nucleic acid encoding the protein.

In another aspect, the invention features isolated protein which is structurally similar to Ced-3 and has an alteration at a conserved amino acid corresponding to an amino acid of the Ced-3 protein selected from the group consisting of:
 a) Ser 183;
 b) Met 234;
 c) Arg 242;
 d) Leu 246;
 e) Ile 247;
 f) Ile 248;
 g) Asn 250;
 h) Phe 253;

i) Arg 259;
j) Gly 261;
k) Asp 265;
l) Gly 277;
m) Tyr 278;
n) Val 280;
o) Lys 283;
p) Asn 285;
q) Leu 286;
r) Thr 287;
s) Met 291;
t) Phe 298;
u) His 304;
v) Asp 306;
w) Ser 307;
x) Leu 310;
y) Val 311;
z) Ser 314;
aa) His 315;
bb) Gly 316;
cc) Ile 321;
dd) Gly 323;
ee) Ile 334;
ff) Asn 339;
gg) Pro 344;
hh) Leu 346;
ii) Lys 349;
jj) Pro 350;
kk) Lys 351;
ll) Gln 356;
mm) Ala 357;
nn) Cys 358;
oo) Arg 359;
pp) Gly 360;
qq) Asp 371;
rr) Asp 414;
ss) Arg 429;
tt) Gly 434;
uu) Ser 435;
vv) Ile 438;
ww) Ala 449;
xx) Val 452;
yy) Leu 488;
aa) Tyr 493;
aaa) Pro 496; and isolated nucleic acid encoding these proteins.

By asp-ase is meant a protease which specifically cleaves a substrate after aspartate residues and therefore has a requirement for an aspartate in the P1 position of the substrate pocket. For example, ICE, granzyme B, prICE, NEDD-2, CPP-32 (Fernandes-Alnemri et al., *J. Biol. Chem.* 269:30761 (1994)), ICE-2, and ICE-4 are all asp-ases. Preferably, the asp-ase is ICE.

By inhibitors of asp-ases is meant any compound which decreases the enzymatic activity of an asp-ase by more than 5%, more preferably by more than 25%, and most preferably by more than 60% under standard in vitro assay condition. See, for example, Thornberry et al. (Thornberry et al., *Nature* 356:768–774 (1992)) and Lazednik et al. (Lazednik et al., *Nature* 371:346–347 (1994)) for appropriate assay conditions. Examples of several asp-ase inhibitors are provided herein.

BRIEF DESCRIPTION OF THE DRAWINGS

FIG. 3 shows the nucleotide sequence (SEQ ID NO: 1) of ced-3 and deduced amino acid sequence (SEQ ID NO: 2). The genomic sequence of the ced-3 region was obtained from plasmid pJ107. The introns and the positions of 12 ced-3 mutations are indicated. The likely translation initiation site is indicated by a solid arrowhead. The SL1 splice acceptor of the RNA is boxed. Repetitive elements are indicated as arrows above the relevant sequences. Numbers on the sides indicate nucleotide positions. Numbers under the amino acid sequence indicate codon positions.

FIG. 4A shows the genomic structure of the ced-3 gene and the location of the mutations. The sizes of the introns and exons are given in bp. The downward arrows indicate the positions of 12 EMS-induced mutations of ced-3. The arrow pointing right indicates the direction of transcription. The solid arrowhead indicates the translation initiation site. The open arrowhead indicates the termination codon.

FIG. 4B shows the locations of the mutations relative to the exons (numbered 1–7) and the encoded serine-rich region in ced-3.

FIG. 5 shows a Kyte-Doolittle hydrophobicity plot of the Ced-3 protein.

FIG. 6A shows the alignment of the amino acid sequences of Ced-3 (SEQ ID NO: 2) and human interleukin-1β convertase (ICE; SEQ ID NO: 4). Vertical bars indicate identical amino acids and single and double dots indicate similar amino acids, where double dots signifies closer similarity than a single dot. The serine-rich region and inactivating mutations of Ced-3 are indicated. The active site and autocleavage sites of ICE are indicated. The portions of the Ced-3 protein encoded by the BGAFQ and PBA constructs are also shown.

FIG. 6B shows the alignment of the amino acid sequences of Ced-3 (SEQ ID NO: 2) and murine NEDD-2 (SEQ ID NO: 13). Vertical bars and single and double dots signify degrees of similarity as in FIG. 6A. Inactivating mutations of Ced-3 are shown.

FIG. 6C shows the alignment of the amino-terminal regions of the Ced-3 proteins of three nematode species (*C. briggsae, C. elegans, and C. vulgaris*) and mouse (SEQ ID NO: 14) and human ICEs. A consensus sequence is also shown. Amino acid positions with the same residue in more than half of the sequences are shaded. Completely conserved amino acids are also boxed.

FIG. 6D shows the alignment of carboxyl-terminal regions of the three nematode Ced-3 proteins, human and mouse ICEs, and the nouse NEDD-2 protein. Except for NEDD-2, these sequences are contiguous with the corresponding sequences shown in FIG. 6C. A consensus sequence and amino acid conservation are also shown.

FIG. 7 shows a comparison of the Ced-3 proteins of C. elegans (line 1; SEQ ID NO: 2) and two related nematode species, C. briggsae (line 2; SEQ ID NO: 5) and C. vulgaris (line 3; SEQ ID NO: 6). The conserved amino acids are indicated by ".". Gaps inserted in the sequence for the purpose of alignment are indicated by "_".

FIG. 8 shows the interleukin-1β convertase cDNA sequence (SEQ ID NO: 3).

FIG. 9A shows a schematic representation of two fusion constructs that can prevent programmed cell death.

FIG. 9B shows a schematic representation of the lacZ-containing portion of the fusion constructs.

FIG. 11A shows the results obtained with Ac-YVAD-CHO. FIG. 11B shows the results obtained with a chloromethylketone peptide inhibitor of ICE (Ac-YVAD-CMK); FIG. 11C shows the results obtained with leupeptin, a control peptide aldehyde protease inhibitor (Ac-LLR-CHO); and FIGS. 11D and 11E show the results obtained with a control chloromethylketone protease inhibitor, Tos-Lys-CMK, (FIG. 11D) or the membrane permeable calpain inhibitor Ed64 (FIG. 11E).

FIG. 12A shows the effect of Ac-YVAD-CHO, and FIG. 12B shows the effect of Ac-YVAD-CHO. Results are expressed as % control, where control represents cultures supplied with muscle extract at plating

DETAILED DESCRIPTION OF THE INVENTION

Figure 1:
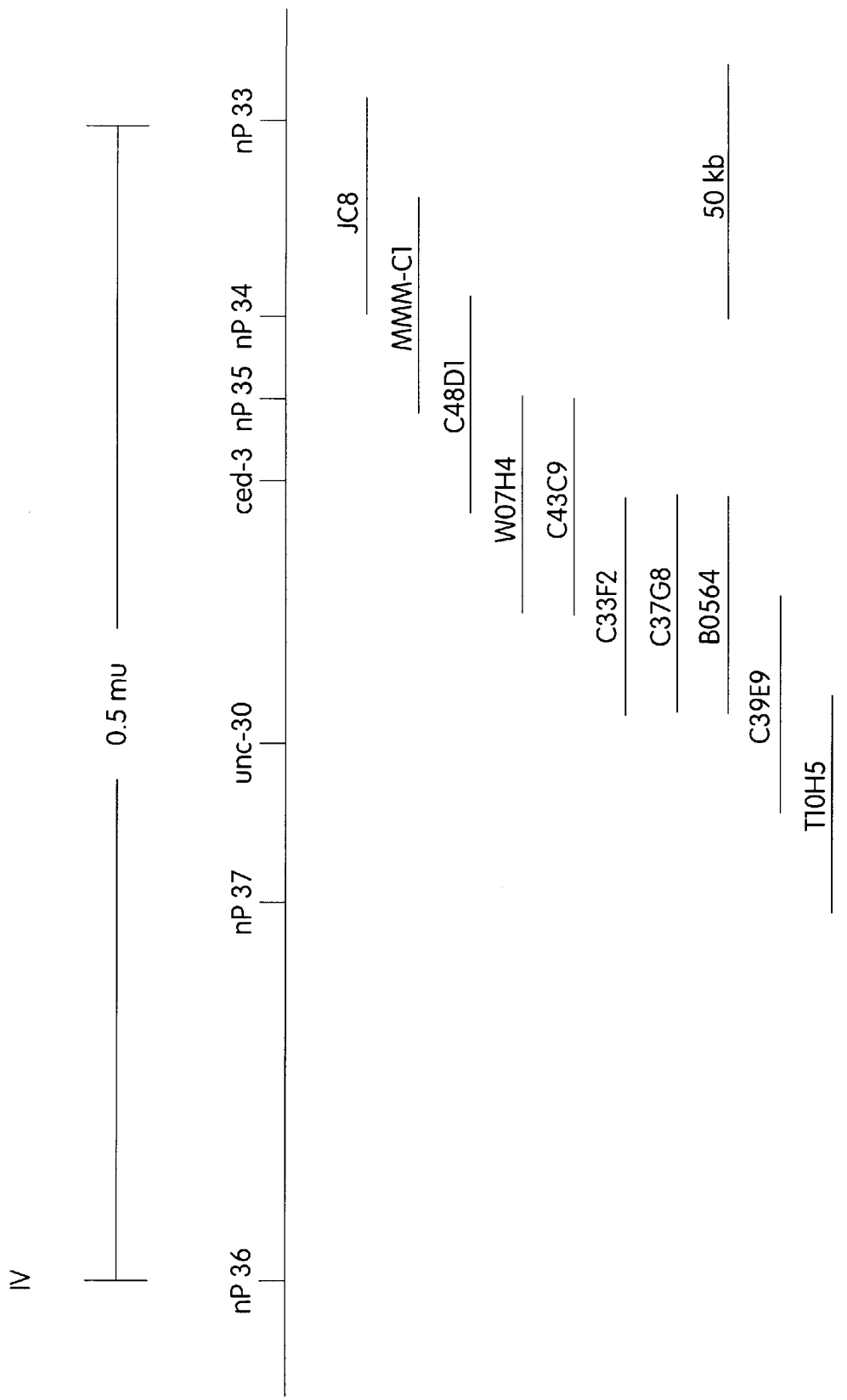
FIG. 1 shows the physical and genetic maps of the ced-3 region on chromosome IV.

This invention is based on the discovery that the human enzyme interleukin-1β convertase (ICE) has significant structural similarity to the protein product of the C. elegans cell death gene, ced-3. The activities of ced-3 and another cell death gene, ced-4, have been shown to be required for almost all the cell deaths which occur during the development of the nematode. ICE is a cysteine protease whose physiological significance has been thought to be related to its role in the maturation of one form of interleukin-1 (IL-1), a major mediator of the immune and inflammatory response (Fuhlbrigge et al., in: *The Year in Immunology*, Cruse and Lewis (eds.), Karger, Basel, 1989, pp. 21–37). There are two distantly related forms of IL-1, α and β, of which the β form is the predominant species. ICE selectively converts pro-interleukin-1β to the active cytokine, IL-1β. The production of active IL-1β has been implicated in acute and chronic inflammatory diseases, septic shock, and other physiological processes, including wound healing and resistance to viral infection (Ray et al., *Cell* 69:597–604 (1992)). As a result of this discovery, an enzyme which has been known to be involved in the inflammatory response and inflammatory diseases is implicated as having a role in cell death processes. This discovery is consistent with the notion that cell death genes equivalent to the nematode ced-3 gene function in a variety of organisms. The structural similarity between their gene products suggests that the ICE gene is a human equivalent of the ced-3 cell death gene. As further described below, the conservation of certain features of ICE in the Ced-3 protein further suggests that Ced-3 is a protease with a substrate-specificity similar to that of ICE.

Furthermore, the identification of ced-3 and ICE as structurally related genes (i.e., genes whose encoded products, or which themselves, are structurally similar) presents the possibility that a family of structurally related genes exists and provides probes to identify additional members of this ced-3/ICE gene family. Comparison of the genes within this family could indicate functionally important features of the genes or their gene products, and thus, provide information for designing drugs which are useful for treating conditions characterized by cell deaths and/or inflammatory disease.

This discovery provides novel drugs based on the ced-3, ICE and other ced-3/ICE genes and encoded products that inhibit the production of IL-1β and are useful for treatment (preventive and therapeutic) of acute and chronic inflammatory disease, as well as drugs which reduce cell deaths and are useful for treatment of diseases and conditions involving cell deaths (such as myocardial infarction, stroke, traumatic brain injury, viral and other types of pathogenic infection, degenerative diseases, aging, and hair loss). These drugs may also be useful for treating leukemias in which IL-1β has been implicated.

Drugs or agents which increase cell deaths can also be developed based on the ced-3, ICE, and related genes and gene products; such drugs or agents may be useful for killing or incapacitating undesired cell populations (such as cancerous cells, infected cells, cells which produce autoreactive antibodies and hair follicle cells) or undesired organisms (such as pests, parasites, and genetically engineered organisms). Drugs are also provided which increase IL-1β production and, therefore, the inflammatory and immune response. These drugs may be helpful for providing increased resistance to viral and other types of infection.

Also described herein is the discovery that fusion constructs containing amino-terminal portions of the ced-3 gene can inhibit the activity of the intact gene when expressed in otherwise wild-type worms. Due to the similarity between ICE and Ced-3, it is likely that the corresponding amino-terminal portions of the ICE gene will also inhibit the enzymatic activity of ICE in cleaving interleukin-1β. Thus, novel inhibitors of the ced-3 and ICE genes are provided which may be useful for decreasing cell deaths and/or inflammation involved in various pathologies.

This work has also shown that Ced-3 and the murine NEDD-2 protein are structurally similar. Thus, drugs for increasing or decreasing cell deaths can be developed based on the NEDD-2 gene and its encoded products.

The above-described discoveries, and their implications, and novel drugs and treatments for diseases related to cell death and/or inflammation arising therefrom are described in further detail below.

As used herein, the activity of a gene is intended to include the activity of the gene itself and of the encoded products of the gene. Thus, drugs and mutations which affect the activity of a gene include those which affect the expression as well as the function of the encoded RNA and protein. The drugs may interact with the gene or with the RNA or protein encoded by the gene, or may exert their effect more indirectly.

It is understood that many of the methods used herein may be utilized in a therapeutic context. Where the therapeutic compound is DNA it is understood that method known in the art of gene therapy may be employed for therapeutic drug delivery. For example, in vivo or ex vivo methods may be used to provide DNA encoding therapeutic peptides which prevent cell death to organs and tissues used for transplantation. Similarly, such techniques may be used to administer nucleic acid to a patient suffering a cell death disease. Where peptide and peptide mimetics are to be employed standard techniques known in the pharmaceutical art may be used to determine the most effective dosage and route of delivery.

The ced-3 Gene

Figure 2:
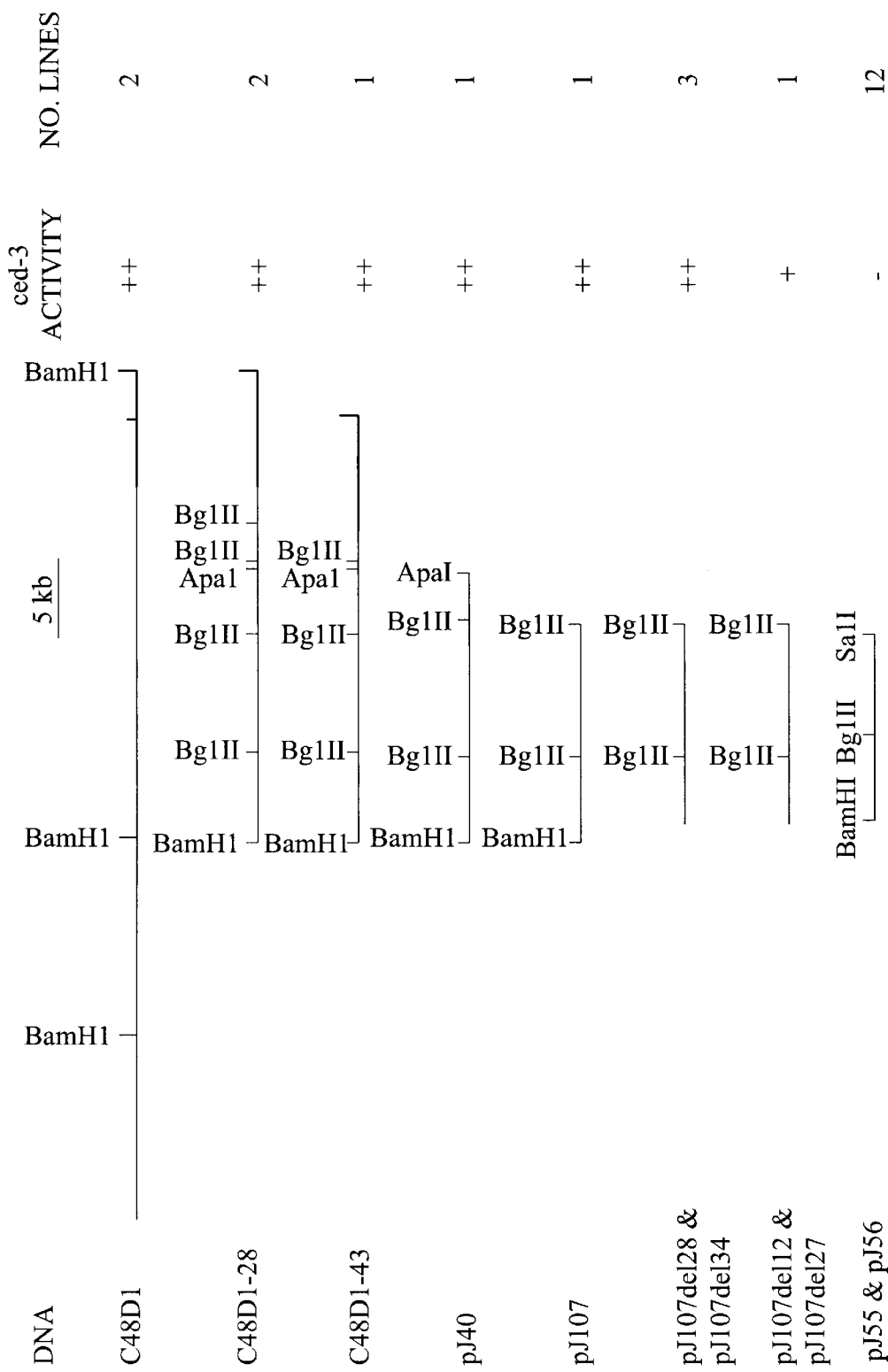
FIG. 2 summarizes the experiments to localize ced-3 within C48D1. Restriction sites of plasmid C48D1 and subclone plasmids are shown. Ced-3 activity was scored as the number of cell corpses in the head of L1 young animals. ++, the number of cell corpses above 10. +, the number of cell corpses below 10 but above 2. –, the number of cell corpses below 2.

The C. elegans ced-3 gene was cloned by mapping DNA restriction fragment length polymorphisms (RFLPs) and chromosome walking (Example 1; FIG. 1). The gene was localized to a 7.5 kb fragment of cloned genomic DNA by complementation of the ced-3 mutant phenotype (FIG. 2). A 2.8 kb transcript was further identified. The ced-3 transcript was found to be most abundant in embryos, but was also detected in larvae and young adults, suggesting that ced-3 is expressed not only in cells undergoing programmed cell death.

A 2.5 kb cDNA corresponding to the ced-3 mRNA was sequenced. The genomic sequence cloned in the plasmid pJ107 was also determined (FIG. 3; SEQ ID NO: 1). A comparison with the cDNA sequence revealed that the ced-3 gene has 7 introns which range in size from 54 to 1195 bp (FIG. 4A). The four largest introns, as well as sequences 5' of the start codon, contain repetitive elements (FIG. 3), some of which have been previously characterized in non-coding regions of other C. elegans genes such as fem-1 (Spence et al., Cell 60:981–990 (1990)), lin-12, and myoD (Krause et al., Cell 63:907–919 (1990)). The transcriptional start site was also mapped (FIG. 3), and a ced-3 transcript was found to be trans-spliced to a C. elegans splice leader, SL1.

Twelve EMS-induced ced-3 alleles were also sequenced. Eight of the mutations are missense mutations, three are nonsense mutations, and one is a putative splicing mutation (Table 1). This identification of ced-3 null alleles, together with results of genetic analysis of nematodes homozygous for these null mutations in ced-3, indicate that, like ced-4, ced-3 function is not essential to viability. In addition, 10 out of the 12 mutations are clustered in the carboxyl-terminal region of the gene (exons 6–8, FIG. 4B), suggesting that this portion of the encoded protein may be important for activity.

The ced-3 gene encodes a putative protein of 503 amino acids (FIG. 3; SEQ ID NO: 2). The protein is very hydrophilic and no significantly hydrophobic region can be found that might be a transmembrane domain (FIG. 5). One region of the Ced-3 protein is very rich in serine (FIG. 6A). Comparison of the C. elegans protein with the Ced-3 proteins of two related nematodes species, C. briggsae and C. vulgaris, shows conservation of the serine-rich feature without conservation of the amino acid sequence in this region (FIG. 7; SEQ ID NOS: 5 and 6). This suggests that the exact sequence of this serine-rich region may not be important but that the serine-rich feature is. This hypothesis is supported by analysis of ced-3 mutations: none of 12 EMS-induced ced-3 mutations is in the serine-rich region (FIG. 4B). It is possible that the serine-rich region in Ced-3 is another example of semi-specific protein-protein interaction, similar to acid blobs in transcription factors and basic residues in nuclear localization signals. In all these cases, the exact primary sequence is not important.

The serine-rich region may function as a site for post-translational regulation of Ced-3 activity through protein phosphorylation of the serine residues by a Ser/Thr kinase. McConkey et al. (J. Immunol. 145:1227–1230 (1990)) have shown that phorbol esters, which stimulate protein kinase C, can block the death of cultured thymocytes induced by exposure to $Ca^{++}$ ionophores or glucocorticoids (Wyllie, Nature 284:555–556 (1980); Wyllie et al., J. Path. 142:67–77 (1984)). It is possible that protein kinase C may inactivate certain cell death proteins by phosphorylation and, thus, inhibit cell death and promote cell proliferation. Several agents that can elevate cytosolic cAMP levels have been shown to induce thymocyte death, suggesting that protein kinase A may also play a role in mediating thymocyte death. Further evidence suggests that abnormal phosphorylation may play a role in the pathogenesis of certain cell-degenerative diseases. For example, abnormal phosphorylation of the microtubule-associated protein Tau is found in the brains of Alzheimer's disease and Down's syndrome patients (Grundke-Iqbal et al., Proc. Natl. Acad. Sci. USA 63:4913–4917 (1986); Flament et al., Brain Res. 516:15–19 (1990)). Thus, it is possible that phosphorylation may have a role in regulating programmed cell death in C. elegans. This is consistent with the fairly high levels of ced-3 and ced-4 transcripts which suggest that transcriptional regulation alone may be insufficient to regulate programmed cell death.

Structural Relatedness of the ced-3 and Human Interleukin-1β Convertase Genes and Functional Implications A search of GenBank, PIR and SWISS-PROT databases using the Blast program (National Center for Biotechnology Information) revealed that human interleukin-1β convertase (ICE) has a 28% amino acid identity with the Ced-3 protein (FIG. 6A). A comparable level of overall similarity was found between ICE and the Ced-3 proteins from two other nematode species, C. briggsae and C. vulgaris.

The carboxyl-terminal regions of Ced-3 and ICE (amino acids 250–503 and amino acids 166–404, respectively) were found to be more conserved (33% identity) than the amino-terminal portions of the two proteins (22% identity). A comparison of human and murine ICEs also indicated a high degree of similarity (80% identity) in the carboxyl-terminal region compared with an overall identity of 62% (Cerretti et al., Science 256:97–100 (1992)). Furthermore, deletion analysis of the ICE cDNA sequence has shown that the amino-terminal 119 amino acids of ICE are not required for enzymatic activity, but that deletions of the carboxyl-terminal region eliminate the enzyme's ability to process pro-IL-1β (Cerretti et al., 1992 supra). The observation that most of the inactivating mutations of ced-3 cluster in the carboxyl-terminal region (FIG. 4B) suggests that the activity of Ced-3 also resides (at least partially) in this region. Thus, the identification of the carboxyl-terminal regions of the two proteins as functional domains and the marked similarity of these regions suggest that the Ced-3 and ICE proteins have similar activities, i.e., that ICE has cell death activity similar to Ced-3 and Ced-3 has protease activity similar to ICE.

The possiblity that Ced-3 has protease activity is further supported by the observation that the region surrounding the active cysteine and two autocleavage sites of ICE appear to be conserved in the Ced-3 protein. As shown in FIG. 6A, the five amino acids (QACRG, amino acids 283 to 287) surrounding the active cysteine of ICE (Thornberry et al.,

*Nature* 356:768–774 (1992)) are conserved in amino acids 356 to 360 of Ced-3; this pentapeptide is the longest conserved sequence between ICE and Ced-3. This peptide is also conserved in the Ced-3 proteins of *C. briggsae* and *C. vulgaris* (FIG. 7). One inactivating mutation of ced-3, n2433, introduces a glycine to serine change near the putative active cysteine (FIG. 6A). Example 3 demonstrates that mutations of the active cysteine decrease cell death. Accordingly, one may predict that mutation of the active cysteine in ICE (Cys 285) will yield a therapeutic which decreases cell death.

The human ICE gene encodes a precursor enzyme which is autoproteolytically cleaved at two major sites (amino acids 103 and 297) by the active form of the enzyme (Thornberry et al., 1992 supra). The Asp-Ser dipeptides of both autocleavage sites are conserved in Ced-3 (at amino acids 131 and 371) (FIG. 6A). The conservation of these functionally important sequences strongly suggests that, like ICE, Ced-3 is a cysteine protease with a similar substrate-specificity. Ced-3 would, therefore, be expected to cleave the IL-1β precursor, as well as other substrates of ICE.

The possibility that ICE is a cell death gene is consistent with evidence which suggests that the production of active IL-1β is involved with cell death processes. Firstly, a variety of studies has suggested that IL-1β can prevent cell death (McConkey et al., *J. Biol. Chem.* 265:3009–3011 (1990); Mangan et al., *J. Immun.* 146:1541–1546 (1991); Sakai et al., *J. Exp. Med.* 166:1597–1602 (1987); Cozzolino et al., *Proc. Natl. Acad. Sci. USA* 86:2369–2373 (1989)). Secondly, active, mature IL-1β appears to be released from cells undergoing cell death. Studies on murine macrophages suggest that release of the active form seems not to be merely due to the lysis of the cells or leaking of cell contents. When murine peritoneal macrophages were stimulated with lipopolysaccharide (LPS) and induced to undergo cell death by exposure to extracellular ATP, mature active IL-1β was released into the culture supernatant. In contrast, when the cells were injured by scraping, IL-1β was released exclusively as the inactive proform (Hogquist et al., *Proc. Natl. Acad. Sci. USA* 88:8485–8489 (1991)).

The similarity between ICE and Ced-3 strongly supports the hypothesis that ICE is involved in cell death. Since Ced-3 is necessary for cell death, one suggestion is that ICE is also necessary for cell death. It is possible that IL-1β can cause cell death. Alternatively, ICE could produce products besides IL-1β, one or more of which can cause cell death. The observation that the ICE transcript is detected in cells that lack IL-1β expression (Cerretti et al., 1992 supra) supports this idea. Example 4 demonstrates that known inhibitors of ICE may be administered to prevent cell death in mammals, particularly motor neuron cell death.

The finding of a human gene related to the nematode ced-3 gene is consistent with the idea that cell death genes which are structurally related and/or functionally similar to the nematode ced-3 gene exist in a variety of organisms. This idea is supported by evidence that cell deaths occurring in a variety of organisms, including vertebrates and invertebrates, and possibly microbes and plants, as well as cell deaths observed in various developmental and pathologic situations share a common genetic mechanism. Evidence for this hypothesis is discussed in Example 2. The structural relatedness of ICE suggests that it is a mammalian equivalent of the nematode cell death gene, ced-3. The cDNA sequence of ICE is shown in FIG. 8 (SEQ ID NO: 3).

The ced-3/ICE Gene Family and Uses Thereof

The ICE and ced-3 genes can be used to isolate additional structurally related genes, including genes from other organisms. Such genes may be identified using probes derived from both the ced-3 and ICE gene sequences and known techniques, including nucleic acid hybridization, polymerase chain reaction amplification of DNA, screening of cDNA or genomic libraries, and antibody screening of expression libraries. The probes can be all or portions of the genes which are specific to the genes, RNA encoded by the genes, degenerate oligonucleotides derived from the sequences of the encoded proteins, and antibodies directed against the encoded proteins. The sequences of the genes and their protein products can also be used to screen DNA and protein databases for structurally similar genes or proteins.

One strategy for detecting structurally related genes in a number of organisms is to initially probe animals which are taxonomically closely related to the source of the probes, for example, probing other worms with a ced-3-derived probe, or probing other mammals with an ICE-derived probe. Closely related species are more likely to possess related genes or gene products which are detected with the probe than more distantly related organisms. Sequences conserved between ced-3 or ICE and these new genes can then be used to identify similar genes from less closely related species. Furthermore, these new genes provide additional sequences with which to probe the molecules of other animals, some of which may share conserved regions with the new genes or gene products but not with the original probe. This strategy of using structurally related genes in taxonomically closer organisms as stepping stones to genes in more distantly related organisms can be referred to as walking along the taxonomic tree.

Together, ced-3, ICE, and related genes obtained as described above would comprise a family of structurally related genes, referred to herein as the ced-3/ICE gene family. It is highly likely that at least some of these additional family members would exhibit cell death and/or protease activity. The new genes can be tested for protease activity using known assay methods. For example, the sequence of the protein encoded by a new gene may indicate an active site and substrate-specificity similar to that of ICE, such as observed in Ced-3. This activity can then be verified using the transient expression assays and purified enzyme assays previously described (Cerretti et al., *Science* 256:97–100 (1992); Thornberry et al., *Nature* 356:768–774 (1992)). Cell death activity can be tested in bioassays using transgenic nematodes. A candidate cell death gene, such as the ICE gene, can be injected into Ced-3-deficient mutant animals to determine whether the gene complements the ced-3 mutation. Expression libraries can also be screened for cell death genes by this assay.

The ced-3, ICE and other related genes which have cell death activity can be used to develop and identify drugs which reduce or increase cell deaths. Drugs which reduce cell deaths are potentially useful for treating diseases and conditions characterized by cell deaths, such as myocardial infarction, stroke, viral and other pathogenic infections (e.g., human immunodeficiency virus), traumatic brain injury, neural and muscular degenerative diseases, and aging. Drugs which cause cell deaths can be used to control or reduce undesired cell populations, such as neoplastic growths and other cancerous cells, infected cells, and cells which produce autoreactive antibodies. Undesired organisms, such as pests, parasites, and recombinant organisms, may also be incapacitated or killed by such drugs.

ICE has been implicated in the growth of certain leukemias (Sakai et al., *J. Exp. Med.* 166:1597 (1987); Cozzolino et al., *Proc. Natl. Acad. Sci. U.S.A.* 86:2369 (1989); Estrov et al., *Blood* 78:1476 (1991); Bradbury et al., *Leukemia* 4:44 (1990); Delwel et al., *Blood* 74:586 (1989); Rambaldi et al., *Blood* 78:3248 (1991)). The observation that the human ICE gene maps to chromosome location 11q23, a site frequently involved in DNA rearrangements seen in human cancers (C. Cerretti et al., *Science* 256: 97–100 (1992)), further suggests that ICE is involved in cancer. The finding that ICE probably functions in cell death implies that ICE and other related genes, like ced-3, may be used to develop drugs to control cancerous growth.

In addition, since cell death plays an important role in mammalian hair growth, it seems likely that by controlling cell death, one could cause or prevent hair loss. It has been found that bcl-2, a human gene which is structurally related to the gene which prevents cell deaths in nematode development (ced-9), is expressed in the hair follicle in a cell-cycle dependent manner. ced-9 has been shown to act by antagonizing the activities of the cell death genes, ced-3 and ced-4. Together, these findings suggest that genes equivalent to the ced-3, ced-4, and ced-9 genes are involved in the physiology of mammalian hair growth and loss.

Drugs which increase cell deaths may comprise ced-3, ICE, and other ced-3/ICE family members, their RNA and protein products, constitutively activated mutants of the genes and encoded products, and peptide and non-peptide mimetics of the proteins. Drugs which decrease cell deaths may comprise antisense RNA complementary to the mRNA of a cell death gene, or mutant cell death genes or encoded products, that no longer cause cell death and interfere with the function of wild-type genes. Furthermore, drugs comprising agonists and antagonists of the cell death genes can be designed or identified using the genes or their gene products as targets in bioassays. The bioassays can be conducted in wild-type, mutant, or transgenic nematodes, in which an alteration in programmed cell deaths is an indicator of an effective agonist or antagonist. Bioassays can also be performed in cultured cells transfected with the target cell death gene, into which the substance being tested is introduced. In bioassays for antagonists of cell death, the cultured cells should be put under conditions which induce the activity of the target cell death gene.

Uses of bioassays utilizing *C. elegans* are exemplified by the following:

1) use of normal, wild-type nematodes to screen for drugs or genes that inactivate ced-3 and hence, prevent programmed cell deaths;
2) use of normal, wild-type nematodes to screen for drugs or genes that activate ced-3 and hence, cause excess cell deaths;
3) use of mutant nematodes which overexpress ced-3 or which express a constitutively activated ced-3 gene to identify drugs or genes that prevent excess cell deaths caused by the ced-3 mutation;
4) use of mutant nematodes which underexpress ced-3 or which express an inactivated ced-3 gene to identify drugs or genes that mimic or complement the ced-3 mutation;
5) use of transgenic nematodes (with an inactivated endogenous ced-3 gene) in which either a wild-type or mutant form of ICE or other ced-3/ICE family member causes excess cell deaths to identify drugs or genes which antagonize the activity of the transgene; and
6) use of transgenic nematodes which carry a transgene that inhibits cell death (e.g., a transgene that expresses an inhibitory fragment of ced-3, ICE or related gene, as described below) to identify drugs that overcome this inhibition and cause cell death.

Drugs can be introduced into nematodes by diffusion, ingestion, microinjection, shooting with a particle gun or other methods. They can be obtained from traditional sources such as extracts (e.g., bacterial, fungal or plant) and compound libraries, or can be provided by newer methods of rationale drug design. Information on functionally important regions of the genes or gene products, gained by sequence comparisons and/or mutational analysis may provide a basis for drug design. Genes can be microinjected into nematodes to produce transgenic nematodes. Individual genes or cDNA and genomic DNA libraries can be screened in this manner.

Agonists and antagonists may also be derived from genes which are not cell death genes, but which interact with, regulate or bypass cell death genes. Such interacting genes may be tested by the bioassays mentioned above, as well as by in vivo genetics in nematodes. In this latter method, interacting genes are identified as secondary mutations which suppress or enhance the ced-3 mutation. The sequences of these interacting genes can then be used to identify structurally related interacting genes in other organisms.

Similarly, anti-inflammatory drugs may be developed or identified using ced-3, ICE and other family members and their encoded products. Drugs which enhance ICE activity may also be useful for boosting the inflammatory response to viral and other infections.

In addition, the availability of a number of structurally related genes makes it possible to carry out structural comparisons. Conserved regions or features of the genes or their encoded products are likely to be functionally significant for cell death and/or protease activity. This information could be helpful in designing or selecting drugs which would mimic or affect the activity of the genes.

Moreover, conservation of functional domains among ced-3/ICE family members or their encoded products suggests not only that these genes have similar activities, but that they and their encoded products function via similar mechanisms. This suggests that mutations in conserved regions, mimetics based on conserved regions, and agonists and antagonists which affect the function of conserved regions of one ced-3/ICE gene or encoded protein will similarly affect other genes or encoded proteins in the family. This is the rationale behind the use of Ced-3 inhibitors to inhibit ICE and inflammation, and the use of anti-inflammatory drugs which act by inhibiting ICE to inhibit the ced-3 gene and reduce cell deaths (described further below).

Furthermore, drugs which affect the cell death and/or inflammatory activities of the ced-3 and ICE genes may also affect other as yet undiscovered activities of these genes. The biology of IL-1β and ICE is only incompletely understood at the present time, and it is very likely that other functions of both IL-1β and ICE may be discovered. These may include new activities or new physiological processes or diseases in which the respective cytokinetic and proteolytic activities of these molecules are involved. In either case, drugs (such as inhibitory protein portions) which affect ICE activity are likely to affect the new activities and processes, as well.

In addition, mutations and drugs which alter or mimic the activity of one member of the ced-3/ICE family can be engineered based on what is known about mutations and drugs affecting another family member with which it shares a conserved region. Mutations in conserved regions which correspond to those found in another family member could be used to produce similar effects. For example, five out of nine inactivating point mutations analyzed in ced-3 were found to result in alterations of amino acids which are conserved between ICE and Ced-3 (FIG. 6A). Amino acid substitutions in ICE corresponding to those in Ced-3 are also expected to result in inactivation (see Example 3). The inhibitory amino-terminal gene portions and constitutively activated carboxyl-terminal gene portions described below are further examples of corresponding mutations which can be made in genes of the ced-3/ICE family.

Comparison of Ced-3, ICE, and related proteins also provides insights into the substrate-specificity of ICE and related enzymes. Previous studies on ICE have not identified a consistent consensus cleavage site. A comparison of the Ced-3 and ICE autocleavage sites, together with the cleavage site of pro-IL-1β, reveals that cleavage always occurs after an Asp residue. For this reason, it is likely that Ced-3, ICE, and related proteins are proteases which cleave after some aspartate residues or, perhaps at lower efficiencies, all aspartate residues.

A further use of ced-3/ICE family members is to provide diagnostic probes (DNA, RNA, oligonucleotides and antibodies) for diseases involving cell deaths and inflammation in humans and other organisms. It is likely that such diseases are associated with abnormalities in ced-3/ICE genes and their gene products. The probes can be used to detect abnormalities in the sequence, level and/or activities of the genes and encoded RNA and protein products. The diseases may be genetic, in which case, the probes may be used in patient and pre-natal testing, or non-genetic, in which case, RNAs and proteins may be examined. In particular, the finding that ICE is a putative cell death gene makes this gene and its derivative molecules potentially useful as diagnostic probes for diseases characterized by cell deaths. Similarly, ced-3 and its derivative molecules are potentially useful for detecting abnormalities in pathologies in which inflammation is evident. The usefulness of these probes may be multiplied as more genes with known physiological functions are found to be structurally related to ced-3 and ICE.

Structural Relatedness of ced-3 and the Murine NEDD-2 Gene

Database searches also revealed that another mammalian protein is similar to the Ced-3 protein (FIG. 6B). The murine NEDD-2 (lch-1) protein has 27% amino acid identity and 55% similarity to a carboxyl-terminal portion of Ced-3. The NEDD-2 protein is expressed in the brain of mouse embryos and much less in the murine adult brain; the protein is thought to be involved in the development of the murine central nervous system (Kumar et al., Biochem. Biophys. Res. Comm. 185(3):1155–1161 (1992)). The structural similarity between the NEDD-2 and ced-3 gene products suggests that the NEDD-2 gene is also involved in cell death processes which occur during development, and further supports the hypothesis that genes which are structurally and functionally related to the nematode ced-3 gene function in a variety of organisms. Interestingly, the NEDD-2 amino acid sequence is not significantly similar to that of human ICE.

The similarity of the amino acid sequences of Ced-3 and NEDD-2 further suggests that mutations of the NEDD-2 gene which produce alterations in the protein corresponding to alterations in Ced-3 resulting from the mutations, n1129, n1164, n2426 and n1163 (see FIG. 6B), will inactivate the NEDD-2 gene.

This invention includes all and portions of the NEDD-2 gene, mutated NEDD-2 genes corresponding to known ced-3 mutations, RNAs and proteins encoded by the wild-type and mutated genes, and mimetics and other drugs derived from these genes and gene products, which are useful for controlling cell death.

FIGS. 6C and 6D show alignments of the amino-terminal and carboxyl-terminal regions, respectively, of the Ced-3 proteins of the three nematode species (C. briggsae, C. elegans, and C. vulgaris), the human and murine ICEs and the murine NEDD-2 protein (in 6D only). As shown in these figures (boxed portions), a number of amino acids are completely conserved among these structurally related proteins, and thus, are likely to be important functionally. Mutations of these sites would be expected to alter the activity of the genes.

Inhibitory Portions of the ced-3 Gene

Fusion constructs containing portions of the ced-3 gene were found to prevent programmed cell death when expressed in wild-type C. elegans. These constructs are represented schematically in FIG. 9A. The BGAFQ construct contains a portion of the ced-3 gene fused 5' of the E. coli lacZ gene and another ced-3 portion fused 3' of lacZ. The 5' ced-3 portion is the genomic sequence from a BamHI site located about 300 base pairs upstream of nucleotide 1 of the sequence shown in FIG. 3 to a SalI site at nucleotide 5850. This portion spans sequences 5' of the SL1 acceptor site (nucleotide 2161) to include the 372 codons of the amino-terminal region. The 3' ced-3 portion of BGAFQ is the genomic sequence from a NotI site at nucleotide 5927 in the ced-3 gene to an ApaI site located about 1.5 kb downstream of nucleotide 7653 of the sequence in FIG. 3. This portion contains the carboxyl-terminal codons from 398 to the end (codon 503) and 3' untranslated sequences.

The PBA construct has a smaller portion of the ced-3 gene which is the genomic sequence from the same BamHI site as in BGAFQ to a BglII site at nucleotide 3020 (FIG. 9A) fused 5' of the lacZ gene. This ced-3 portion spans sequences 5' of the SL1 acceptor site to include the first 149 codons of the amino-terminal region.

Both constructs were made using the pBluescript vector (Stratagene) and fragments containing the lacZ construct from the pPD vectors of Fire (EMBO J. 5:2673–2690 (1986)). The lacZ-containing portion has the entire lacZ coding sequence except for the first 11 codons. In addition, there is a synthetic intron and a nuclear localization signal upstream of the lacZ gene and a fragment of the 3' end of the unc-54 gene downstream of the lacZ gene (FIG. 9B). Construct PBA was made by inserting a BamHI-ApaI fragment containing the lacZ construct shown in FIG. 9B from Andy Fire's vector, pPD22.04, into the BglII-ApaI fragment of the ced-3-containing plasmid, pJ40. Construct BGAFQ was made by inserting a SalI-EagI fragment containing the same lacZ construct from pPD22.04 into the SalI-NotI fragment of pJ40A, which is pJ40 without the NotI site in the vector.

Table 2 shows the results of injecting wild-type nematodes with the two constructs. These results indicate that the BGAFQ and PBA fusion constructs prevent cell deaths which normally occur in the development of the nematodes. These fusion constructs were further observed to prevent cell deaths and the apparently associated inviability caused by a loss-of-function mutation in ced-9, a gene which functions to keep certain cells from dying during nematode development, and which has been shown to act by antagonizing ced-3 and second cell death gene, ced-4.

Both constructs express β-galactosidase activity in wild-type nematodes. Since the pBluescript vector does not contain eukaryotic transcriptional or translational start sites, these signals are probably supplied by the ced-3 gene portions fused 5' of lacZ. Furthermore, since the PBA construct works to prevent cell death, it seems that the ced-3 portion in BGAFQ needed for inhibition is the portion fused upstream of lacZ (as opposed to the portion located downstream of lacZ). Presumably, only the region from the BamHI site to nucleotide 3020 is needed in BFAGQ, since this is all that is contained in PBA.

A construct that contains the PBA ced-3 portion but not any of the lacZ portion did not prevent cell death, suggesting that fusion to portions of lacZ is needed for expression or action of the inhibitory gene portion.

These observations indicate that the amino-terminal portion of the Ced-3 protein, possibly in conjunction with a portion of E. coli β-galactosidase, can act to prevent programmed cell deaths in C. elegans. One plausible mechanism is that this portion of the Ced-3 protein acts in a dominant negative or antimorphic fashion, to prevent the activity of the normal Ced-3 protein. (It is known that inactivation of the Ced-3 protein results in an absence of programmed cell deaths.) Such dominant negative activity could be a result of the partial Ced-3 protein binding to and, thereby, inactivating the normal Ced-3 protein; consistent with this model is the finding that the active form of the structurally similar ICE protein is dimeric. Alternatively, the partial Ced-3 protein may bind to a molecule with which the normal Ced-3 protein must interact to function and by preventing this interaction, inhibits Ced-3 activity.

Due to the structural similarity of ICE to the Ced-3 protein, fusion constructs encoding amino-terminal portions of ICE would also be expected to inhibit the activity of the ced-3 gene. In particular, those portions of the ICE gene corresponding to the ced-3 gene portions in BGAFQ and PBA, i.e., ICE codons 1 to 298 and codons 1 to 111, or active subportions of these, are expected to inhibit ced-3. A further extension of this reasoning suggests that corresponding gene portions of any structurally related ced-3/ICE family member would also have an inhibitory effect on ced-3 activity.

Furthermore, the structural relatedness of the ced-3 and ICE genes implies that the ICE enzyme could also be inhibited by fusion constructs containing amino-terminal portions of the ICE gene, as well as corresponding portions of other structurally related genes, such as ced-3.

Identification of portions of the ced-3, ICE, and related genes which inhibit the ced-3 gene can be carried out by testing expression constructs containing these gene portions or their encoded products in bioassays for cell death activity. Identification of gene portions or encoded products which inhibit ICE can be carried out using previously described assays for ICE activity. For example: 1) wild-type worms can be injected with portions of the ced-3 or other structurally related gene, such as ICE, to determine if they prevent programmed cell death; 2) portions of the ICE protein or other structurally similar protein, such as Ced-3, can be co-expressed with ICE and pro-IL-1β in nematodes or cultured mammalian cells to see if they inhibit ICE-catalyzed cleavage of the IL-1β precursor; and 3) peptides or nucleic acids containing portions of the amino acid or coding sequence of ICE or similar protein, such as Ced-3, can be tested using purified ICE and synthetic substrates.

Inhibitory portions of the ced-3 gene, ICE, and structurally related genes, their encoded RNAs and proteins, and peptide and non-peptide mimetics of the proteins may be used to reduce cell deaths and/or inflammation, and are, thus, useful for the treatment of diseases involving these processes. The encoded proteins and peptide and non-peptide mimetics can be delivered by various known methods and routes of drug delivery. For example, they can be administered orally or by another parenteral route or by a non-parenteral route (e.g., by injection intramuscularly, intraperitoneally or intravenously or by topical administration). Alternatively, expression constructs containing the gene portions can be made using heterologous transcriptional and translational signals or signals native to the gene portions. The constructs can be delivered into cells by various methods of gene therapy, such as retroviral infection. These constructs (and any other constructs which encode activity decrease cell death) may be used for example, to prevent localized cell death at the site of organ and tissue transplantation.

Interestingly, those ICE gene portions corresponding to the ced-3 portions of BGAFQ and PBA encode approximately the protein fragments which result from cleavage at each of the two autocleavage sites (amino acids 103 and 297). This observation suggests that autoproteolytic conversion of the proenzyme to active ICE involves cleaving off the inhibitory amino-terminal portions of the protein. Active ICE is a heterodimer composed of subunits of about 20 and 10 kilodaltons (Thornberry et al., Nature 356:768–774 (1992)). These subunits have been shown to be derived from the ICE proenzyme and correspond to amino acids 120 to 297 (p20) and 317 to 404 (p10). Kinetic studies suggest that association of the two subunits is required for activity of the enzyme. It is possible that the amino-terminal region of the protein interferes with this association.

This implies that mutant proteins in which the inhibitory amino-terminal regions are deleted may be constitutively activated. Thus, carboxyl-terminal portions of the Ced-3, ICE, and related proteins, and constructs and RNAs expressing these portions, are potentially useful for increasing cell deaths and/or IL-1β production. Constructs which may be used include those which express the carboxyl region of ICE, which encodes the two subunits of the active enzyme, as well as those which express each of these subunits separately. In addition, it is possible that the amino region of ICE, which is not needed for ICE enzymatic activity in vitro, is important for ICE activity or the regulation of ICE activity in vivo. Consistent with this idea is the finding that two of the ced-3 mutations map in this region. For this reason, a construct which expresses the amino region of Ced-3, ICE or a Ced-3/ICE gene family member may also be used. Furthermore, the NEDD-2 protein, which is similar to a carboxyl-terminal portion of the Ced-3 portion, may also exhibit constitutive activity in causing cell deaths. Thus, all or active portions of NEDD-2, and DNA and RNA encoding NEDD-2 proteins, would be expected to produce cell death activity when expressed. Drugs comprising activated molecules derived from the carboxyl-terminal regions of Ced-3, ICE and other proteins of the Ced-3/ICE family and from the NEDD-2 protein, DNAs and RNAs encoding these proteins and protein fragments, as well as peptide and non-peptide mimetics, are potentially useful for controlling or reducing the size of undesirable cell populations, such as cancerous cells, infected cells, cells producing autoreactive antibodies and hair follicle cells. Such drugs may also be useful for incapacitating or killing undesired organisms, such as parasites, pests, and genetically engineered organisms. For example, a number of nematodes are human, animal and plant parasites.

ICE Inhibitors As Inhibitors of Cell Death

The conservation of the active site of ICE (active cysteine and surrounding amino acids) in the Ced-3 protein implies that Ced-3 is a cysteine protease which interacts with its substrate by a similar mechanism. Hence, it is likely that inhibitors of ICE which interfere with this mechanism, or chemical analogs of these inhibitors, will inhibit Ced-3 function and inhibit cell death resulting from ICE activity.

Peptide aldehydes containing the ICE recognition site:

P4--P3--P2--P1

Tyr-Val-Ala-Asp or a substituted site in which P2 is Ala, His, Gln, Lys, Phe, Cha, or Asp, have been shown to be effective, specific, and reversible inhibitors of the protease activity of ICE (Thornberry et al., Nature 356:768–774 (1992)). These molecules are thought to act as transition analogs, which compete for ICE binding to its substrate, pro-IL-1β. Three such inhibitors have been described: Inhibitor B (Ac-Tyr-Val-Ala-Asp-CHO); Inhibitor C (Ac-Tyr-D-Ala-Ala-Asp-CHO); and Inhibitor D (Ac-Tyr-Val-Lys-Asp-CHO). Of these, Inhibitor B is the most potent, with a $K_i$=0.76 nM compared to $K_i$=3 nM for D and $K_i$=1.5 μM for C. Example 4 provides evidence that these inhibitors may be used to prevent cell deaths in mammals.

In addition, the crmA gene of cowpox virus has been found to encode a serpin which specifically inhibits ICE (Ray et al., Cell 69:597–604 (1992)). The serpin acts by preventing the proteolytic activation of ICE. This inhibitor of ICE is also expected to inhibit structurally similar proteins, such as Ced-3. The crmA gene and methods for obtaining purified CrmA protein have been described (Pickup et al., Proc. Natl. Acad. Sci. USA 83:7698–7702 (1986); Ray et al., 1992 supra). This invention includes the use of inhibitors of ICE, such as peptide aldehydes, and particularly inhibitor B, and the CrmA protein, as drugs for decreasing the activity of cell death genes and, thus, for treatment of diseases characterized by cell deaths.

The following examples illustrate the invention and are not intended to be limiting in any way.

EXAMPLE 1

CLONING, SEQUENCING, AND CHARACTERIZATION OF THE CED-3 GENE

Materials and Methods

General Methods and Strains

The techniques used for the culturing of C. elegans were as described by Brenner (Genetics 77:71–94 (1974)). All strains were grown at 20° C. The wild-type parent strains were C. elegans variety Bristol strain N2, Bergerac strain EM1002 (Emmons et al., Cell 32:55–65 (1983)), C. briggsae and C. vulgaris (obtained from V. Ambros). The genetic markers used are described below. These markers have been described by Brenner (1974 supra), and Hodgkin et al. (In: The Nematode Caenorhabditis elegans, Wood and the Community of C. elegans Researchers (eds.), Cold Spring Harbor Laboratory, 1988, pp 491–584). Genetic nomenclature follows the standard system (Horvitz et al., Mol. Gen. Genet. 175:129–133 (1979)):

LG I: ced-1(e1375); unc-54(r323)

LG VI: unc-31(e928), unc-30(e191), ced-3(n717, n718, n1040, n1129, n1163, n1164, n1165, n1286, n1949, n2426, n2430, n2433), unc-26(e205), dpy-4(e1166)

LG V: egl-1(n986); unc-76(e911)

LG X: dpy-3(e27)

Isolation of Additional Alleles of ced-3

A non-complementation screen was designed to isolate new alleles of ced-3. Because animals heterozygous for ced-3(n717) in trans to a deficiency are viable (Ellis and Horvitz, Cell 44:817–829 (1986)), animals carrying a complete loss-of-function ced-3 allele generated by mutagenesis were expected to be viable in trans to ced-3(n717), even if the new allele was inviable in homozygotes. Fourteen EMS mutagenized egl-1 males were mated with ced-3 (n717) unc-26(e205); egl-1(n487); dpy-3(e27) hermaphrodites. egl-1 was used as a marker in this screen. Dominant mutations in egl-1 cause the two hermaphrodite specific neurons, the HSNs, to undergo programmed cell death (Trent et al., Genetics 104:619–647 (1983)). The HSNs are required for normal egg-laying, and egl-1(n986) hermaphrodites, which lack HSNS, are egg-laying defective (Trent et al., 1983 supra). The mutant phenotype of egl-1 is suppressed in a ced-3; egl-1 strain because mutations in ced-3 block programmed cell deaths. egl-1 males were mutagenized with EMS and crossed with ced-3(n717), unc-26(e205); egl-1 (n487); dpy-3(e27). Most cross progeny were egg-laying defective because they were heterozygous for ced-3 and homozygous for egl-1. Rare egg-laying competent animals were picked as candidates for carrying new alleles of ced-3. Four such animals were isolated from about 10,000 F1 cross progeny of EMS-mutagenized animals. These new mutations were made homozygous to confirm that they carried recessive mutations of ced-3.

Molecular Biology

Standard techniques of molecular biology were used (Maniatis et al., Molecular Cloning: A Laboratory Manual, Cold Spring Harbor Laboratory, 1983).

Two cosmid libraries were used extensively in this work: a Sau3AI partial digest genomic library of 7000 clones in the vector pHC79 and a Sau3AI partial digest genomic library of 6000 clones in the vector pJB8 (Ish-Horowicz and Burke, Nucleic Acids Res. 9:2989 (1981)). The "right" end of MMM-C1 was cloned by cutting it with HindIII and self-ligating. The "left" end of MMM-C1 was cloned by cutting it with BglII or SalI and self-ligating.

The "right" end of Jc8 was made by digesting Jc8 with EcoRI and self-ligating. The "left" end of Jc8 was made by digesting Jc8 by SalI and self-ligating.

C. elegans RNA was extracted using guanidine isothiocyanate (Kim and Horvitz, Genes & Dev. 4:357–371 (1990)). Poly(A)$^+$ RNA was selected from total RNA by a poly(dT) column (Maniatis et al., 1983 supra). To prepare stage-synchronized animals, worms were synchronized at different developmental stages (Meyer and Casson, Genetics 106:29–44 (1986)).

For DNA sequencing, serial deletions were made according to a procedure developed by Henikoff (Gene 28:351–359 (1984)). DNA sequences were determined using Sequenase and protocols obtained from US Biochemicals with minor modifications.

The Tc1 DNA probe for Southern blots was pCe2001, which contains a Bergerac Tc1 element (Emmons et al., Cell 32:55–65 (1983)). Enzymes were purchased from New England Biolabs, and radioactive nucleotides were from Amersham.

Primer extension procedures followed the protocol by Robert E. Kingston (In: Current Protocols in Molecular Biology, Ausubel et al. (eds.), Greene Publishing Associates and Wiley-Interscience, New York, p. 4.8.1) with minor modifications.

Polymerase chain reaction (PCR) was carried out using standard protocols supplied by the GeneAmp Kit (Perkin Elmer). The primers used for primer extension and PCR are as follows:

| | | |
|---|---|---|
| Pex2: | 5' TCATCGACTTTTAGATGACTAGAGAACATC 3' | (SEQ ID NO:7); |
| Pex1: | 5' GTTGCACTGCTTTCACGATCTCCCGTCTCT 3' | (SEQ ID NO:8); |
| SL1: | 5' GTTTAATTACCCAAGTTTGAG 3' | (SEQ ID NO:9); |
| SL2: | 5' GGTTTTAACCAGTTACTCAAG 3' | (SEQ ID NO:10); |
| Log5: | 5' CCGGTGACATTGGACACTC 3' | (SEQ ID NO:11); and |
| Oligo10: | 5' ACTATTCAACACTTG 3' | (SEQ ID NO:12). |

Germline Transformation

The procedure for microinjection basically follows that of A. Fire (*EMBO J.* 5:2673–2680 (1986)) with modifications: Cosmid DNA was twice purified by CsCl-gradient. Miniprep DNA was used when deleted cosmids were injected. To prepare miniprep DNA, DNA from 1.5 ml overnight bacterial culture in superbroth (12 g Bacto-tryptone, 24 g yeast extract, 8 ml 50% glycerol, 900 ml $H_2O$, autoclaved; after autoclaving, 100 ml 0.17M $KH_2PO_4$ and 0.72 M $KH_2PO_4$ were added) was extracted by alkaline lysis method as described in Maniatis et al. (1983 supra). DNA was treated with RNase A (37°, 30 minutes) and then with protease K (55°, 30 minutes), extracted with phenol and then chloroform, precipitated twice (first in 0.3M sodium acetate and second in 0.1M potassium acetate, pH 7.2), and resuspended in 5 μl injection buffer as described by A. Fire (1986 supra). The DNA concentration for injection is in the range of 100 ug to 1 mg per ml.

All transformation experiments used ced-1(e1735); unc-31(e928) ced-3(n717) strain. unc-31 was used as a marker for co-transformation (Kim and Horvitz, 1990 supra). ced-1 was present to facilitate scoring of the Ced-3 phenotype. The mutations in ced-1 block the engulfment process of cell death, which makes the corpses of the dead cells persist much longer than in wild-type animals (Hedgecock et al., *Science* 220:1277–1280 (1983)). The Ced-3 phenotype was scored as the number of dead cells present in the head of young L1 animals. The cosmid C10D8 or the plasmid subclones of C10D8 were mixed with C14G10(unc-31(+)-containing) at a ratio of 2:1 or 3:1 to increase the chances that a Unc-31(+) transformant would contain the cosmid or plasmid being tested as well. Usually, 20–30 animals were injected in one experiment. Non-Unc F1 progeny of the injected animal were isolated three to four days later. About ½ to ⅓ of the non-Unc progeny transmitted the non-Unc phenotype to F2 progeny and established a transformant line. The young L1 progeny of such non-Unc transformant were checked for the number of dead cells present in the head using Nomarski optics.

RESULTS

Isolation of Additional ced-3 Alleles

All of the ced-3 alleles that existed previously were isolated in screens designed to detect viable mutants displaying the Ced phenotype (Ellis and Horvitz, *Cell* 44:817–829 (1986)). Such screens may have systematically missed any class of ced-3 mutations that is inviable as homozygotes. For this reason, a scheme was designed that could isolate recessive lethal alleles of ced-3. Four new alleles of ced-3 (n1163, n1164, n1165, n1286) were isolated in this way. Since new alleles were isolated at a frequency of about 1 in 2500, close to the frequency expected for the generation of null mutations by EMS in an average *C. elegans* gene (Brenner, *Genetics* 77:71–94 (1974); Greenwald and Horvitz, *Genetics* 96:147–160 (1980)), and all four alleles are homozygous viable, it was concluded that the null allele of ced-3 is viable.

Mapping RFLPs near ced-3

Tc1 is a *C. elegans* transposable element that is thought to be immobile in the common laboratory Bristol strain and in the Bergerac strain (Emmons et al., *Cell* 32:55–65 (1983)). In the Bristol strain, there are 30 copies of Tc1, while in the Bergerac strain, there are more than 400 copies of Tc1 (Emmons et al., 1983 supra; Finney, Ph.D. thesis, Massachusetts Institute of Technology, Cambridge, Mass., 1987). Because the size of the *C. elegans* genome is small (haploid genome size $8\times10^7$ bp) (Sulston and Brenner, *Genetics* 77:95–104 (1976)), a polymorphism due to Tc1 between the Bristol and Bergerac strains would be expected to occur about once every 200 kb. Restriction fragment length polymorphisms (RFLPs) can be used as genetic markers and mapped in a manner identical to conventional mutant phenotypes. A general scheme has been designed to map Tc1 elements that are dimorphic between the Bristol and Bergerac strains near any gene of interest (Ruvkun et al., *Genetics* 121:501–516 (1989)). Once tight linkage of a particular Tc1 to a gene of interest has been established, that Tc1 can be cloned and used to initiate chromosome walking.

A 5.1 kb Bristol-specific Tc1 EcoRI fragment was tentatively identified as containing the Tc1 closest to ced-3. This Tc1 fragment was cloned using cosmids from a set of Tc1-containing *C. elegans* Bristol genomic DNA fragments. DNA was prepared from 46 such Tc1-containing cosmids and screened using Southern blots to identify the cosmids that contain a 5.1 kb EcoRI Tc1-containing fragment. Two such cosmids were identified: MMM-C1 and MMM-C9. The 5.1 kb EcoRI fragment was subcloned from MMM-C1 into pUC13 (Promega). Since both ends of Tc1 contain an EcoRV site (Rosenzweig et al., *Nucleic Acids Res.* 11:4201–4209 (1983)), EcoRV was used to remove Tc1 from the 5.1 kb EcoRI fragment, generating a plasmid that contains only the unique flanking region of this Tc1-containing fragment. This plasmid was then used to map the specific Tc1 without the interference of other Tc1 elements.

unc-30(e191) ced-3(n717) dpy-4(e1166)/+++ males were crossed with Bergerac (EM1002) hermaphrodites, and Unc non-Dpy or Dpy non-Unc recombinants were picked from among the F2 progeny. The recombinants were allowed to self-fertilize, and strains that were homozygous for either unc-30(e191) dpy-4(Bergerac) or unc-30(Bergerac) dpy-4 (e1166) were isolated. After identifying the ced genotypes of these recombinant strains, DNA was prepared from these strains. A Southern blot of DNA from these recombinants was probed with the flanking sequence of the 5.1 kb EcoRI Tc1 fragment. This probe detects a 5.1 kb fragment in Bristol N2 and a 3.4 kb fragment in Bergerac. Five out of five unc-30 ced-3 dpy(+Berg) recombinants, and one of one unc-30(+Berg) ced-3 dpy-4 recombinants showed the Bristol pattern. Nine of ten unc-30(+Berg) dpy-4 recombinants showed the Bergerac pattern. Only one recombinant of unc-30(+Berg) dpy-4 resulted from a cross-over between ced-3 and the 5.1 kb Tc1 element. The genetic distance between ced-3 and dpy-4 is 2 map units (mu). Thus, this Tc1 element is located 0.1 mu on the right side of ced-3.

Cosmids MMM-C1 and MMM-C9 were used to test whether any previously mapped genomic DNA cosmids overlapped with these two cosmids. A contig of overlapping cosmids was identified that extended the cloned region near ced-3 in one direction.

To orient MMM-C1 with respect to this contig, both ends of MMM-C1 were subcloned and these subclones were used to probe the nearest neighboring cosmid C48D1. The "right" end of MMM-C1 does not hybridize to C48D1, while the "left" end does. Therefore, the "right" end of MMM-C1 extends further away from the contig. To extend this contig, the "right" end of MMM-C1 was used to probe the filters of two cosmid libraries (Coulson et al., *Proc. Natl. Acad. Sci. USA* 83:7821–7825 (1986)). One clone, Jc8, was found to extend MMM-C1 in the opposite direction of the contig.

RFLPs between the Bergerac and Bristol strains were used to orient the contig with respect to the genetic map. Bristol (N2) and Bergerac (EM1002) DNA was digested with various restriction enzymes and probed with different cosmids to look for RFLPs. Once such an RFLP was found, DNA from recombinants of the Bristol and Bergerac strains between ced-3 and unc-26, and between unc-30 and ced-3 was used to determine the position of the RFLP with respect to ced-3.

The "right" end of Jc8, which represents one end of the contig, detects an RFLP (nP33) when N2 and EM1002 DNA was digested with HindIII. A Southern blot of DNA from recombinants between three ced-3(+Berg) unc-26 was probed with the "right" end of Jc8. Three of three +Berg unc-26 recombinants showed the Bristol pattern, while two of two ced-3 unc-26(+Berg) recombinants showed the Bergerac pattern. Thus, nP33 mapped very close or to the right side of unc-26.

The "left" end of Jc8 also detects a HindIII RFLP (nP34). The same Southern blot was reprobed with the Jc8 "left" end. Two of the two ced-3 unc-26(+Berg) recombinants and two of the three ced-3(+Berg) unc-26 recombinants showed the Bergerac pattern. One of the three ced-3(+Berg) unc-26 recombinants showed the Bristol pattern. The genetic distance between ced-3 and unc-26 is 0.2 mu. Thus, nP34 was mapped between ced-3 and unc-26, about 0.1 mu on the right side of ced-3.

The flanking sequence of the 5.1 kb EcoRI Tc1 fragment (named nP35) was used to probe the same set of recombinants. Two of three ced-3(+Berg) unc-26 recombinants and two of two ced-3 unc-26(+Berg) recombinants showed the Bristol pattern. Thus, nP35 was also found to be located between ced-3 and unc-26, about 0.1 mu on the right side of ced-3.

A similar analysis using cosmid T10H5 which contains the HindIII RFLP (nP36), and cosmid B0564, which contains a HindIII RFLP (nP37), showed that nP36 and nP37 mapped very close or to the right of unc-30.

These experiments localized the ced-3 gene to an interval of three cosmids. The positions of the RFLPs, and of ced-3, unc-30 and unc-26 on chromosome IV, and their relationships to the cosmids are shown in FIG. 1. It has been demonstrated by microinjection that cosmids C37G8 and C33F2 carry the unc-30 gene (John Sulston, personal communication). Thus, the region containing the ced-3 gene was limited to an interval of two cosmids. These results are summarized in FIG. 1.

Complementation of ced-3 by Germline Transformation

Cosmids that were candidates for containing the ced-3 gene were microinjected into a ced-3 mutant to see if they rescue the mutant phenotype. The procedure for microinjection was that of A. Fire (*EMBO J.* 5:2673–2680 (1986)) with modifications. unc-31, a mutant defective in locomotion, was used as a marker for cotransformation (Kim and Horvitz, *Genes & Dev.* 4:357–371 (1990)), because the phenotype of ced-3 can be examined only by using Nomarski optics. Cosmid C14G10 (containing unc-31(+)) and a candidate cosmid were coinjected into ced-1 (e1375); unc-31(e928) ced-3(n717) hermaphrodites, and F1 non-Unc transformants were isolated to see if the non-Unc phenotype could be transmitted and established as a line of transformants. Young L1 progeny of such transformants were examined for the presence of cell deaths using Nomarski optics to see whether the Ced-3 phenotype was suppressed. Cosmid C14G10 containing unc-31 alone does not rescue ced-3 activity when injected into a ced-3 mutant. Table 4 summarizes the results of these transformation experiments.

As shown in Table 3, of the three cosmids injected (C43C9, W07H6 and C48D1), only C48D1 rescued the Ced-3 phenotype (2/2 non-Unc transformants rescued the Ced-3 phenotype). One of the transformants, nEX2, appears to be rescued by an extra-chromosomal array of injected cosmids (Way and Chalfie, *Cell* 54:5–16 (1988)), which is maintained as an unstable duplication, since only 50% of the progeny of a non-Unc Ced(+) animal are non-Unc Ced(+). Since the non-Unc Ced(+) phenotype of the other transformant (nIs1) is transmitted to all of its progeny, it is presumably an integrated transformant. L1 ced-1 animals contain an average of 23 cell corpses in the head. L1 ced-1; ced-3 animals contain an average of 0.3 cell corpses in the head. ced-1; unc-31 ced-3; nIS1 and ced-1; unc-31 ced-3; nEX2 animals contain an average of 16.4 and 14.5 cell corpses in the head, respectively. From these results, it was concluded that C48D1 contains the ced-3 gene.

In order to locate ced-3 more precisely within the cosmid C48D1, this cosmid was subcloned and the subclones were tested for the ability to rescue ced-3 mutants. C48D1 DNA was digested with restriction enzymes that cut rarely within the cosmid and the remaining cosmid was self-ligated to generate a subclone. Such subclones were then injected into a ced-3 mutant to look for completion. When C48D1 was digested with BamHI and self-ligated, the remaining 14 kb subclone (named C48D1-28) was found to rescue the Ced-3 phenotype when injected into a ced-3 mutant (FIG. 2 and Table 4). C48D1-28 was then partially digested with BglII and self-ligated. Clones of various lengths were isolated and tested for their ability to rescue ced-3.

One clone, C48D1-43, which did not contain a 1.7 kb BglII fragment of C48D1-28, was able to rescue ced-3 (FIG. 2 and Table 4). C48D1-43 was further subcloned by digesting with BamHI and ApaI to isolate a 10 kb BamHI-ApaI fragment. This fragment was subcloned into pBSKII+ to generate pJ40. pJ40 can restore Ced-3+ phenotype when microinjected into a ced-3 mutant. pJ40 was subcloned by deleting a 2 kb BglII-ApaI fragment to generate pJ107. pJ107 was also able to rescue the Ced-3 phenotype when microinjected into a ced-3 mutant. Deletion of 0.5 kb on the left side of pJ107 could be made by ExoIII digestion (as in pJ107del28 and pJ107del34) without affecting Ced-3 activity; in fact, one transgenic line, nEX17, restores full Ced-3 activity. However, the ced-3 rescuing ability was significantly reduced when 1 kb was deleted on the left side of pJ107 (as in pJ107del12 and pJ107del27), and the ability was completely eliminated when a 1.8 kb SalI-BglII fragment was deleted on the right side of pJ107 (as in pJ55 and pJ56), suggesting that this SalI site is likely to be in the ced-3 coding region. From these experiments, ced-3 was localized to a DNA fragment of 7.5 kb. These results are summarized in FIG. 2 and Table 4.

ced-3 Transcript pJ107 was used to probe a Northern blot of N2 RNA and detected a band of 2.8 kb. Although this transcript is present in 12 ced-3 mutant animals, subsequent analysis showed that all 12 ced-3 mutant alleles contain mutations in the genomic DNA that codes for this mRNA (see below), thus establishing this RNA as a ced-3 transcript.

The developmental expression pattern of ced-3 was determined by hybridizing a Northern blot of RNA from animals of different stages (eggs, L1 through L4 larvae and young adult) with the ced-3 cDNA subclone pJ118. Such analysis revealed that the ced-3 transcript is most abundant during embryonic development, which is the period when most programmed cell deaths occur, but it was also detected during the L1 through L4 larval stages and is present in relatively high levels in young adults. This result suggests that ced-3 is not only expressed in cells undergoing programmed cell death.

Since ced-3 and ced-4 are both required for programmed cell death in C. elegans, one of the genes might act as a regulator of transcription of the other gene. To examine if ced-4 regulates the transcription of ced-3, RNA was prepared from eggs of ced-4 mutants (n1162, n1416, n1894, and n1920), and a Northern blot was probed with the ced-3 cDNA subclone pJ118. The presence of RNA in each lane was confirmed with an actin I probe. Such an experiment showed that the level of ced-3 transcript is normal in ced-4 mutants. This indicates that ced-4 is unlikely to be a transcriptional regulator of ced-3.

Isolation of a ced-3 cDNA

To isolate cDNA of ced-3, pJ40 was used as a probe to screen a cDNA library of N2 (Kim and Horvitz, Genes & Dev. 4:357–371 (1990)). Seven cDNA clones were isolated. These cDNAs can be divided into two groups: one is 3.5 kb and the other 2.5 kb. One cDNA from each group was subcloned and analyzed further. pJ85 contains the 3.5 kb cDNA. Experiments showed that pJ85 contains a ced-3 cDNA fused to an unrelated cDNA; on Northern blots of N2 RNA, the pJ85 insert hybridizes to two RNA transcripts, and on Southern blots of N2 DNA, pJ85 hybridizes to one more band than pJ40 (ced-3 genomic DNA) does. pJ87 contains the 2.5 kb cDNA. On Northern blots, pJ87 hybridizes to a 2.8 kb RNA and on Southern blots, it hybridizes only to bands to which pJ40 hybridizes. Thus, pJ87 contains only ced-3 cDNA.

To show that pJ87 does contain the ced-3 cDNA, a frameshift mutation was made in the SalI site of pJ40 corresponding to the SaiII site in the pJ87 cDNA. Constructs containing the frameshift mutation failed to rescue the Ced-3 phenotype when microinjected into ced-3 mutant animals, suggesting that ced-3 activity has been eliminated.

ced-3 Sequence

The DNA sequence of pJ87 was determined (FIG. 3). pJ87 contains an insert of 2.5 kb which has an open reading frame of 503 amino acids (FIG. 3; SEQ ID NO: 2). The 5' end of the cDNA contains 25 bp of poly-A/T sequence, which is probably an artifact of cloning and is not present in the genomic sequence. The cDNA ends with a poly-A sequence, suggesting that it contains the complete 3' end of the transcript. 1 kb of pJ87 insert is untranslated 3' region and not all of it is essential for ced-3 expression, since genomic constructs with deletions of 380 bp of the 3' end can still rescue ced-3 mutants (pJ107 and its derivatives, see FIG. 2).

To confirm the DNA sequence obtained from the ced-3 cDNA and to study the structure of the ced-3 gene, the genomic sequence of the ced-3 gene in the plasmid pJ107 was determined (FIG. 3; SEQ ID NO: 1). Comparison of the ced-3 genomic and cDNA sequences revealed that the ced-3 gene has seven introns that range in size from 54 bp to 1195 bp (FIG. 4A). The four largest introns, as well as sequences 5' of the start codon, were found to contain repetitive elements (FIG. 3). Five types of repetitive elements were found, some of which have been previously characterized in non-coding regions of other C. elegans genes, such as fem-1 (Spence et al., Cell 60:981–990 (1990)), lin-12 (J. Yochem, personal communication), and myoD (Krause et al., Cell 63:907–919 (1990)). Of these, repeat 1 was also found in fem-1 and myoD, repeat 3 in lin-12 and fem-1, repeat 4 in lin-12, and repeats 2 and 5 were novel repetitive elements.

A combination of primer extension and PCR amplification was used to determine the location and nature of the 5' end of the ced-3 transcript. Two primers (Pex1 and Pex2) were used for the primer extension reaction. The Pex1 reaction yielded two major bands, whereas the Pex2 reaction gave one band. The Pex2 band corresponded in size to the smaller band from the Pex1 reaction, and agreed in length with a possible transcript that is trans-spliced to a C. elegans splice leader (Bektesh, Genes & Devel. 2:1277–1283 (1988)) at a consensus splice acceptor at position 2166 of the genomic sequence (FIG. 3). The nature of the larger Pex1 band is unclear.

To confirm the existence of this trans-spliced message in wild-type worms, total C. elegans RNA was PCR amplified using the SL1-Log5 and SL2-Log5 primer pairs, followed by a reamplification using the SL1-Oligo10 and SL2-Oligo10 primer pairs. The SL1 reaction yielded a fragment of the predicted length. The identity of this fragment was confirmed by sequencing. Thus, at least some, if not most, of the ced-3 transcript is trans-spliced to SL1. Based on this result, the start codon of the ced-3 message was assigned to the methionine encoded at position 2232 of the genomic sequence (FIG. 3).

The DNA sequences of 12 EMS-induced ced-3 alleles were also determined (FIG. 3 and Table 1). Nine of the 12 are missense mutations. Two of the 12 are nonsense mutations, which might prematurely terminate the translation of ced-3. These nonsense ced-3 mutants confirmed that the ced-3 gene is not essential for viability. One of the 12 mutations is an alteration of a conserved splicing acceptor G, and another has a change of a 70% conserved C at the splice site, which could also generate a stop codon even if the splicing is correct. Interestingly, these EMS-induced mutations are in either the N-terminal quarter or C-terminal half of the protein. In fact, 9 of the 12 mutations occur within the region of ced-3 that encodes the last 100 amino acids of the protein. Mutations are notably absent from the middle part of the ced-3 gene (FIG. 4A).

Ced-3 Protein Contains A Region Rich in Serines

The Ced-3 protein is very hydrophilic and no significantly hydrophobic region can be found that might be a transmembrane domain (FIG. 5). The Ced-3 protein is rich in serine. From amino acid 78 to amino acid 205 of the Ced-3 protein, 34 out of 127 amino acids are serine. Serine is often the target of serine/threonine protein kinases (Edelman, Ann. Rev. Biochem. 56:567–613 (1987)). For example, protein kinase C can phosphorylate serines when they are flanked on their amino and carboxyl sides by basic residues (Edelman, 1987 supra). Four of the serines in the Ced-3 protein are flanked by arginines (FIG. 6A). The same serine residues might also be the target of related Ser/Thr kinases.

To identify the functionally important regions of the Ced-3 protein, genomic DNAs containing the ced-3 genes from two related nematode species, C. briggsae (SEQ ID NO: 5) and C. vulgaris (SEQ ID NO: 6) were cloned and sequenced. Sequence comparison of the three ced-3 gene products showed that the non-serine-rich region of the proteins is highly conserved (FIG. 7). In C. briggsae and C.

vulgaris, many amino acids in the serine-rich region are dissimilar compared to the C. elegans Ced-3 protein. It seems that what is important in the serine-rich region is the overall serine-rich feature rather than the exact amino acid sequence.

This hypothesis is also supported by analysis of ced-3 mutations in C. elegans: none of the 12 EMS-induced mutations is in the serine-rich region, suggesting that mutations in this region might not affect the function of the Ced-3 protein and thus, could not be isolated in the screen for ced-3 mutants.

EXAMPLE 2

A Common Mechanism of Cell Death in Vertebrates and Invertebrates

Results from previous studies reported in the scientific literature suggest that cell deaths in a variety of organisms, including vertebrates as well as invertebrates, share a common mechanism which involves the activation of genes. These studies are consistent with the hypothesis that genes similar to the C. elegans ced-3 and ced-4 genes may be involved in the cell deaths that occur in vertebrates, although certain observations have led some to distinguish vertebrate cell deaths from the programmed cell deaths observed in such invertebrates as nematodes and insects. Some vertebrate cell deaths share certain characteristics with the programmed cell deaths in C. elegans that are controlled by ced-3 and ced-4. For example, up to 14% of the neurons in the chick dorsal root ganglia die immediately after their births, before any signs of differentiation (Carr and Simpson, Dev. Brain Res. 2:57–162 (1982)). Genes like ced-3 and ced-4 could well function in this class of vertebrate cell death.

Genetic mosaic analysis has suggested that ced-3 and ced-4 genes are expressed by cells that undergo programmed cell death, so that these genes may not act through cell—cell interactions (Yuan and Horvitz, Dev. Biol. 138:33–41 (1990)). Many cell deaths in vertebrates seem different in that they appear to be controlled by interactions with target tissues. For example, it is thought that a deprivation of target-derived growth factors is responsible for vertebrate neuronal cell deaths (Hamburger and Oppenheim, Neurosci. Comment. 1:39–55 (1982)); Thoenen et al., in: Selective Neuronal Death, Wiley, New York, 1987, Vol. 126, pp. 82–85). However, even this class of cell death could involve genes like ced-3 and ced-4, since pathways of cell death involving similar genes and mechanisms might be triggered in a variety of ways. Supporting this idea are several in vitro and in vivo studies which show that the deaths of vertebrate as well as invertebrate cells can be prevented by inhibitors of RNA and protein synthesis, suggesting that activation of genes are required for these cell deaths (Martin et al., J. Cell Biol. 106:829–844 (1988); Cohen and Duke, J. Immunol. 132:38–42 (1984); Oppenheim and Prevette, Neurosci. Abstr. 14:368 (1988); Stanisic et al., Invest. Urol. 16:19–22 (1978); Oppenheim et al., Dev. Biol. 138:104–113 (1990); Fahrbach and Truman, in: Selective Neuronal Death, Ciba Foundation Symposium, 1987, No. 126, pp. 65–81). It is possible that the genes induced in these dying vertebrate and invertebrate cells are cell death genes which are structurally related to the C. elegans ced-3 or ced-4 genes.

Also supporting the hypothesis that cell death in C. elegans is mechanistically similar to cell death in vertebrates is the observaiton that the protein product of the C. elegans gene ced-9 is similar in sequence to the human protein Bcl-2. ced-9 has been shown to prevent cells from undergoing programmed cell death during nematode development by antagonizing the activities of ced-3 and ced-4 (Hengartner, et al., Nature 356:494–499 (1992)). The bcl-2 gene has also been implicated in protecting cells against cell death. It seems likely that the genes and proteins with which ced-9 and bcl-2 interact are similar as well.

EXAMPLE 3

NEW FORMS OF THE CELL DEATH PROTEINS CED-3 AND CED-4 CAN PREVENT PROGRAMMED CELL DEATH IN C. ELEGANS

Figure 10:
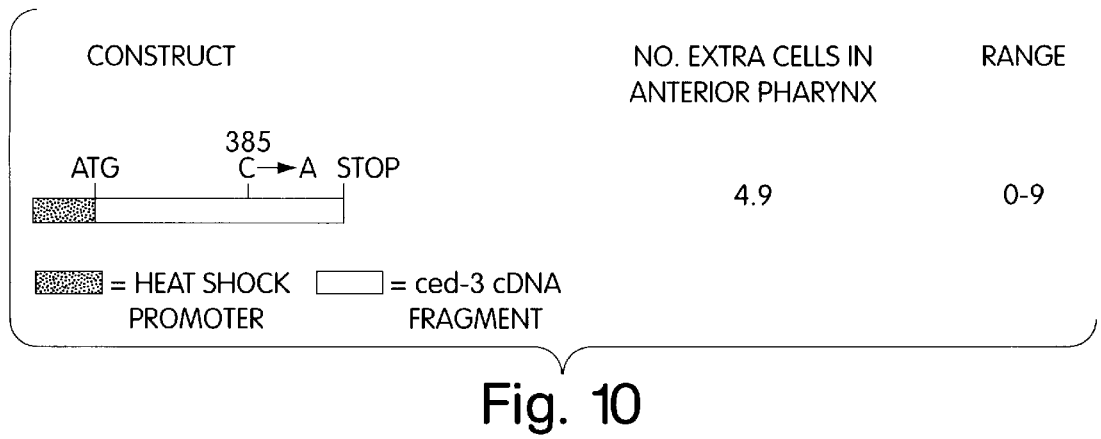
FIG. 10 shows a schematic representation of the Cysteine 358 to Alanine construct and the decrease in all deaths conferred by the presence of this contruct in C. elegans.

A ced-3 cDNA encoding a Cys358 to Ala substitution at the active site cysteine can prevent normally occurring programmed cell death in C. elegans when overexpressed using a heat shock promoter. The construct used to transform the C. elegans strains is shown in FIG. 10.

Representative data as shown in Table 5 demonstrate protective effect which alterations in the active site cysteine confer.

TABLE 5

| Construct | # extra cells in anterior pharynx | Number of animals observed | Range of extra cell counts |
|---|---|---|---|
| none | 0.13 | 40 | 0–1 |
| HSP-ced-3(c360A) line 1 | 2.9 | 8 | 0–8 |
| HSP-ced-3(c360A) line 2 | 4.9 | 9 | 0–9 |
| HSP-ced-3(c360A) line 3 | 2.6 | 9 | 1–9 |

Different lines represent independent strains carrying an extrachromosomal array containing the fusion construct and heat shocked at 33° C. for 1 hour.

EXAMPLE 4

Peptide Inhibitors of the Interleukin-1β Converting Enzyme (ICE) Arrest Programmed Cell Death of Motoneurons In Vitro and In Vivo Programmed cell death (PCD) has been well documented in the lumbar spinal motoneurons of the chick, where approximately 50% of the neurons produced during embryogenesis die before birth (Hamburger, Am. J. Anat. 102:365–410 (1958), Hollday and Hamburger, J. Comp. Neurol. 170:311–310 (1976), and Oppenheim et al., J. Comp. Neurol. 177:87–112 (1978)). Survival of motoneurons is dependent on their interaction with muscle targets, since removal of the limb induces greater than 90% motoneuron death whereas transplantation of a supernumerary limb increases the number of surviving motoneurons (Hamburger, Am J. Anat. 102:365–410 (1958), Hamburger and Oppenheim, Neurosci. Comm. 1:39–55 (1982), and Hollday and Hamburger, J. Comp. Neurol. 170:311–320 (1976)). While a precise factor has yet to be identified, the supply of target-derived trophic support is critical in determining the extent of motoneuron survival. The death of motoneurons that fail to acquire adequate supply of support appears to be mediated by new gene expression (Oppenheim et al., Dev. Biol. 138:104–113 (1990) and Milligan et al., J. Neurobiology 25:1005–1016 (1994)).

The aspartate-directed substrate specificity of ICE has allowed for the development of peptide inhibitors that are potent inhibitors of ICE proteolytic activity (Thornberry et al., Nature 356:768–774 (1992)). Those compounds mimic the aspartic acid in the P1 position of known ICE substrates, and are thus active site inhibitors. As such, these compounds may also be expected to inhibit other ICE family members that retain asp-ase activity. In this example ICE inhibitors were used to demonstrate the role of ICE-like proteases in the death of chick spinal motoneurons and demonstrate that cell-permeable peptide inhibitors of ICE arrest the PCD of motoneurons in vitro and in vivo. Furthermore, these inhibitors can also reduce PCD in other cell lineages in vivo.

Figure 11A:
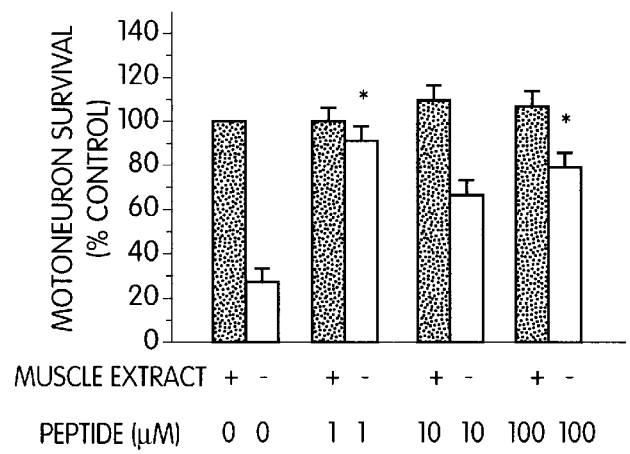
FIGS. 11A–11E show the effectiveness of peptide inhibitors of ICE in arresting motoneuron death.
Figure 11B:
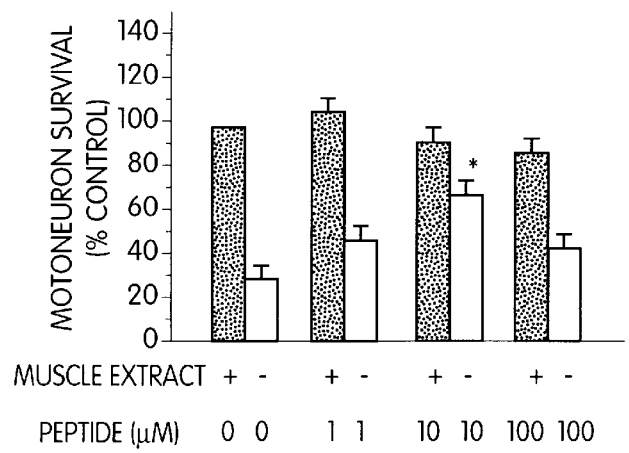
Figure 11C:
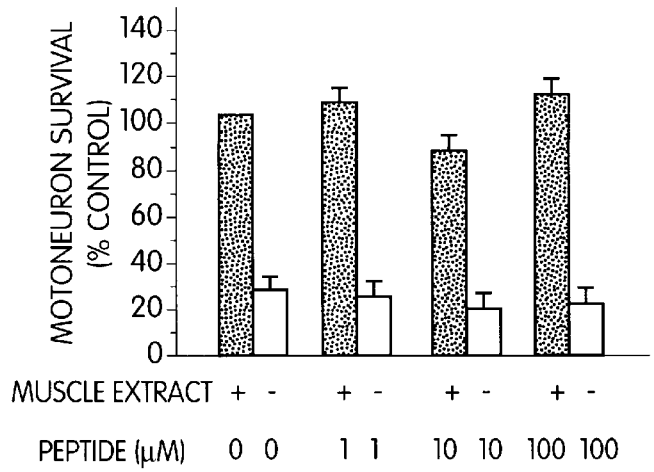
Figure 11D:
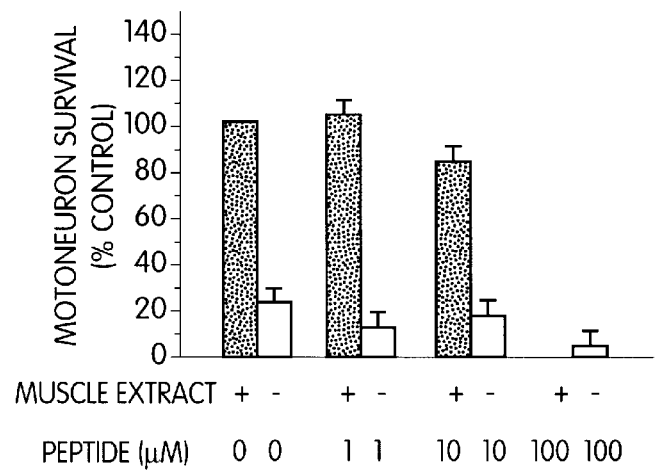
Figure 11E:
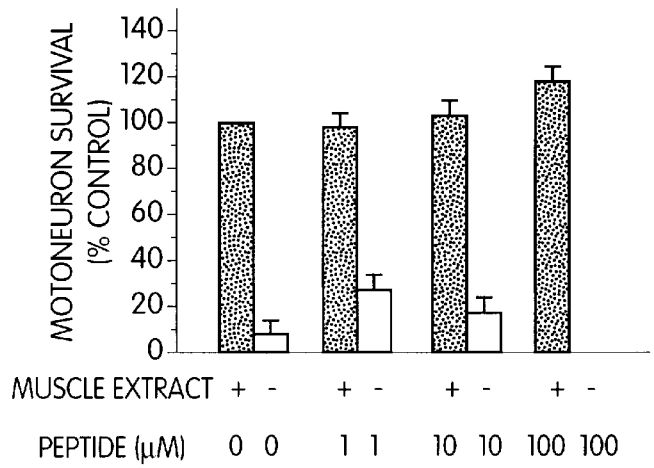
Figure 12A:
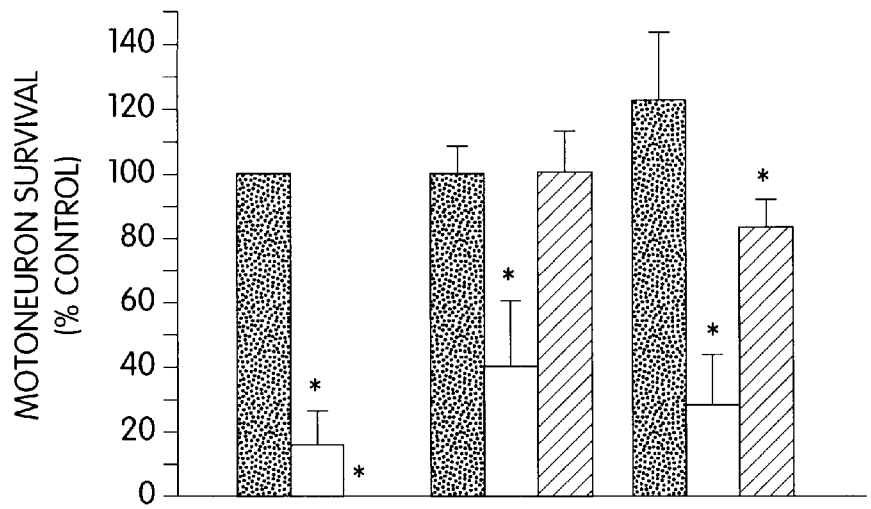
FIGS. 12A and 12B show that the inhibition of ICE delays the death of motoneurons.
Figure 12B:
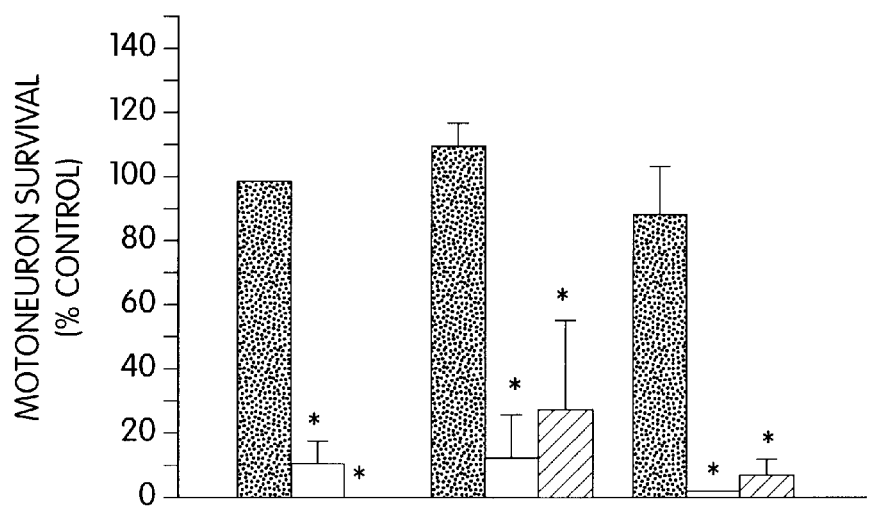
Figure 15C:
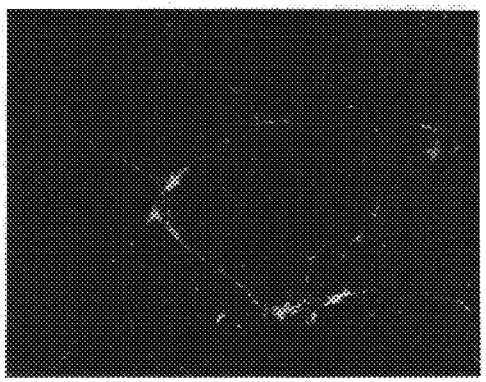
FIG. 15 (C–G) shows photomicrographs of SC1 immunopositive motoneurons cultured for 6 days with muscle extract (Panel C), without muscle extract (Panel D), with muscle extract and treated with the aldehyde peptide inhibitor of ICE(Ac-YVAD-CHO) as described in Example 4 (Panel E; arrows indicate two SC1 immunopositive motoneurons), without muscle extract and treated with the peptide inhibitor of ICE (Panel F), or initially plated without muscle extract, treated with the peptide inhibitor of ICE, then treated with muscle extract at three days in culture (Panel G). Scale bar=25 μm
Figure 15D:
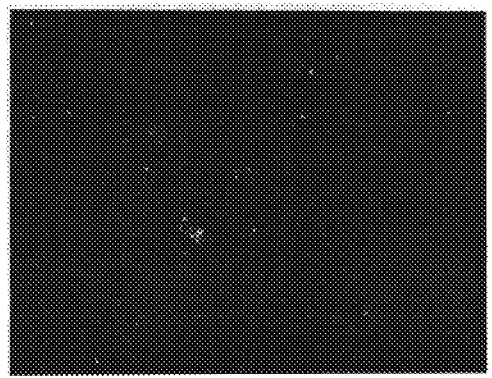
Figure 15E:
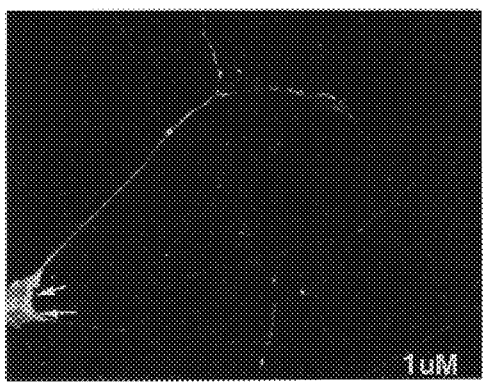
Figure 15F:
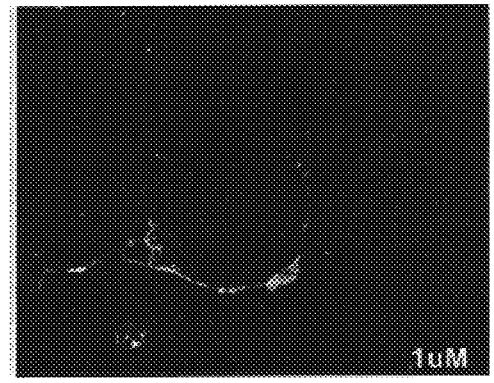
Figure 15G:

A tissue culture model system that allows isolation of a relatively pure population of motoneurons whose survival is dependent on muscle extract, a potent source of target-derived trophic support, was used to test the ability of peptide inhibitors of ICE to block motoneuron cell death (Milligan et al., *J. Neurobiology* 25:1005–1016 (1994) and Block-Gallego et al., *Development.* 111:221–232 (1991)). The death of motoneurons deprived of trophic support in vitro requires new gene expression and occurs by apoptosis (Milligan et al., *J. Neurobiology* 25:1005–1016 (1994)). Motoneurons deprived of trophic support at the time of plating become irreversibly committed to undergo cell death after 16–18 hours (Milligan et al., *J. Neurobiology* 25:1005–1016 (1994)). FIGS. 11A and 11B show that treatment with peptide inhibitors of ICE during this time period at concentrations known to be effective in blocking IL-1 maturation in intact cells (Thornberry et al., *Nature* 356:768–774 (1992)), substantially prevents the motoneuron death observed after 3 days. Administration of either a reversible peptide aldehyde (Acetyl-Tyr-Val-Ala-Asp-addehyde)-(Acetyl-Tyr-Val-Ala-Asp-chloromethyl-ketone) or an irreversible peptide chloro-methylketone (Acetyl-Tyr-Val-Ala-Asp-aldehyde)-(Acetyl-Tyr-Val-Ala-Asp-chloro-methylketone) protease inhibitor had inhibitory effects on motoneuron death, although the peptide aldehyde was more effective. Treatment with the ICE inhibitors had no affect on cells receiving muscle extract, indicating that they are not toxic to motoneurons at the doses tested (FIGS. 11A–11B). Treatment with control peptide aldehyde or choloromethylketone inhibitors that lack aspartate in the P1 position had no survival promoting effects, further suggesting that it is the specific inhibition of ICE or ICE-like asp-ases that inhibit death (FIGS. 11C–11E). When motoneurons are treated with peptide inhibitors in the absence of muscle extract for three days and subsequently supplemented on day three with muscle extract, they continue to survive, and by six days appear as healthy and differentiated as the motoneurons that were continuously supplied with muscle extract (FIGS. 12A, 12B, 15G). Thus, motoneurons rescued for 3 days by ICE inhibitors remain capable of responding to trophic factors present in muscle extract. These results suggest that the commitment to cell death initiated by trophic factor deprivation in vitro involves an ICE-like asp-ase.

Figure 13:
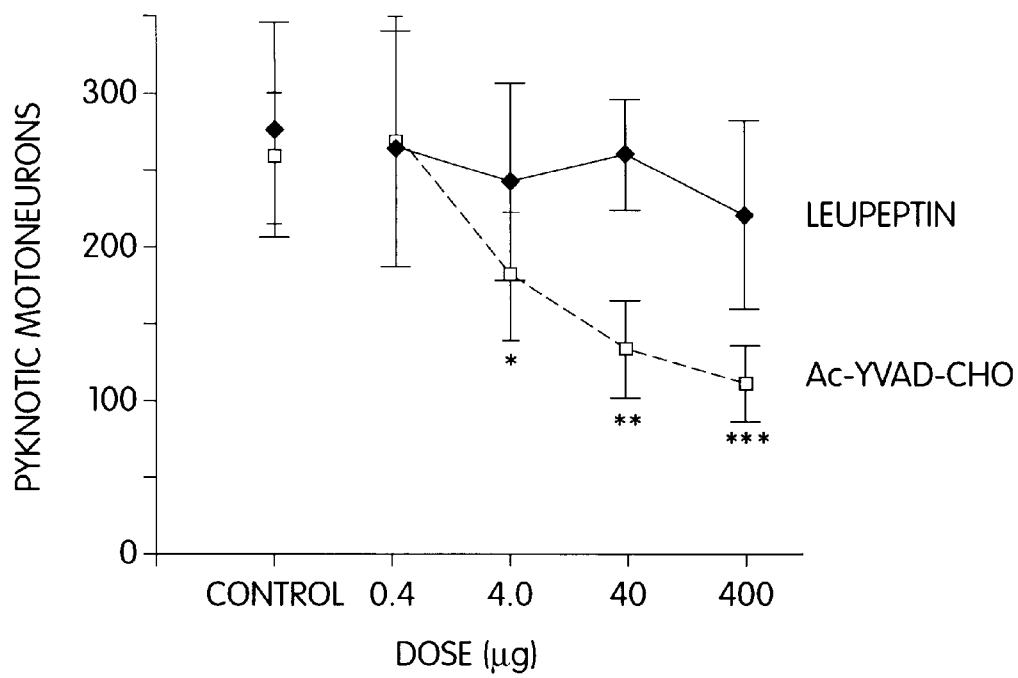
FIG. 13 shows that the effectiveness of the peptide aldehyde inhibitor of ICE (Ac-YVAD-CHO) for inhibition of motoneuron PCD in vivo is dose dependent.
Figure 14:
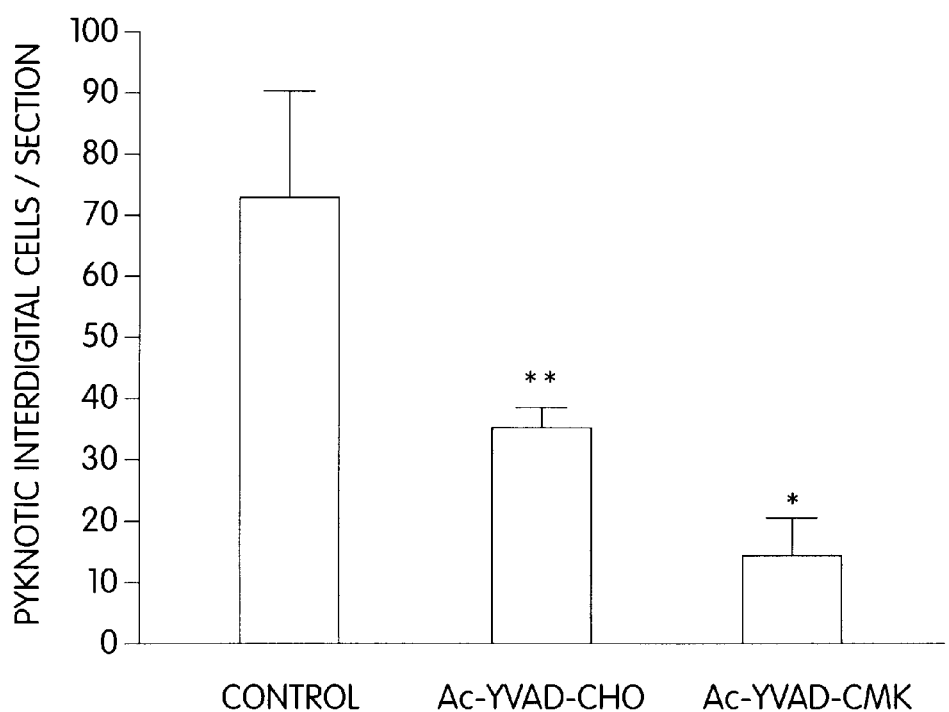
FIG. 14 shows that peptide inhibitors of ICE prevent the cell death of hind limb interdigital cell death.

To demonstrate the physiological relevance of the observations obtained in vitro the role of ICE-like proteases on several models of PCD in the chick embryos in vivo was investigated. In the first model, embryos were treated with a single dose of an ICE inhibitor or control protease inhibitor on embryonic day 8 (E8), the time of maximum naturally occurring motoneuron cell death (Hamburger et al., *J. Morph.* 88:49–92 (1951)). Embryos treated in vivo with the peptide inhibitors appeared to develop normally and there were no gross abnormalties. However, 15 hours following drug treatment, there are significantly fewer pyknotic cells present in the lumbar spinal cord of animals treated with the peptide inhibitors of ICE as compared to animals treated with control protease inhibitors (Table 6A). This effect is dose dependent (FIG. 13). 24 hours after treatment there is a similar reduction in the number of pyknotic cells and a significant increase in the number of healthy motoneurons (Table 6B). The increase in healthy cells suggests that cell death was indeed inhibited and that there was not simply a morphological change in the dying neurons that precluded their identification as pyknotic. The ability of ICE inhibitors to block the naturally occurring cell death of interdigital cells in the developing limb was also studied. These cells undergo PCD as a means of sculpting the digits in many vertebrates. When embryos were treated with either ICE inhibitor on embryonic days, E6 and E7, there was a substantial reduction in the number of pyknotic cells between the digits of the hindlimb (FIG. 14). These data support the theory that ICE-like asp-ases are key components of the PCD pathway in multiple cell types, including neurons and non-neurons.

Next, a second model of motoneuron PCD in which animals were subjected to limb bud removal, thereby inducing greater than 90% of the motoneurons to die was investigated (Hamburger, *Am. J. Anat.* 102:365–410 (1958), Hamburger et al., *Neurosci. Comm.* 1:39–55 (1982). Surprisingly in this model peptide inhibitors of ICE had no survival promoting effect (Table 7).

The ability of the ICE inhibitors to block cell death in two classes of neurons whose naturally occurring death appears to be independent of target interaction was also studied. First, motoneurons in the cervical spinal cord undergo PCD between E4 and E5, with maximum levels occurring at E4.5. It is believed that these cells die by a means independent of target interactions since a variety of growth factors shown to be effective in rescuing lumbar motoneurons are ineffective in rescuing cervical motoneurons from PCD. Peptide inhibitors of ICE have no survival promoting effects on cervical motoneurons in vivo (Table 8). Second, the death of undifferentiated neurons and precursor cells that occurs in the neural tube between E2 and E3 is also thought to be target independent and unaffected by treatment with a variety of growth factors (Homma et al., *J. Comp. Neurol.* 345:377–95 (1994)). The PCD of these cells is also insensitive to rescue by the peptide inhibitors (Table 9). Although one cannot exclude the possibility that the dosage or timing of peptide administrations account for the observed lack of inhibition, this is unlikely given the positive effects on interdigital cell death observed at a similar embryonic stage (see above). These results show that not all naturally occurring cell deaths are blocked by inhibitors of ICE or related aspartases.

While we do not wish to bind ourselves to a particular model, several hypotheses can be offered to explain the differential ability of ICE inhibitors to block motoneuron death in the various models. It is possible, for instance, that the peptides are not present at critical PCD commitment times in each model. In the limb bud extrepation model, where the limb bud is removed at E2, perhaps an asp-ase-sensitive step occurred prior to E5 when drugs were applied. Further time course experiments will clarify this issue. A second possibility is that the molecular machinery that controls cell death changes during the course of development. The two cases where the ICE inhibitor blocked PCD were at E8 (motoneuron death) and E7.5 (interdigital cell death). The cases in which the peptides were ineffective were at E6 (limb bud extrepation), E4 (cervical spinal motoneurons) and E3 (undifferentiated neurons and precursors). Thus it is possible that early in development, cell death mechanisms occur which may not be inhibited by asp-ase inhibitors employed in these studies, while at later times, different mechanisms are inhibited by the compounds employed.

The experiments described in this example demonstrate that ICE or an ICE-like asp-ase have a regulatory role in vertebrate cell death in vivo. The inhibitors used in the present example were designed as asp-ase inhibitors, and inhibit not only ICE, but also related proteases that have been implicated in apoptosis and that resemble ICE with respect to cleavage after apportate residues. The effect of cell-permeable inhibitors on the ICE protease family may result in the arrest of motoneuron death. Such arrest may subsequently allow time for the cell to reorganize and recover, thereby opening up therapeutic strategies in pathological conditions involving motoneuron death such as that which occurs following spinal cord injuries or stroke. In addition, motoneuron death as observed in neurodegenerative diseases (e.g., ALS) might also be prevented by treatment with these asp-ase inhibitors.

Methods

Methods for motoneuron cultures. Spinal cords from embryonic day 5 chicks were dissected in cold phosphate buffered saline (pH 7.4; PBS), incubated in trypsin (0.25% in PBS; Gibco) and the tissue dissociated by passing it several times through a 1.0 ml pipette tip. Cells were layered onto a 6.8% metrizamide (Serva) cushion, centrifuged at 500 g. The cell layer at the interface, containing predominantly motoneurons, was collected. Motoneurons were plated onto 12 mm glass coverslips (Fisher) that were initially coated with poly-ornithine (1 $\mu$g/ml; Sigma), washed extensively with dH$_2$O and subsequently coated with laminin (20 ug/ml; Gibco). A culture medium containing Leibovitz's L15 media (Gibco) supplemented with sodium bicarbonate (625 $\mu$g/ml), glucose (20 mM), progesterone ($2\times10^{-8}$M; Sigma), sodium sclenite ($3\times10^{-8}$M; Sigma), conalbumin (0.1 mg/ml; Sigma), putrescine ($10^{-4}$M; Sigma), insulin (5 $\mu$g/ml; Sigma) and penicillin-streptomycin (Gibco) was used. Unless otherwise noted, 1 ml of complete media, with or without muscle extract (MEX) (20 $\mu$g/ml; prepared as previously described; Bloch-Gallego et al., *Development* 111:221–232 (1991)), was added to the tissue culture wells that contained a coverslip seeded with cells ($1\times10^4$ cells/coverslip). We have previously shown that motoneurons in culture become committed to die approximately 16 hours after culture in the absence of MEX (Oppenheim et al., *Dev. Biol.* 138:104–113 (1990)). For these experiments, motoneurons were treated with control protease inhibitors or with peptide inhibitors of ICE (see "peptides" below). The calpain inhibitor Ed64 was purchased from Sigma (St. Louis, Mo.).) motoneurons were treated with the protease inhibitors every two hours between 14 and 24 hours in culture (the time when cells in the absence of MEX are dying). Treatment with the peptide inhibitor was accomplished by adding the appropriate concentration of peptide to the cells so that the final concentration in the well after the final application would be as indicated in the figures; no more than 0.5% of the total volume of media was added at any time. Aldehyde peptide inhibitors were diluted in dH$_2$O and chloromethylketone inhibitors were diluted in DMSO. After a total of three days in culture, cells were incubated with the monoclonal antibody SC1 (1:5 of supernatant in PBS; 15) for 1.5 hours at 37° C., washed with PBS, fixed with 10% formaldehyde in PBS and subsequently incubated with an FITC-labeled goat anti-mouse IgG secondary antibody (1:50 diluted in PBS; Fisher). After extensive washes with PBS, the cells were incubated with the fluorescent DNA intercalating dye, 4',6-Diamidino-2-phenylindole (DAPI; 1:100,000 in PBS; Sigma) and mounted with the aqueous mounting media Gel-Mount (Biomeda). Surviving motoneurons were counted in 5 predetermined 40× objective fields. For a motoneuron to be considered viable, its cell body must be present in the filed of view, exhibit uniform SC1 immunoreactivity on its surface membrane and possess a uniform, non-condensed DAPI stained nucleus. Peptides. Two peptide inhibitors of ICE, Acetyl-Tyr-Val-Ala-Asp-aldehyde (Ac-YVAD-CHO) and Acetyl-Tyr-Val-Ala-Asp-chloromethylketone (Ac-YVAD-CMK) and two control peptide inhibitors, Acetyl-Leu-Leu-Arg-aldehyde (Ac-LLR-CHO; Leupeptin) and n-tosyl-Lys-chloromethyl-ketone (Tos-Lys-CMK) were synthesized by Bachem Biosciences (King of Prussia, PA) and shown by thin layer chromatography and HPLC to be greater than 98% pure. AC-YVAD-CHO is a reversible, competitive inhibitor of human ICE and has been shown to inhibit ICE activity in intact monocytic cells (Thornberry et al., *Nature* 356:768–774 (1992)).

Methods for administration of peptides to examine effects on naturally occurring motoneuron cell death in vivo. Although cell death of lumbar motoneurons occurs between E6 and E12, the peak period of death (i.e., the greatest number of pyknotic cells) occurs on E8 (Oppenheim et al., *J. Comp. Neurol.* 177:87–112 (1978)). For these experiments, embryos were given a single administration of an agent on E8 0 hr and sacrificed 15 hours later. 400 $\mu$g was chosen since this was the most effective dose tested (FIG. 13). Ac-YVAD-CMK and Tos-Lys-CMK were administered in a solution of DMSO/BSA, whereas Ac-YVAD-CHO and leupeptin (Sigma) were in BSA alone. The solutions (50–100 $\mu$l) were dropped onto the highly vascularized chorioallantoic membrane through a window in the shell. The control groups included both DMSO and BSA or vehicle alone. Embryos were killed and staged by the Hamburger-Hamilton series (Hamburger and Hamilton, *J. Morph.* 88:49–92 (1951)). The thoraco-lumbar spinal cord was dissected, fixed in Carnoys or Bouins fixative, processed for paraffin histology, serially sectioned (10–12 $\mu$m) and stained with either thionin or hematoxylin and eosin. Pyknotic motoneurons were identified based on criteria previously described (Chu-Wang and Oppenheim, *J. Comp. Neurol.* 177:33–58 (1978); Clarke and Oppenheim In *Methods in Cell Biology Series; Cell Death*; eds: Schwartz and Osborne. Academic Press. New York, N.Y. In press.) and were counted in every 10th or 20th section through the entire lumbar enlargement. The total number of pyknotic cells were then estimated by multiplying these values by 10 or 20. All cell counts were performed by individuals blinded with regard to drug treatment of the embryos.

Methods for limb bud removal experiments. A unilateral limb bud removal was performed on E2 as described previously (Oppenheim et al., *J. Comp. Neurol.* 177:87–112 (1978)). Because induced cell death following limb removal begins on E5 (before that there is no difference in the number of motoneurons between the operated or unoperated sides) embryos were given one treatment of Ac-YVAD-CHO (40 $\mu$g) or BSA (control) at E5-0 hr and another at E5–12 hours (total peptide administered was 80 $\mu$g). Animals were killed at E6-0 hr. Methods were the same as described above except the section thickness was 6–8 $\mu$m (see Method for Administration of Peptides, above).

Methods for limb bud interdigital regions. Embryos were treated with 100 $\mu$g of peptide or vehicle in 50 $\mu$l on E6.0 and on E7.0 (total 200 $\mu$g) as described above (Chu-Wang and Oppenheim, *J. Comp. Neurol.* 177:33–58 (1978); Clarke and Oppenheim In *Methods in Cell Biology Series; Cell Death*; eds: Schwartz and Osborne. Academic Press. New York, N.Y. In press.) and killed at E7.5. The footpads were placed in Bouin's fixative and processed as described above (see Method of Limb Bud Removal, above). Pyknotic cells in all interdigital regions were counted in every 10th section (6–8 $\mu$m) of serial transverse sections through the entire footpad.

TABLE 1

Sites of Mutations in the ced-3 Gene

| Allele | Mutation | Nucleotide | Codon | Consequence |
|---|---|---|---|---|
| n1040 | C to T | 2310 | 27 | L to F |
| n718 | G to A | 2487 | 65 | G to R |
| n2433 | G to A | 5757 | 360 | G to S |
| n1164 | C to T | 5940 | 403 | Q to termination |
| n717 | G to A | 6297 | — | Splice acceptor loss |
| n1949 | C to T | 6322 | 412 | Q to termination |
| n1286 | G to A | 6342 | 428 | W to termination |
| n1129 | C to T | 6434 | 449 | A to V |
| n1165 | C to T | 6434 | 449 | A to V |
| n2430 | C to T | 6485 | 466 | A to V |
| n2426 | G to A | 6535 | 483 | E to K |
| n1163 | C to T | 7020 | 486 | S to F |

Nucleotide and codon positions correspond to the numbering in FIG. 3.

TABLE 2 ced-3-lacZ Fusions Which Prevent Programmed Cell Death

| Strain Name | Construct | Average # Extra Cells | Number of Animals |
|---|---|---|---|
| N2 (wild-type) | — | 0.1 | 40 |
| nEx 121 | PBA | 2.0 | 23 |
| nEx 70 | PBA | 2.4 | 31 |
| nEx 67 | BGAFQ | 2.1 | 18 |
| nEx 66 | BGAFQ | 2.1 | 25 |

TABLE 3

Summary of Transformation Experiments Using Cosmids in the ced-3 Region

| Cosmid injected | No. of non-Unc transformants | Ced-3 phenotype | Strain name |
|---|---|---|---|
| C43C9; C14G10 | 1 | − | MT4302 |
| W07H6; C14G10 | 3 | − | MT4299 |
|  |  | − | MT4300 |
|  |  | − | MT4301 |
| C48D1; C14G10 | 2 | + | MT4298 |
|  |  | + | MT4303 |

Animals injected were of genotype: ced-1(e1735); unc-31(e929) ced-3(n717).

TABLE 4

The expression of ced-3(+) transformants

| Genotype | DNA injected | Average No. cell deaths in L1 head | No. Animals scored |
|---|---|---|---|
| ced-1 | — | 23 | 20 |
| ced-1; ced-3 | — | 0.3 | 10 |
| ced-1; nIS1 unc-31 ced-3 | C48D1; C14G10 | 16.4 | 20 |
| ced-1; unc-31 ced-3; nIS1/+ |  | 14.5 | 20 |
| ced-1; unc-31 ced-3; nEX2 | C48D1; C14G10 | 13.2 | 10/14 |
|  |  | 0 | 4/14 |
| ced-1; unc-31 ced-3; nEX10 | C4BD1-28; C14G10 | 12 | 9/10 |
|  |  | 0 | 1 of 10 |
| ced-1; unc-31 ced-3; nEX9 | C48D1-28; C14G10 | 12 | 10 |
| ced-1; unc-31 ced-3; nEX11 | C48D1-43 C14G10 | 16.7 | 10/13 |
|  |  | Abnormal cell deaths | 3/13 |
| ced-1; unc-31 ced-3; nEX13 | pJ40; C14G10 | 13.75 | 4/4 |
| ced-1; unc-31 ced-3; nEX17 | pJ107de128, pJ107de134 C14G10 | 23 | 12/14 |
|  |  | 0 | 2/14 |
| ced-1; unc-31 ced-3; nEX18 | pJ107de128, PJ107de1134 C14G10 | 12.8 | 9/10 |
|  |  | 0 | 1/10 |
| ced-1; unc-31 ced-3; nEX19 | pJ107de128, pJ107de134 G14G10 | 10.6 | 5/6 |
|  |  | 0 | 1/6 |
| ced-1; unc-31 ced-3; nEX16 | pJ107de112, pJ107de127 C14G10 | 7.8 | 12/12 |

Alleles of the genes used are ced-1(e1735), unc-31(e928), and ced-3(n717).

TABLE 6A

Pyknotic Lumbar Motoneurons on E8
(15 hours post treatment)

| Control | ICE Inhibitors | | Control Protease Inhibitors | |
|---|---|---|---|---|
| | Ac-YVAD-CHO | Ac-YVAD-CMK | Leupeptin | Tos-Lys-CMK |
| 286 ± 37 (20) | 146 ± 35* (8) | 216 ± 27** (10) | 310 ± 40 (20) | 285 ± 31 (20) |

*p ≦ 0.001; **p ≦ 0.01

Embryos were treated as described and results are expressed as mean ± SD. Multiple t-tests were performed with the Bonferroni correction. P-values were the same for comparisons of Ac-YVAD-CHO or Ac-YVAD-CMK with control, Ac-LLR-CHO or TOS-Lys-CMK treated animals. The number in brackets represents the n for each group.

TABLE 6B

Pyknotic and Healthy Lumbar Motoneurons on E9
(24 hours post treatment)

| Control | ICE Inhibitors | | Control Protease Inhibitors | |
|---|---|---|---|---|
| | Ac-YVAD-CHO | Ac-YVAD-CMK | Leupeptin | Tos-Lys-CMK |
| Pyknotic Motoneurons | | | | |
| 316 ± 47 (21) | 150 ± 30** (6) | 200 ± 33** (6) | 297 ± 51 (20) | 345 ± 39 (22) |
| Healthy Motoneurons | | | | |
| 13,605 ± 890 (20) | 15,680 ± 684** (6) | 16,231 ± 755* (7) | 14,117 ± 971 (18) | 13,257 ± 773 (19) |

*p ≧ 0.001; **p ≧ 0.01

Embryos were treated as described (17) except that they were killed on E9-0 hr (24 hours after treatment), results are expressed as mean ± SD. Multiple t-tests were performed with the Bonferroni correction. P-values were the same for comparisons of Ac-YVAD-CHO or Ac-YVAD-CMK with control, Ac-LLR-CHO or Tos-Lys-CMK treated animals. The number in brackets represents the n for each group.

TABLE 7

Pyknotic and Healthy Lumbar Motoneurons on E6 Following Limb Bud Removal.

| Ipsilateral | | Contralateral | |
|---|---|---|---|
| Control | Ac-YVAD-CHO | Control | Ac-YVAD-CHO |
| Pyknotic Motoneurons | | | |
| 375 ± 74* (6) | 317 ± 89* (6) | 73 ± 16 (6) | 67 ± 13 (6) |
| Healthy Motoneurons | | | |
| 11,371 ± 1780* (6) | 11,109 ± 1592* (6) | 18,455 ± 1661 (6) | 17,914 ± 1733 (6) |

*p ≦ 0.001 Ipsilateral vs Contralateral

Embryos were treated as described and results are expressed as mean ± SD. Multiple t-tests were performed with the Bonferroni correction. The aldehyde peptide inhibitor of ICE, Ac-YVAD-CHO had no survival promoting effect as compared to the unoperated contralateral side. The number in brackets represents the n for each group.

TABLE 8

Pyknotic Cervical Motoneurons on E4.5.

| Control | ICE Inhibitors | | Control Protease Inhibitor |
|---|---|---|---|
| | Ac-YVAD-CHO | Ac-YVAD-CMK | Leupeptin |
| 24.1 ± 3.1 (7) | 25.9 ± 3.4 (6) | 26.7 ± 2.2 (6) | 32.5 ± 7.9 (3) |

Embryos were treated as described and results are expressed as mean ± SD. Multiple t-tests were performed with the Bonferroni correction. The peptide inhibitors of ICE, Ac-YVAD-CHO or Ac-YVAD-CMK had no survival promoting effects on cervical motoneurons as compared to control or Ac-LLR-CHO treated animals. The number in brackets represents the n for each group.

TABLE 9

Pyknotic Cells in the Early Neural Tube.

| Floor Plate | | | Dorsal Spinal Cord | | |
|---|---|---|---|---|---|
| | ICE Inhibitors | | | ICE Inhibitors | |
| Control | Ac-YVAD-CHO | Ac-YVAD-CMK | Control | Ac-YVAD-CHO | Ac-YVAD-CMK |
| 0.898 ± 0.103 (6) | 1.115 ± 0.246 (6) | 0.872 ± 0.201 (5) | 1.322 ± 0.471 (6) | 1.350 ± 0.297 (6) | 1.372 ± 0.235 (5) |

Embryos were treated as described and results are expressed as mean ± SD. Multiple t-tests were performed with the Bonferroni correction. The peptide inhibitors of ICE, Ac-YVAD-CHO or Ac-YVAD-CMK, had no survival promoting effects on floorplate or dorsal spinal cord cells as compared to control animals. The number in brackets represents the n for each group.

Equivalents

Those skilled in the art will recognize, or be able to ascertain using no more than routine experimentation, many equivalents to the specific embodiments of the invention described herein. Such equivalents are intended to be encompassed by the following claims. For example, functional equivalents of DNAs and RNAs may be nucleic acid sequences which, through the degeneracy of the genetic code, encode the same proteins as those specifically claimed. Functional equivalents of proteins may be substituted or modified amino acid sequences, wherein the substitution or modification does not change the activity or function of the protein. A "silent" amino acid substitution, such that a chemically similar amino acid (e.g., an acidic amino acid with another acidic amino acid) is substituted, is an example of how a functional equivalent of a protein can be produced. Functional equivalents of nucleic acids or proteins may also be produced by deletion of nonessential sequences.

What is claimed is:

1. An isolated substrate-specific protease having the amino acid sequence of the Ced-3 protein shown in FIG. 6A (SEQ ID NO: 2).

2. Isolated protein having cell death activity and the amino acid sequence of the NEDD-2 protein shown in FIG. 6B (SEQ ID NO: 13).

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
        (A) LENGTH: 7653 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:1:

```
AGATCTGAAA TAAGGTGATA AATTAATAAA TTAAGTGTAT TTCTGAGGAA ATTTGACTGT      60
TTTAGCACAA TTAATCTTGT TTCAGAAAAA AAGTCCAGTT TTCTAGATTT TTCCGTCTTA     120
TTGTCGAATT AATATCCCTA TTATCACTTT TTCATGCTCA TCCTCGAGCG GCACGTCCTC     180
AAAGAATTGT GAGAGCAAAC GCGCTCCCAT TGACCTCCAC ACTCAGCCGC CAAAACAAAC     240
GTTCGAACAT TCGTGTGTTG TGCTCCTTTT CCGTTATCTT GCAGTCATCT TTTGTCGTTT     300
TTTTCTTTGT TCTTTTTGTT GAACGTGTTG CTAAGCAATT ATTACATCAA TTGAAGAAAA     360
GGCTCGCCGA TTTATTGTTG CCAGAAAGAT TCTGAGATTC TCGAAGTCGA TTTTATAATA     420
TTTAACCTTG GTTTTTGCAT TGTTTCGTTT AAAAAAACCA CTGTTTATGT GAAAAACGAT     480
TAGTTTACTA ATAAAACTAC TTTTAAACCT TTACCTTTAC CTCACCGCTC CGTGTTCATG     540
GCTCATAGAT TTTCGATACT CAAATCCAAA AATAAATTTA CGAGGGCAAT TAATGTGAAA     600
CAAAAACAAT CCTAAGATTT CCACATGTTT GACCTCTCCG GCACCTTCTT CCTTAGCCCC     660
ACCACTCCAT CACCTCTTTG GCGGTGTTCT TCGAAACCCA CTTAGGAAAG CAGTGTGTAT     720
CTCATTTGGT ATGCTCTTTT CGATTTTATA GCTCTTTGTC GCAATTTCAA TGCTTTAAAC     780
AATCCAAATC GCATTATATT TGTGCATGGA GGCAAATGAC GGGGTTGGAA TCTTAGATGA     840
```

-continued

```
GATCAGGAGC TTTCAGGGTA AACGCCCGGT TCATTTTGTA CCACATTTCA TCATTTTCCT    900
GTCGTCCTTG GTATCCTCAA CTTGTCCCGG TTTTGTTTTC GGTACACTCT TCCGTGATGC    960
CACCTGTCTC CGTCTCAATT ATCGTTTAGA AATGTGAACT GTCCAGATGG GTGACTCATA   1020
TTGCTGCTGC TACAATCCAC TTTCTTTTCT CATCGGCAGT CTTACGAGCC ATCATAAAC    1080
TTTTTTTTCC GCGAAATTTG CAATAAACCG GCCAAAAACT TTCTCCAAAT TGTTACGCAA   1140
TATATACAAT CCATAAGAAT ATCTTCTCAA TGTTTATGAT TTCTTCGCAG CACTTTCTCT   1200
TCGTGTGCTA ACATCTTATT TTTATAATAT TTCCGCTAAA ATTCCGATTT TTGAGTATTA   1260
ATTTATCGTA AAATTATCAT AATAGCACCG AAAACTACTA AAAATGGTAA AAGCTCCTTT   1320
TAAATCGGCT CGACATTATC GTATTAAGGA ATCACAAAAT TCTGAGAATG CGTACTGCGC   1380
AACATATTTG ACGGCAAAAT ATCTCGTAGC GAAAACTACA GTAATTCTTT AAATGACTAC   1440
TGTAGCGCTT GTGTCGATTT ACGGGCTCAA TTTTTGAAAA TAATTTTTTT TTTCGAATTT   1500
TGATAACCCG TAAATCGTCA CAACGCTACA GTAGTCATTT AAAGGATTAC TGTAGTTCTA   1560
GCTACGAGAT ATTTTGCGCG CCAAATATGA CTGTAATACG CATTCTCTGA ATTTTGTGTT   1620
TCCGTAATAA TTTCACAAGA TTTTGGCATT CCACTTTAAA GGCGCACAGG ATTTATTCCA   1680
ATGGGTCTCG GCACGCAAAA AGTTTGATAG ACTTTTAAAT TCTCCTTGCA TTTTTAATTC   1740
AATTACTAAA ATTTTCGTGA ATTTTTCTGT TAAAATTTTT AAAATCAGTT TTCTAATATT   1800
TTCCAGGCTG ACAAACAGAA ACAAAAACAC AACAAACATT TTAAAAATCA GTTTTCAAAT   1860
TAAAAATAAC GATTTCTCAT TGAAAATTGT GTTTTATGTT TGCGAAAATA AAAGAGAACT   1920
GATTCAAAAC AATTTTAACA AAAAAAAACC CCAAAATTCG CCAGAAATCA AGATAAAAAA   1980
TTCAAGAGGG TCAAAATTTT CCGATTTTAC TGACTTTCAC CTTTTTTTTC GTAGTTCAGT   2040
GCAGTTGTTG GAGTTTTTGA CGAAAACTAG GAAAAAAATC GATAAAAATT ACTCAAATCG   2100
AGCTGAATTT TGAGGACAAT GTTTAAAAAA AAACACTATT TTTCCAATAA TTTCACTCAT   2160
TTTCAGACTA AATCGAAAAT CAAATCGTAC TCTGACTACG GGTCAGTAGA GAGGTCAACC   2220
ATCAGCCGAA GATGATGCGT CAAGATAGAA GGAGCTTGCT AGAGAGGAAC ATTATGATGT   2280
TCTCTAGTCA TCTAAAAGTC GATGAAATTY TCGAAGTTCT CATCGCAAAA CAAGTGTTGA   2340
ATAGTGATAA TGGAGATATG ATTAATGTGA GTTTTTAATC GAATAATAAT TTTAAAAAAA   2400
AATTGATAAT ATAAAGAATA TTTTTGCAGT CATGTGGAAC GGTTCGCGAG AAGAGACGGG   2460
AGATCGTGAA AGCAGTGCAA CGACGGRGAG ATGTGGCGTT CGACGCGTTT TATGATGCTC   2520
TTCGCTCTAC GGGACACGAA GGACTTGCTG AAGTTCTTGA ACCTCTCGCC AGATCGTAGG   2580
TTTTTAAAGT TCGGCGCAAA AGCAAGGGTC TCACGGAAAA AAGAGGCGGA TCGTAATTTT   2640
GCAACCCACC GGCACGGTTT TTTCCTCCGA AAATCGGAAA TTATGCACTT TCCCAAATAT   2700
TTGAAGTGAA ATATATTTTA TTTACTGAAA GCTCGAGTGA TTATTTATTT TTTAACACTA   2760
ATTTTCGTGG CGCAAAAGGC CATTTTGTAG ATTTGCCGAA AATACTTGTC ACACACACAC   2820
ACACACATCT CCTTCAAATA TCCCTTTTTC CAGTGTTGAC TCGAATGCTG TCGAATTCGA   2880
GTGTCCAATG TCACCGGCAA GCCATCGTCG GAGCCGCGCA TTGAGCCCCG CCGGCTACAC   2940
TTCACCGACC CGAGTTCACC GTGACAGCGT CTCTTCAGTG TCATCATTCA CTTCTTATCA   3000
GGATATCTAC TCAAGAGCAA GATCTCGTTC TCGATCGCGT GCACTTCATT CATCGGATCG   3060
ACACAATTAT TCATCTCCTC CAGTCAACGC ATTTCCCAGC CAACCTTGTA TGTTGATGCG   3120
AACACTAAAT TCTGAGAATG CGCATTACTC AACATATTTG ACGCGCAAAT ATCTCGTAGC   3180
GAAAAATACA GTAACCCTTT AAATGACTAT TGTAGTGTCG ATTTACGGGC TCGATTTTCG   3240
```

```
AAACGAATAT ATGCTCGAAT TGTGACAACG AATTTTAATT TGTCATTTTT GTGTTTTCTT    3300

TTGATATTTT TGATCAATTA ATAAATTATT TCCGTAAACA GACACCAGCG CTACAGTACT    3360

CTTTTAAAGA GTTACAGTAG TTTTCGCTTC AAGATATTTT GAAAAGAATT TTAAACATTT    3420

TGAAAAAAAA TCATCTAACA TGTGCCAAAA CGCTTTTTTC AAGTTTCGCA GATTTTTTGA    3480

TTTTTTTCAT TCAAGATATG CTTATTAACA CATATAATTA TCATTAATGT GAATTTCTTG    3540

TAGAAATTTT GGGCTTTTCG TTCTAGTATG CTCTACTTTT GAAATTGCTC AACGAAAAAA    3600

TCATGTGGTT TGTTCATATG AATGACGAAA AATAGCAATT TTTTATATAT TTTCCCCTAT    3660

TCATGTTGTG CAGAAAAATA GTAAAAAAGC GCATGCATTT TTCGACATTT TTTACATCGA    3720

ACGACAGCTC ACTTCACATG CTGAAGACGA GAGACGCGGA GAAATACCAC ACATCTTTCT    3780

GCGTCTCTCG TCTTCAGCAT GTGAAATGGG ATCTCGGTCG ATGTAAAAAA ATGTCGAATA    3840

ATGTAAAAAA TGCATGCGTT TTTTTACACT TTTCTGCACA AATGAATAGG GGAAAAATGT    3900

ATTAAAATAC ATTTTTTGTA TTTTTCAACA TCACATGATT AACCCCATTA TTTTTTCGTT    3960

GAGCAACTTA AAAAGTAGAG AATATTAGAG CGAAAACCAA AATTTCTTCA AGATATTACC    4020

TTTATTGATA ATTATAGATG TTAATAAGCA TATCTTGAAT GAAAGTCAGC AAAAATATGT    4080

GCGAAACACC TGAAAAAAAT CAAAAATTCT GCGAAAATTG AAAAAATGCA TTAAAATACA    4140

TTTTTGCATT TTTCTACATC ACATGAATGT AGAAAATTAA AAGGGAAATC AAAATTTCTA    4200

GAGGATATAA TTGAATGAAA CATTGCGAAA TTAAAATGTG CGAAACGTCA AAAAAGAGGA    4260

AATTTGGGTA TCAAAATCGA TCCTAAAACC AACACATTTC AGCATCCGCC AACTCTTCAT    4320

TCACCGGATG CTCTTCTCTC GGATACAGTT CAAGTCGTAA TCGCTCATTC AGCAAAGCTT    4380

CTGGACCAAC TCAATACATA TTCCATGAAG AGGATATGAA CTTTGTCGAT GCACCAACCA    4440

TAAGCCGTGT TTTCGACGAG AAAACCATGT ACAGAAACTT CTCGAGTCCT CGTGGAATGT    4500

GCCTCATCAT AAATAATGAA CACTTTGAGC AGATGCCAAC ACGGAATGGT ACCAAGGCCG    4560

ACAAGGACAA TCTTACCAAT TTGTTCAGAT GCATGGGCTA TACGGTTATT TGCAAGGACA    4620

ATCTGACGGG AAGGGTACGG CGAAATTATA TTACCCAAAC GCGAAATTTG CCATTTTGCG    4680

CCGAAAATGT GGCGCCCGGT CTCGACACGA CAATTTGTGT TAAATGCAAA AATGTATAAT    4740

TTTGCAAAAA ACAAAATTTT GAACTTCCGC GAAAATGATT TACCTAGTTT CGAAATTTTC    4800

GTTTTTTCCG GCTACATTAT GTGTTTTTTC TTAGTTTTTC TATAATATTT GATGTAAAAA    4860

ACCGTTTGTA AATTTTCAGA CAATTTTCCG CATACAAAAC TTGATAGCAC GAAATCAATT    4920

TTCTGAATTT TCAAAATTAT CCAAAAATGC ACAATTTAAA ATTTGTGAAA ATTGGCAAAC    4980

GGTGTTTCAA TATGAAATGT ATTTTTAAAA ACTTTAAAAA CCACTCCGGA AAAGCAATAA    5040

AAATCAAAAC AACGTCACAA TTCAAATTCA AAAGTTATTC ATCCGATTTG TTTATTTTTG    5100

CAAAATTTGA AAAAATCATG AAGGATTTAG AAAAGTTTTA TAACATTTTT TCTAGATTTT    5160

TCAAAATTTT TTTTAACAAA TCGAGAAAAA GAGAATGAAA AATCGATTTT AAAAATATCC    5220

ACAGCTTCGA GAGTTTGAAA TTACAGTACT CCTTAAAGGC GCACACCCCA TTTGCATTGG    5280

ACCAAAAATT TGTCGTGTCG AGACCAGGTA CCGTAGTTTT TGTCGCAAAA ATTGCACCAT    5340

TGGACAATAA ACCTTCCTAA TCACCAAAAA GTAAAATTGA AATCTTCGAA AAGCCAAAAA    5400

ATTCAAAAAA AAAGTCGAAT TTCGATTTTT TTTTTGGTTT TTTGGTCCCA AAAACCAAAA    5460

AAATCAATTT TCTGCAAAAT ACCAAAAAGA AACCCGAAAA AATTTCCCAG CCTTGTTCCT    5520

AATGTAAACT GATATTTAAT TTCCAGGGAA TGCTCCTGAC AATTCGAGAC TTTGCCAAAC    5580

ACGAATCACA CGGAGATTCT GCGATACTCG TGATTCTATC ACACGGAGAA GAGAATGTGA    5640
```

-continued

```
TTATTGGAGT TGATGATATA CCGATTAGTA CACACGAGAT ATATGATCTT CTCAACGCGG      5700

CAAATGCTCC CCGTCTGGCG AATAAGCCGA AAATCGTTTT TGTGCAGGCT TGTCGARGCG      5760

GTTCGTTTTT TATTTTAATT TTAATATAAA TATTTTAAAT AAATTCATTT TCAGAACGTC      5820

GTGACAATGG ATTCCCAGTC TTGGATTCTG TCGACGGAGT TCCTGCATTT CTTCGTCGTG      5880

GATGGGACAA TCGAGACGGG CCATTGTTCA ATTTTCTTGG ATGTGTGCGG CCGCAAGTTY      5940

AGGTTGCAAT TTAATTTCTT GAATGAGAAT ATTCCTTCAA AAAATCTAAA ATAGATTTTT      6000

ATTCCAGAAA GTCCCGATCG AAAAATTGCG ATATAATTAC GAAATTTGTG ATAAAATGAC      6060

AAACCAATCA GCATCGTCGA TCTCCGCCCA CTTCATCGGA TTGGTTTGAA AGTGGGCGGA      6120

GTGAATTGCT GATTGGTCGC AGTTTTCAGT TTAGAGGGAA TTTAAAAATC GCCTTTTCGA      6180

AAATTAAAAA TTGATTTTTT CAATTTTTTC GAAAAATATT CCGATTATTT TATATTCTTT      6240

GGAGCGAAAG CCCCGTCCTG TAAACATTTT TAAATGATAA TTAATAAATT TTTGCARCAA      6300

GTGTGGAGAA AGAAGCCGAG CYAAGCTGAC ATTCTGATTC GRTACGCAAC GACAGCTCAA      6360

TATGTTTCGT GGAGAAACAG TGCTCGTGGA TCATGGTTCA TTCAAGCCGT CTGTGAAGTG      6420

TTCTCGACAC ACGYAAAGGA TATGGATGTT GTTGAGCTGC TGACTGAAGT CAATAAGAAG      6480

GTCGYTTGTG GATTTCAGAC ATCACAGGGA TCGAATATTT TGAAACAGAT GCCARAGGTA      6540

CTTGAAACAA ACAATGCATG TCTAACTTTT AAGGACACAG AAAAATAGGC AGAGGCTCCT      6600

TTTGCAAGCC TGCCGCGCGT CAACCTAGAA TTTTAGTTTT TAGCTAAAAT GATTGATTTT      6660

GAATATTTTA TGCTAATTTT TTTGCGTTAA ATTTGAAAT AGTCACTATT TATCGGGTTT      6720

CCAGTAAAAA ATGTTTATTA GCCATTGGAT TTTACTGAAA ACGAAAATTT GTAGTTTTTC      6780

AACGAAATTT ATCGATTTTT AAATGTAAAA AAAAATAGCG AAAATTACAT CAACCATCAA      6840

GCATTTAAGC CAAAATTGTT AACTCATTTA AAAATTAATT CAAAGTTGTC CACGAGTATT      6900

ACACGGTTGG CGCGCGGCAA GTTTGCAAAA CGACGCTCCG CCTCTTTTTC TGTGCGGCTT      6960

GAAAACAAGG GATCGGTTTA GATTTTTCCC CAAAATTTAA ATTAAATTTC AGATGACATY      7020

CCGCCTGCTC AAAAAGTTCT ACTTTTGGCC GGAAGCACGA AACTCTGCCG TCTAAAATTC      7080

ACTCGTGATT CATTGCCCAA TTGATAATTG TCTGTATCTT CTCCCCCAGT TCTCTTTCGC      7140

CCAATTAGTT TAAAACCATG TGTATATTGT TATCCTATAC TCATTTCACT TTATCATTCT      7200

ATCATTTCTC TTCCCATTTT CACACATTTC CATTTCTCTA CGATAATCTA AAATTATGAC      7260

GTTTGTGTCT CGAACGCATA ATAATTTTAA TAACTCGTTT TGAATTGAT TAGTTGTTGT      7320

GCCCAGTATA TATGTATGTA CTATGCTTCT ATCAACAAAA TAGTTTCATA GATCATCACC      7380

CCAACCCCAC CAACCTACCG TACCATATTC ATTTTTGCCG GGAATCAATT TCGATTAATT      7440

TTAACCTATT TTTTCGCCAC AAAAAATCTA ATATTTGAAT TAACGAATAG CATTCCCATC      7500

TCTCCCGTGC CGGAATGCCT CCCGGCCTTT TAAAGTTCGG AACATTTGGC AATTATGTAT      7560

AAATTTGTAG GTCCCCCCCA TCATTTCCCG CCCATCATCT CAAATTGCAT TCTTTTTTCG      7620

CCGTGATATC CCGATTCTGG TCAGCAAAGA TCT                                  7653
```

(2) INFORMATION FOR SEQ ID NO:2:

(i) SEQUENCE CHARACTERISTICS:
        (A) LENGTH: 503 amino acids
        (B) TYPE: amino acid
        (C) STRANDEDNESS: single
        (D) TOPOLOGY: linear (ii) MOLECULE TYPE: protein (ix) FEATURE:

(xi) SEQUENCE DESCRIPTION: SEQ ID NO:2:

```
Met Met Arg Gln Asp Arg Arg Ser Leu Leu Glu Arg Asn Ile Met Met
 1               5                  10                  15

Phe Ser Ser His Leu Lys Val Asp Glu Ile Xaa Glu Val Leu Ile Ala
            20                  25                  30

Lys Gln Val Leu Asn Ser Asp Asn Gly Asp Met Ile Asn Ser Cys Gly
        35                  40                  45

Thr Val Arg Glu Lys Arg Arg Glu Ile Val Lys Ala Val Gln Arg Arg
    50                  55                  60

Xaa Asp Val Ala Phe Asp Ala Phe Tyr Asp Ala Leu Arg Ser Thr Gly
65                  70                  75                  80

His Glu Gly Leu Ala Glu Val Leu Glu Pro Leu Ala Arg Ser Val Asp
                85                  90                  95

Ser Asn Ala Val Glu Phe Glu Cys Pro Met Ser Pro Ala Ser His Arg
            100                 105                 110

Arg Ser Arg Ala Leu Ser Pro Ala Gly Tyr Thr Ser Pro Thr Arg Val
        115                 120                 125

His Arg Asp Ser Val Ser Ser Val Ser Ser Phe Thr Ser Tyr Gln Asp
    130                 135                 140

Ile Tyr Ser Arg Ala Arg Ser Arg Ser Arg Ala Leu His Ser
145                 150                 155                 160

Ser Asp Arg His Asn Tyr Ser Pro Pro Val Asn Ala Phe Pro Ser
            165                 170                 175

Gln Pro Ser Ser Ala Asn Ser Ser Phe Thr Gly Cys Ser Ser Leu Gly
        180                 185                 190

Tyr Ser Ser Arg Asn Arg Ser Phe Ser Lys Ala Ser Gly Pro Thr
    195                 200                 205

Gln Tyr Ile Phe His Glu Glu Asp Met Asn Phe Val Asp Ala Pro Thr
    210                 215                 220

Ile Ser Arg Val Phe Asp Glu Lys Thr Met Tyr Arg Asn Phe Ser Ser
225                 230                 235                 240

Pro Arg Gly Met Cys Leu Ile Ile Asn Asn Glu His Phe Glu Gln Met
                245                 250                 255

Pro Thr Arg Asn Gly Thr Lys Ala Asp Lys Asp Asn Leu Thr Asn Leu
            260                 265                 270

Phe Arg Cys Met Gly Tyr Thr Val Ile Cys Lys Asp Asn Leu Thr Gly
        275                 280                 285

Arg Gly Met Leu Leu Thr Ile Arg Asp Phe Ala Lys His Glu Ser His
    290                 295                 300

Gly Asp Ser Ala Ile Leu Val Ile Leu Ser His Gly Glu Glu Asn Val
305                 310                 315                 320

Ile Ile Gly Val Asp Asp Ile Pro Ile Ser Thr His Glu Ile Tyr Asp
                325                 330                 335

Leu Leu Asn Ala Ala Asn Ala Pro Arg Leu Ala Asn Lys Pro Lys Ile
            340                 345                 350

Val Phe Val Gln Ala Cys Arg Xaa Glu Arg Arg Asp Asn Gly Phe Pro
        355                 360                 365

Val Leu Asp Ser Val Asp Gly Val Pro Ala Phe Leu Arg Arg Gly Trp
    370                 375                 380

Asp Asn Arg Asp Gly Pro Leu Phe Asn Phe Leu Gly Cys Val Arg Pro
385                 390                 395                 400

Gln Val Xaa Gln Val Trp Arg Lys Lys Pro Ser Xaa Ala Asp Ile Leu
```

```
                     405                410                415
Ile Arg Tyr Ala Thr Thr Ala Gln Tyr Val Ser Xaa Arg Asn Ser Ala
                420                425                430

Arg Gly Ser Trp Phe Ile Gln Ala Val Cys Glu Val Phe Ser Thr His
            435                440                445

Xaa Lys Asp Met Asp Val Val Glu Leu Leu Thr Glu Val Asn Lys Lys
        450                455                460

Val Xaa Cys Gly Phe Gln Thr Ser Gln Gly Ser Asn Ile Leu Lys Gln
465                470                475                480

Met Pro Xaa Met Thr Xaa Arg Leu Leu Lys Lys Phe Tyr Phe Trp Pro
            485                490                495

Glu Ala Arg Asn Ser Ala Val
                500
```

(2) INFORMATION FOR SEQ ID NO:3:

(i) SEQUENCE CHARACTERISTICS:
        (A) LENGTH: 1373 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 18...1229
        (D) OTHER INFORMATION: /product= "human interleukin-1 beta
            convertase"

(xi) SEQUENCE DESCRIPTION: SEQ ID NO:3:

```
AAAGGAGAG AAAAGCC ATG GCC GAC AAG GTC CTG AAG GAG AAG AGA AAG          50
                   Met Ala Asp Lys Val Leu Lys Glu Lys Arg Lys
                     1               5                  10

CTG TTT ATC CGT TCC ATG GGT GAA GGT ACA ATA AAT GGC TTA CTG GAT        98
Leu Phe Ile Arg Ser Met Gly Glu Gly Thr Ile Asn Gly Leu Leu Asp
            15                  20                  25

GAA TTA TTA CAG ACA AGG GTG CTG AAC AAG GAA GAG ATG GAG AAA GTA       146
Glu Leu Leu Gln Thr Arg Val Leu Asn Lys Glu Glu Met Glu Lys Val
        30                  35                  40

AAA CGT GAA AAT GCT ACA GTT ATG GAT AAG ACC CGA GCT TTG ATT GAC       194
Lys Arg Glu Asn Ala Thr Val Met Asp Lys Thr Arg Ala Leu Ile Asp
    45                  50                  55

TCC GTT ATT CCG AAA GGG GCA CAG GCA TGC CAA ATT TGC ATC ACA TAC       242
Ser Val Ile Pro Lys Gly Ala Gln Ala Cys Gln Ile Cys Ile Thr Tyr
60                  65                  70                  75

ATT TGT GAA GAA GAC AGT TAC CTG GCA GGG ACG CTG GGA CTC TCA GCA       290
Ile Cys Glu Glu Asp Ser Tyr Leu Ala Gly Thr Leu Gly Leu Ser Ala
                80                  85                  90

GAT CAA ACA TCT GGA AAT TAC CTT AAT ATG CAA GAC TCT CAA GGA GTA       338
Asp Gln Thr Ser Gly Asn Tyr Leu Asn Met Gln Asp Ser Gln Gly Val
            95                 100                 105

CTT TCT TCC TTT CCA GCT CCT CAG GCA GTG CAG GAC AAC CCA GCT ATG       386
Leu Ser Ser Phe Pro Ala Pro Gln Ala Val Gln Asp Asn Pro Ala Met
       110                 115                 120

CCC ACA TCC TCA GGC TCA GAA GGG AAT GTC AAG CTT TGC TCC CTA GAA       434
Pro Thr Ser Ser Gly Ser Glu Gly Asn Val Lys Leu Cys Ser Leu Glu
   125                 130                 135

GAA GCT CAA AGG ATA TGG AAA CAA AAG TCG GCA GAG ATT TAT CCA ATA       482
Glu Ala Gln Arg Ile Trp Lys Gln Lys Ser Ala Glu Ile Tyr Pro Ile
140                 145                 150                 155

ATG GAC AAG TCA AGC CGC ACA CGT CTT GCT CTC ATT ATC TGC AAT GAA       530
```

```
            Met Asp Lys Ser Ser Arg Thr Arg Leu Ala Leu Ile Ile Cys Asn Glu
                        160                 165                 170

GAA TTT GAC AGT ATT CCT AGA AGA ACT GGA GCT GAG GTT GAC ATC ACA              578
Glu Phe Asp Ser Ile Pro Arg Arg Thr Gly Ala Glu Val Asp Ile Thr
                175                 180                 185

GGC ATG ACA ATG CTG CTA CAA AAT CTG GGG TAC AGC GTA GAT GTG AAA              626
Gly Met Thr Met Leu Leu Gln Asn Leu Gly Tyr Ser Val Asp Val Lys
                190                 195                 200

AAA AAT CTC ACT GCT TCG GAC ATG ACT ACA GAG CTG GAG GCA TTT GCA              674
Lys Asn Leu Thr Ala Ser Asp Met Thr Thr Glu Leu Glu Ala Phe Ala
            205                 210                 215

CAC CGC CCA GAG CAC AAG ACC TCT GAC AGC ACG TTC CTG GTG TTC ATG              722
His Arg Pro Glu His Lys Thr Ser Asp Ser Thr Phe Leu Val Phe Met
220                 225                 230                 235

TCT CAT GGT ATT CGG GAA GGC ATT TGT GGG AAG AAA CAC TCT GAG CAA              770
Ser His Gly Ile Arg Glu Gly Ile Cys Gly Lys Lys His Ser Glu Gln
                240                 245                 250

GTC CCA GAT ATA CTA CAA CTC AAT GCA ATC TTT AAC ATG TTG AAT ACC              818
Val Pro Asp Ile Leu Gln Leu Asn Ala Ile Phe Asn Met Leu Asn Thr
                255                 260                 265

AAG AAC TGC CCA AGT TTG AAG GAC AAA CCG AAG GTG ATC ATC ATC CAG              866
Lys Asn Cys Pro Ser Leu Lys Asp Lys Pro Lys Val Ile Ile Ile Gln
                270                 275                 280

GCC TGC CGT GGT GAC AGC CCT GGT GTG GTG TGG TTT AAA GAT TCA GTA              914
Ala Cys Arg Gly Asp Ser Pro Gly Val Val Trp Phe Lys Asp Ser Val
            285                 290                 295

GGA GTT TCT GGA AAC CTA TCT TTA CCA ACT ACA GAA GAG TTT GAG GAT              962
Gly Val Ser Gly Asn Leu Ser Leu Pro Thr Thr Glu Glu Phe Glu Asp
300                 305                 310                 315

GAT GCT ATT AAG AAA GCC CAC ATA GAG AAG GAT TTT ATC GCT TTC TGC             1010
Asp Ala Ile Lys Lys Ala His Ile Glu Lys Asp Phe Ile Ala Phe Cys
                320                 325                 330

TCT TCC ACA CCA GAT AAT GTT TCT TGG AGA CAT CCC ACA ATG GGC TCT             1058
Ser Ser Thr Pro Asp Asn Val Ser Trp Arg His Pro Thr Met Gly Ser
                335                 340                 345

GTT TTT ATT GGA AGA CTC ATT GAA CAT ATG CAA GAA TAT GCC TGT TCC             1106
Val Phe Ile Gly Arg Leu Ile Glu His Met Gln Glu Tyr Ala Cys Ser
            350                 355                 360

TGT GAT GTG GAG GAA ATT TTC CGC AAG GTT CGA TTT TCA TTT GAG CAG             1154
Cys Asp Val Glu Glu Ile Phe Arg Lys Val Arg Phe Ser Phe Glu Gln
365                 370                 375

CCA GAT GGT AGA GCG CAG ATG CCC ACC ACT GAA AGA GTG ACT TTG ACA             1202
Pro Asp Gly Arg Ala Gln Met Pro Thr Thr Glu Arg Val Thr Leu Thr
                380                 385                 390                 395

AGA TGT TTC TAC CTC TTC CCA GGA CAT TAAAATAAGG AAACTGTATG AATGTCT           1256
Arg Cys Phe Tyr Leu Phe Pro Gly His
                400

GCGGGCAGGA AGTGAAGAGA TCGTTCTGTA AAAGGTTTTT GGAATTATGT CTGCTGAATA           1316

ATAAACTTTT TTTGAAATAA TAAATCTGGT AGAAAAATGA AAAAAAAAA AAAAAAA              1373

(2) INFORMATION FOR SEQ ID NO:4:

(i) SEQUENCE CHARACTERISTICS:
        (A) LENGTH: 404 amino acids
        (B) TYPE: amino acid
        (C) STRANDEDNESS: single
        (D) TOPOLOGY: linear (ii) MOLECULE TYPE: protein (ix) FEATURE:
```

(xi) SEQUENCE DESCRIPTION: SEQ ID NO:4:

```
Met Ala Asp Lys Val Leu Lys Glu Lys Arg Lys Leu Phe Ile Arg Ser
 1               5                  10                  15

Met Gly Glu Gly Thr Ile Asn Gly Leu Xaa Asp Glu Leu Leu Gln Thr
            20                  25                  30

Arg Val Leu Asn Lys Glu Glu Met Glu Lys Val Lys Arg Glu Asn Ala
         35                  40                  45

Thr Val Met Asp Lys Thr Arg Ala Leu Ile Asp Ser Val Ile Pro Lys
 50                  55                  60

Xaa Ala Gln Ala Cys Gln Ile Cys Ile Thr Tyr Ile Cys Glu Glu Asp
 65                  70                  75                  80

Ser Tyr Leu Ala Gly Thr Leu Gly Leu Ser Ala Asp Gln Thr Ser Gly
                 85                  90                  95

Asn Tyr Leu Asn Met Gln Asp Ser Gln Gly Val Leu Ser Ser Phe Pro
            100                 105                 110

Ala Pro Gln Ala Val Gln Asp Asn Pro Ala Met Pro Thr Ser Ser Gly
         115                 120                 125

Ser Glu Gly Asn Val Lys Leu Cys Ser Leu Glu Glu Ala Gln Arg Ile
130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Glu Glu Phe Asp Ser Ile
                165                 170                 175

Pro Arg Arg Thr Gly Ala Glu Val Asp Ile Thr Gly Met Thr Met Leu
            180                 185                 190

Leu Gln Asn Leu Gly Tyr Ser Val Asp Val Lys Lys Asn Leu Thr Ala
         195                 200                 205

Ser Asp Met Thr Thr Glu Leu Glu Ala Phe Ala His Arg Pro Glu His
210                 215                 220

Lys Thr Ser Asp Ser Thr Phe Leu Val Phe Met Ser His Gly Ile Arg
225                 230                 235                 240

Glu Gly Ile Cys Gly Lys Lys His Ser Glu Gln Val Pro Asp Ile Leu
                245                 250                 255

Gln Leu Asn Ala Ile Phe Asn Met Leu Asn Thr Lys Asn Cys Pro Ser
            260                 265                 270

Leu Lys Asp Lys Pro Lys Val Ile Ile Ile Gln Ala Xaa Arg Xaa Asp
         275                 280                 285

Ser Pro Gly Val Val Trp Phe Lys Asp Ser Val Gly Val Ser Gly Asn
290                 295                 300

Leu Ser Leu Pro Thr Thr Glu Glu Phe Glu Asp Asp Ala Ile Lys Lys
305                 310                 315                 320

Ala His Ile Xaa Lys Asp Phe Ile Ala Phe Cys Ser Ser Thr Pro Asp
                325                 330                 335

Asn Val Ser Xaa Arg His Pro Thr Met Gly Ser Val Phe Ile Gly Arg
            340                 345                 350

Leu Ile Glu His Met Gln Glu Tyr Xaa Cys Ser Cys Asp Val Glu Glu
         355                 360                 365

Ile Phe Arg Lys Val Arg Phe Ser Phe Glu Gln Pro Asp Gly Arg Ala
370                 375                 380

Gln Met Pro Thr Thr Xaa Arg Val Xaa Leu Thr Arg Cys Phe Tyr Leu
385                 390                 395                 400

Phe Pro Gly His
```

(2) INFORMATION FOR SEQ ID NO:5:

(i) SEQUENCE CHARACTERISTICS:
        (A) LENGTH: 505 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Met Arg Gln Asp Arg Trp Leu Leu Glu Arg Asn Ile Leu Glu Phe
 1               5                  10                  15

Ser Ser Lys Leu Gln Ala Asp Leu Ile Leu Asp Val Leu Ile Ala Lys
            20                  25                  30

Gln Val Leu Asn Ser Asp Asn Gly Asp Val Ile Asn Ser Cys Arg Thr
        35                  40                  45

Glu Arg Asp Asn Glu Lys Glu Ile Val Lys Ala Val Gln Arg Arg Gly
    50                  55                  60

Asp Glu Ala Phe Asp Ala Phe Tyr Asp Ala Leu Arg Asp Thr Gly His
65                  70                  75                  80

Asn Asp Leu Ala Asp Val Leu Met Pro Leu Ser Arg Pro Xaa Xaa Xaa
                85                  90                  95

Asn Pro Val Pro Met Glu Cys Pro Met Ser Pro Ser Ser His Arg Arg
            100                 105                 110

Ser Arg Ala Leu Ser Pro Pro Xaa Tyr Ala Ser Pro Thr Arg Val His
        115                 120                 125

Arg Asp Ser Ile Ser Ser Val Ser Ser Phe Thr Ser Thr Tyr Gln Asp
    130                 135                 140

Val Tyr Ser Arg Ala Arg Ser Ser Arg Ser Ser Arg Pro Leu Gln
145                 150                 155                 160

Ser Ser Asp Arg His Asn Tyr Met Ser Ala Ala Thr Ser Phe Pro Ser
                165                 170                 175

Gln Pro Xaa Ser Ala Asn Ser Ser Phe Thr Gly Cys Ala Ser Leu Gly
            180                 185                 190

Tyr Ser Ser Arg Asn Arg Ser Phe Ser Lys Thr Ser Ala Gln Ser
        195                 200                 205

Gln Tyr Ile Phe His Glu Glu Asp Met Asn Tyr Val Asp Ala Pro Thr
    210                 215                 220

Ile His Arg Val Phe Asp Glu Lys Thr Met Tyr Arg Asn Phe Ser Ser
225                 230                 235                 240

Pro Arg Gly Leu Cys Leu Ile Ile Asn Asn Glu His Phe Glu Gln Met
                245                 250                 255

Pro Thr Arg Asn Gly Thr Lys Ala Asp Lys Asp Asn Leu Thr Asn Ile
            260                 265                 270

Phe Arg Cys Met Gly Tyr Thr Val Ile Cys Lys Asp Asn Leu Thr Gly
        275                 280                 285

Arg Glu Met Leu Ser Thr Ile Arg Ser Phe Gly Arg Asn Asp Met His
    290                 295                 300

Gly Asp Ser Ala Ile Leu Val Ile Leu Ser His Gly Glu Xaa Asn Val
305                 310                 315                 320

Ile Ile Gly Val Asp Asp Val Ser Val Asn Val His Glu Ile Tyr Asp
                325                 330                 335

Leu Leu Asn Ala Ala Asn Ala Pro Arg Leu Ala Asn Lys Pro Lys Leu
            340                 345                 350

Val Phe Val Gln Ala Cys Arg Gly Glu Arg Arg Asp Asn Gly Phe Pro
        355                 360                 365
```

```
Val Leu Asp Ser Val Asp Gly Val Pro Ser Leu Ile Arg Arg Gly Trp
    370                 375                 380

Asp Asn Arg Asp Gly Pro Leu Phe Asn Phe Leu Gly Cys Val Arg Pro
385                 390                 395                 400

Gln Val Gln Gln Val Trp Arg Lys Lys Pro Ser Gln Ala Asp Met Leu
                405                 410                 415

Ile Ala Tyr Ala Thr Thr Ala Gln Tyr Val Ser Trp Arg Asn Ser Ala
            420                 425                 430

Arg Gly Ser Trp Phe Ile Gln Ala Val Cys Glu Val Phe Ser Leu His
        435                 440                 445

Ala Lys Asp Met Asp Val Val Glu Leu Leu Thr Glu Val Asn Lys Lys
    450                 455                 460

Val Ala Cys Gly Phe Gln Thr Ser Gln Gly Ser Asn Ile Leu Lys Gln
465                 470                 475                 480

Met Pro Glu Leu Thr Ser Arg Leu Leu Lys Lys Phe Tyr Phe Trp Pro
                485                 490                 495

Glu Asp Arg Gly Arg Asn Ser Ala Val
                500                 505
```

(2) INFORMATION FOR SEQ ID NO:6:

(i) SEQUENCE CHARACTERISTICS:
        (A) LENGTH: 479 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Thr Val Ser Leu Ser Leu Ile Ile Ala Arg Gln Val Leu Asn Ser Asp
1               5                   10                  15

Asn Gly Asp Met Ile Asn Ser Cys Arg Thr Glu Arg Asp Asn Glu Lys
                20                  25                  30

Glu Ile Val Lys Ala Val Gln Arg Gly Asp Glu Ala Phe Asp Ala
            35                  40                  45

Phe Tyr Asp Ala Leu Arg Asp Thr Gly His Asn Asp Leu Ala Asp Val
50                  55                  60

Leu Met Pro Leu Ser Arg Pro Val Asp Ser Asn Pro Val Pro Met Glu
65                  70                  75                  80

Cys Pro Met Ser Pro Ser Ser His Arg Arg Ser Arg Ala Leu Ser Pro
                85                  90                  95

Pro Xaa Tyr Ala Ser Pro Thr Arg Val His Arg Asp Ser Ile Ser Ser
            100                 105                 110

Val Ser Ser Phe Thr Ser Thr Tyr Gln Asp Val Tyr Ser Arg Ala Thr
            115                 120                 125

Ser Ser Ser Pro Leu Gln Thr Ser Asp Arg His Asn Tyr Val Ser Ala
            130                 135                 140

Ser Thr Ser Phe Gln Ser Gln Pro Ala Ser Ala Asn Ser Ser Phe Thr
145                 150                 155                 160

Gly Ser Ala Ser Leu Gly Tyr Ser Ser Arg Thr Arg Ser Tyr Ser
                165                 170                 175

Lys Thr Ser Ala His Ser Gln Tyr Ile Phe His Glu Glu Asp Met Asn
            180                 185                 190

Tyr Val Asp Ala Pro Thr Ile His Arg Val Phe Asp Glu Lys Thr Met
            195                 200                 205
```

-continued

```
Tyr Arg Asn Phe Ser Thr Pro Arg Gly Leu Cys Leu Ile Ile Asn Asn
    210                 215                 220

Glu His Phe Glu Gln Met Pro Thr Arg Asn Gly Thr Lys Pro Asp Lys
225                 230                 235                 240

Asp Asn Ile Ser Asn Ile Phe Arg Cys Met Gly Tyr Ile Val His Cys
                245                 250                 255

Lys Asp Asn Leu Thr Gly Arg Glu Met Met Ser Thr Ile Arg Ser Phe
                260                 265                 270

Gly Arg Asn Asp Thr His Gly Asp Ser Ala Ile Leu Val Ile Leu Ser
                275                 280                 285

His Gly Glu Xaa Asn Val Ile Ile Gly Val Asp Asp Val Ser Val Asn
290                 295                 300

Val His Glu Ile Tyr Xaa Leu Leu Asn Ala Ala Asn Ala Pro Arg Leu
305                 310                 315                 320

Ala Asn Lys Pro Lys Leu Val Phe Val Gln Ala Cys Arg Gly Glu Arg
                325                 330                 335

Arg Asp Val Gly Phe Pro Val Leu Asp Ser Val Asp Gly Val Pro Ser
                340                 345                 350

Leu Ile Arg Arg Gly Trp Asp Lys Gly Asp Gly Pro Leu Phe Asn Phe
                355                 360                 365

Leu Gly Cys Val Arg Pro Gln Ala Gln Gln Val Trp Arg Lys Lys Pro
370                 375                 380

Ser Gln Ala Asp Met Leu Ile Ala Tyr Ala Thr Thr Ala Gln Tyr Val
385                 390                 395                 400

Ser Trp Arg Asn Ser Ala Arg Gly Ser Trp Phe Ile Gln Ala Val Cys
                405                 410                 415

Glu Val Phe Ser Leu His Ala Lys Asp Met Asp Val Val Glu Leu Leu
                420                 425                 430

Thr Glu Val Asn Lys Lys Val Ala Cys Gly Phe Gln Thr Ser Gln Gly
                435                 440                 445

Ala Asn Ile Leu Lys Gln Met Pro Glu Leu Thr Ser Arg Leu Leu Lys
450                 455                 460

Lys Phe Tyr Phe Trp Pro Glu Asp Arg Asn Arg Ser Ser Ala Val
465                 470                 475
```

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:7:

TCATCGACTT TTAGATGACT AGAGAACATC     30

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:8:

GTTGCACTGC TTTCACGATC TCCCGTCTCT     30

(2) INFORMATION FOR SEQ ID NO:9:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:9:

GTTTAATTAC CCAAGTTTGA G                                              21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:10:

GGTTTTAACC AGTTACTCAA G                                              21

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:11:

CCGGTGACAT TGGACACTC                                                 19

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:12:

ACTATTCAAC ACTTG                                                     15

(2) INFORMATION FOR SEQ ID NO:13:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: protein (ix) FEATURE:
        (D) OTHER INFORMATION: Xaa at position 117 is Ala or Val.

(xi) SEQUENCE DESCRIPTION: SEQ ID NO:13:

Met Leu Thr Val Gln Val Tyr Arg Thr Ser Gln Lys Cys Ser Ser
1               5                   10                  15

Lys His Val Val Glu Val Leu Leu Asp Pro Leu Gly Thr Ser Phe Cys
                20                  25                  30

Ser Leu Leu Pro Pro Pro Leu Leu Leu Tyr Glu Thr Asp Arg Gly Val
            35                  40                  45

Asp Gln Gln Asp Gly Lys Asn His Thr Gln Ser Pro Gly Cys Glu Glu
        50                  55                  60

Ser Asp Ala Gly Lys Glu Glu Leu Met Lys Met Arg Leu Pro Thr Arg
65                  70                  75                  80

```
Ser Asp Met Ile Cys Gly Tyr Ala Cys Leu Lys Gly Asn Ala Ala Met
                85                  90                  95

Arg Asn Thr Lys Arg Gly Ser Trp Tyr Ile Glu Ala Leu Thr Gln Val
            100                 105                 110

Phe Ser Glu Arg Xaa Cys Asp Met His Val Ala Asp Met Leu Val Lys
            115                 120                 125

Val Asn Ala Leu Ile Lys Glu Arg Gly Tyr Ala Pro Gly Thr Glu
        130                 135                 140

Phe His Arg Cys Lys Glu Met Ser Glu Tyr Cys Ser Thr Leu Cys Gln
145                 150                 155                 160

Gln Leu Tyr Leu Phe Pro Gly Tyr Pro Pro Thr
                165                 170
```

(2) INFORMATION FOR SEQ ID NO:14:

(i) SEQUENCE CHARACTERISTICS:
        (A) LENGTH: 402 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
Met Ala Asp Lys Ile Leu Arg Ala Lys Arg Lys Gln Phe Ile Asn Ser
 1               5                  10                  15

Val Ser Ile Gly Thr Ile Asn Gly Leu Leu Asp Glu Leu Leu Glu Lys
            20                  25                  30

Arg Val Leu Asn Gln Glu Glu Met Asp Lys Ile Lys Leu Ala Asn Ile
        35                  40                  45

Thr Ala Met Asp Lys Ala Arg Asp Leu Cys Asp His Val Ser Lys Lys
 50                  55                  60

Gly Pro Gln Ala Ser Gln Ile Phe Ile Thr Tyr Ile Cys Asn Glu Asp
65                  70                  75                  80

Cys Tyr Leu Ala Gly Ile Leu Glu Leu Gln Ser Ala Pro Ser Ala Glu
                85                  90                  95

Thr Phe Val Ala Thr Glu Asp Ser Lys Gly Gly His Pro Ser Ser Ser
            100                 105                 110

Glu Thr Lys Glu Glu Gln Asn Lys Glu Asp Gly Thr Phe Pro Gly Leu
        115                 120                 125

Thr Gly Thr Leu Lys Phe Cys Pro Leu Glu Lys Ala Gln Lys Leu Trp
        130                 135                 140

Lys Glu Asn Pro Ser Glu Ile Tyr Pro Ile Met Asn Thr Thr Thr Arg
145                 150                 155                 160

Thr Arg Leu Ala Leu Ile Ile Cys Asn Thr Glu Phe Gln His Leu Ser
                165                 170                 175

Pro Arg Val Gly Ala Gln Val Asp Leu Arg Glu Met Lys Leu Leu Leu
            180                 185                 190

Glu Asp Leu Gly Tyr Thr Val Lys Val Lys Glu Asn Leu Thr Ala Leu
        195                 200                 205

Glu Met Val Lys Glu Val Lys Glu Phe Ala Ala Cys Pro Glu His Lys
    210                 215                 220

Thr Ser Asp Ser Thr Phe Leu Val Phe Met Ser His Gly Ile Gln Glu
225                 230                 235                 240

Gly Ile Cys Gly Thr Thr Tyr Ser Asn Glu Val Ser Asp Ile Leu Lys
                245                 250                 255

Val Asp Thr Ile Phe Gln Met Met Asn Thr Leu Lys Cys Pro Ser Leu
```

```
                260                 265                 270
Lys Asp Lys Pro Lys Val Ile Ile Ile Gln Ala Cys Arg Gly Glu Lys
            275                 280                 285

Gln Gly Val Val Leu Leu Lys Asp Ser Val Arg Asp Ser Glu Glu Asp
290                 295                 300

Phe Leu Thr Asp Ala Ile Phe Glu Asp Asp Gly Ile Lys Lys Ala His
305                 310                 315                 320

Ile Glu Lys Asp Phe Ile Ala Phe Cys Ser Ser Thr Pro Asp Asn Val
                325                 330                 335

Ser Trp Arg His Pro Val Arg Gly Ser Leu Phe Ile Glu Ser Leu Ile
            340                 345                 350

Lys His Met Lys Glu Tyr Ala Trp Ser Cys Asp Leu Glu Asp Ile Phe
            355                 360                 365

Arg Lys Val Arg Phe Ser Phe Glu Gln Pro Glu Phe Arg Leu Gln Met
370                 375                 380

Pro Thr Ala Asp Arg Val Thr Leu Thr Lys Arg Phe Tyr Leu Phe Pro
385                 390                 395                 400

Gly His
```

(2) INFORMATION FOR SEQ ID NO:15:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa at position 3 is Ala, His, Gln,
            Lys, Phe, Cha or Asp.

(xi) SEQUENCE DESCRIPTION: SEQ ID NO:15:

Tyr Val Xaa Asp
1

(2) INFORMATION FOR SEQ ID NO:16:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Peptide has an acetyl group at the
            amino terminus and an aldehyde group at the carboxyl
            terminus.

(xi) SEQUENCE DESCRIPTION: SEQ ID NO:16:

Tyr Val Ala Asp
1

(2) INFORMATION FOR SEQ ID NO:17:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Tyr Val Ala Asp
1

(2) INFORMATION FOR SEQ ID NO:18:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa at position 2 is D-Ala.  Peptide
            has an acetyl group at the amino terminus and an
            aldehyde group at the carboxyl terminus.

(xi) SEQUENCE DESCRIPTION: SEQ ID NO:18:

Tyr Xaa Ala Asp
1

(2) INFORMATION FOR SEQ ID NO:19:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Peptide has an acetyl group at the
            amino terminus and an aldehyde group at the carboxyl
            terminus.

(xi) SEQUENCE DESCRIPTION: SEQ ID NO:19:

Tyr Val Lys Asp
1

(2) INFORMATION FOR SEQ ID NO:20:

(i) SEQUENCE CHARACTERISTICS:
        (A) LENGTH: 354 amino acids
        (B) TYPE: amino acid
        (C) STRANDEDNESS: single
        (D) TOPOLOGY: linear (ii) MOLECULE TYPE: protein (v) FRAGMENT TYPE: C-terminal (xi) SEQUENCE DESCRIPTION: SEQ ID NO:20:

Arg Ser Arg Ser Arg Ser Arg Ala Leu His Ser Ser Asp Arg His Asn
1               5                   10                  15

Tyr Ser Ser Pro Pro Val Asn Ala Phe Pro Ser Gln Pro Ser Ser Ala
                20                  25                  30

Asn Ser Ser Phe Thr Gly Cys Ser Ser Leu Gly Tyr Ser Ser Ser Arg
            35                  40                  45

Asn Arg Ser Phe Ser Lys Ala Ser Gly Pro Thr Gln Tyr Ile Phe His
        50                  55                  60

Glu Glu Asp Met Asn Phe Val Asp Ala Pro Thr Ile Ser Arg Val Phe
65                  70                  75                  80

Asp Glu Lys Thr Met Tyr Arg Asn Phe Ser Ser Pro Arg Gly Met Cys
                85                  90                  95

```
Leu Ile Ile Asn Asn Glu His Phe Glu Gln Met Pro Thr Arg Asn Gly
            100                 105                 110

Thr Lys Ala Asp Lys Asp Asn Leu Thr Asn Leu Phe Arg Cys Met Gly
        115                 120                 125

Tyr Thr Val Ile Cys Lys Asp Asn Leu Thr Gly Arg Gly Met Leu Leu
    130                 135                 140

Thr Ile Arg Asp Phe Ala Lys His Glu Ser His Gly Asp Ser Ala Ile
145                 150                 155                 160

Leu Val Ile Leu Ser His Gly Glu Glu Asn Val Ile Ile Gly Val Asp
                165                 170                 175

Asp Ile Pro Ile Ser Thr His Glu Ile Tyr Asp Leu Leu Asn Ala Ala
            180                 185                 190

Asn Ala Pro Arg Leu Ala Asn Lys Pro Lys Ile Val Phe Val Gln Ala
        195                 200                 205

Cys Arg Xaa Glu Arg Arg Asp Asn Gly Phe Pro Val Leu Asp Ser Val
    210                 215                 220

Asp Gly Val Pro Ala Phe Leu Arg Arg Gly Trp Asp Asn Arg Asp Gly
225                 230                 235                 240

Pro Leu Phe Asn Phe Leu Gly Cys Val Arg Pro Gln Val Xaa Gln Val
                245                 250                 255

Trp Arg Lys Lys Pro Ser Xaa Ala Asp Ile Leu Ile Arg Tyr Ala Thr
            260                 265                 270

Thr Ala Gln Tyr Val Ser Xaa Arg Asn Ser Ala Arg Gly Ser Trp Phe
        275                 280                 285

Ile Gln Ala Val Cys Glu Val Phe Ser Thr His Xaa Lys Asp Met Asp
    290                 295                 300

Val Val Glu Leu Leu Thr Glu Val Asn Lys Lys Val Xaa Cys Gly Phe
305                 310                 315                 320

Gln Thr Ser Gln Gly Ser Asn Ile Leu Lys Gln Met Pro Xaa Met Thr
                325                 330                 335

Xaa Arg Leu Leu Lys Lys Phe Tyr Phe Trp Pro Glu Ala Arg Asn Ser
            340                 345                 350

Ala Val (2) INFORMATION FOR SEQ ID NO:21:

(i) SEQUENCE CHARACTERISTICS:
        (A) LENGTH: 131 amino acids
        (B) TYPE: amino acid
        (C) STRANDEDNESS: single
        (D) TOPOLOGY: linear (ii) MOLECULE TYPE: protein (v) FRAGMENT TYPE: C-terminal (xi) SEQUENCE DESCRIPTION: SEQ ID NO:21:

Val Asp Gly Val Pro Ala Phe Leu Arg Arg Gly Trp Asp Asn Arg Asp
1               5                   10                  15

Gly Pro Leu Phe Asn Phe Leu Gly Cys Val Arg Pro Gln Val Xaa Gln
            20                  25                  30

Val Trp Arg Lys Lys Pro Ser Xaa Ala Asp Ile Leu Ile Arg Tyr Ala
        35                  40                  45

Thr Thr Ala Gln Tyr Val Ser Xaa Arg Asn Ser Ala Arg Gly Ser Trp
    50                  55                  60

Phe Ile Gln Ala Val Cys Glu Val Phe Ser Thr His Xaa Lys Asp Met
65                  70                  75                  80
```

```
Asp Val Val Glu Leu Leu Thr Glu Val Asn Lys Lys Val Xaa Cys Gly
                85                  90                  95

Phe Gln Thr Ser Gln Gly Ser Asn Ile Leu Lys Gln Met Pro Xaa Met
            100                 105                 110

Thr Xaa Arg Leu Leu Lys Lys Phe Tyr Phe Trp Pro Glu Ala Arg Asn
        115                 120                 125

Ser Ala Val
    130
```

(2) INFORMATION FOR SEQ ID NO:22:

(i) SEQUENCE CHARACTERISTICS:
        (A) LENGTH: 223 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:22:

```
Arg Ser Arg Ser Arg Ser Arg Ala Leu His Ser Ser Asp Arg His Asn
 1               5                  10                  15

Tyr Ser Ser Pro Pro Val Asn Ala Phe Pro Ser Gln Pro Ser Ser Ala
            20                  25                  30

Asn Ser Ser Phe Thr Gly Cys Ser Ser Leu Gly Tyr Ser Ser Ser Arg
            35                  40                  45

Asn Arg Ser Phe Ser Lys Ala Ser Gly Pro Thr Gln Tyr Ile Phe His
 50                  55                  60

Glu Glu Asp Met Asn Phe Val Asp Ala Pro Thr Ile Ser Arg Val Phe
65                   70                  75                  80

Asp Glu Lys Thr Met Tyr Arg Asn Phe Ser Ser Pro Arg Gly Met Cys
                85                  90                  95

Leu Ile Ile Asn Asn Glu His Phe Glu Gln Met Pro Thr Arg Asn Gly
                100                 105                 110

Thr Lys Ala Asp Lys Asp Asn Leu Thr Asn Leu Phe Arg Cys Met Gly
            115                 120                 125

Tyr Thr Val Ile Cys Lys Asp Asn Leu Thr Gly Arg Gly Met Leu Leu
            130                 135                 140

Thr Ile Arg Asp Phe Ala Lys His Glu Ser His Gly Asp Ser Ala Ile
145                 150                 155                 160

Leu Val Ile Leu Ser His Gly Glu Glu Asn Val Ile Ile Gly Val Asp
                165                 170                 175

Asp Ile Pro Ile Ser Thr His Glu Ile Tyr Asp Leu Leu Asn Ala Ala
            180                 185                 190

Asn Ala Pro Arg Leu Ala Asn Lys Pro Lys Ile Val Phe Val Gln Ala
            195                 200                 205

Cys Arg Xaa Glu Arg Arg Asp Asn Gly Phe Pro Val Leu Asp Ser
            210                 215                 220
```

(2) INFORMATION FOR SEQ ID NO:23:

(i) SEQUENCE CHARACTERISTICS:
        (A) LENGTH: 294 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:23:

```
Phe Pro Ala Pro Gln Ala Val Gln Asp Asn Pro Ala Met Pro Thr Ser
 1               5                  10                  15

Ser Gly Ser Glu Gly Asn Val Lys Leu Cys Ser Leu Glu Glu Ala Gln
            20                  25                  30

Arg Ile Trp Lys Gln Lys Ser Ala Glu Ile Tyr Pro Ile Met Asp Lys
        35                  40                  45

Ser Ser Arg Thr Arg Leu Ala Leu Ile Ile Cys Asn Glu Glu Phe Asp
50                      55                  60

Ser Ile Pro Arg Arg Thr Gly Ala Glu Val Asp Ile Thr Gly Met Thr
65                  70                  75                  80

Met Leu Leu Gln Asn Leu Gly Tyr Ser Val Asp Val Lys Lys Asn Leu
                85                  90                  95

Thr Ala Ser Asp Met Thr Thr Glu Leu Glu Ala Phe Ala His Arg Pro
            100                 105                 110

Glu His Lys Thr Ser Asp Ser Thr Phe Leu Val Phe Met Ser His Gly
        115                 120                 125

Ile Arg Glu Gly Ile Cys Gly Lys Lys His Ser Glu Gln Val Pro Asp
130                     135                 140

Ile Leu Gln Leu Asn Ala Ile Phe Asn Met Leu Asn Thr Lys Asn Cys
145                 150                 155                 160

Pro Ser Leu Lys Asp Lys Pro Lys Val Ile Ile Ile Gln Ala Xaa Arg
                165                 170                 175

Xaa Asp Ser Pro Gly Val Val Trp Phe Lys Asp Ser Val Gly Val Ser
            180                 185                 190

Gly Asn Leu Ser Leu Pro Thr Thr Glu Glu Phe Glu Asp Asp Ala Ile
        195                 200                 205

Lys Lys Ala His Ile Xaa Lys Asp Phe Ile Ala Phe Cys Ser Ser Thr
210                     215                 220

Pro Asp Asn Val Ser Xaa Arg His Pro Thr Met Gly Ser Val Phe Ile
225                 230                 235                 240

Gly Arg Leu Ile Glu His Met Gln Glu Tyr Xaa Cys Ser Cys Asp Val
                245                 250                 255

Glu Glu Ile Phe Arg Lys Val Arg Phe Ser Phe Glu Gln Pro Asp Gly
            260                 265                 270

Arg Ala Gln Met Pro Thr Thr Xaa Arg Val Xaa Leu Thr Arg Cys Phe
        275                 280                 285

Tyr Leu Phe Pro Gly His
    290
```

(2) INFORMATION FOR SEQ ID NO:24:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:24:

```
Ser Val Gly Val Ser Gly Asn Leu Ser Leu Pro Thr Thr Glu Glu Phe
 1               5                  10                  15

Glu Asp Asp Ala Ile Lys Lys Ala His Ile Xaa Lys Asp Phe Ile Ala
```

```
                    20                  25                  30
Phe Cys Ser Ser Thr Pro Asp Asn Val Ser Xaa Arg His Pro Thr Met
                35                  40                  45

Gly Ser Val Phe Ile Gly Arg Leu Ile Glu His Met Gln Glu Tyr Xaa
            50                  55                  60

Cys Ser Cys Asp Val Glu Glu Ile Phe Arg Lys Val Arg Phe Ser Phe
 65                  70                  75                  80

Glu Gln Pro Asp Gly Arg Ala Gln Met Pro Thr Thr Xaa Arg Val Xaa
                85                  90                  95

Leu Thr Arg Cys Phe Tyr Leu Phe Pro Gly His
                100                 105
```

(2) INFORMATION FOR SEQ ID NO:25:

(i) SEQUENCE CHARACTERISTICS:
        (A) LENGTH: 187 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:25:

```
Phe Pro Ala Pro Gln Ala Val Gln Asp Asn Pro Ala Met Pro Thr Ser
 1               5                  10                  15

Ser Gly Ser Glu Gly Asn Val Lys Leu Cys Ser Leu Glu Glu Ala Gln
                20                  25                  30

Arg Ile Trp Lys Gln Lys Ser Ala Glu Ile Tyr Pro Ile Met Asp Lys
                35                  40                  45

Ser Ser Arg Thr Arg Leu Ala Leu Ile Ile Cys Asn Glu Glu Phe Asp
 50                  55                  60

Ser Ile Pro Arg Arg Thr Gly Ala Glu Val Asp Ile Thr Gly Met Thr
 65                  70                  75                  80

Met Leu Leu Gln Asn Leu Gly Tyr Ser Val Asp Val Lys Lys Asn Leu
                85                  90                  95

Thr Ala Ser Asp Met Thr Thr Glu Leu Glu Ala Phe Ala His Arg Pro
                100                 105                 110

Glu His Lys Thr Ser Asp Ser Thr Phe Leu Val Phe Met Ser His Gly
                115                 120                 125

Ile Arg Glu Gly Ile Cys Gly Lys Lys His Ser Glu Gln Val Pro Asp
                130                 135                 140

Ile Leu Gln Leu Asn Ala Ile Phe Asn Met Leu Asn Thr Lys Asn Cys
145                 150                 155                 160

Pro Ser Leu Lys Asp Lys Pro Lys Val Ile Ile Gln Ala Xaa Arg
                165                 170                 175

Xaa Asp Ser Pro Gly Val Val Trp Phe Lys Asp
                180                 185
```

(2) INFORMATION FOR SEQ ID NO:26:

(i) SEQUENCE CHARACTERISTICS:
        (A) LENGTH: 172 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:26:

Met Leu Thr Val Gln Val Tyr Arg Thr Ser Gln Lys Cys Ser Ser Ser
 1               5                  10                  15

Lys His Val Val Glu Val Leu Leu Asp Pro Leu Gly Thr Ser Phe Cys
                20                  25                  30

Ser Leu Leu Pro Pro Leu Leu Leu Tyr Glu Thr Asp Arg Gly Val
            35                  40                  45

Asp Gln Gln Asp Gly Lys Asn His Thr Gln Ser Pro Gly Cys Glu Glu
        50                  55                  60

Ser Asp Ala Gly Lys Glu Glu Leu Met Lys Met Arg Leu Pro Thr Arg
65                  70                  75                  80

Ser Asp Met Ile Cys Gly Tyr Ala Cys Leu Lys Gly Asn Ala Ala Met
                85                  90                  95

Arg Asn Thr Lys Arg Gly Ser Trp Tyr Ile Glu Ala Leu Thr Gln Val
                100                 105                 110

Phe Ser Glu Arg Ala Xaa Cys Asp Met His Val Ala Asp Met Leu Val
            115                 120                 125

Lys Val Asn Ala Leu Ile Lys Glu Arg Glu Gly Tyr Ala Pro Gly Thr
        130                 135                 140

Glu Phe His Arg Cys Lys Glu Met Ser Glu Tyr Cys Ser Thr Leu Cys
145                 150                 155                 160

Gln Gln Leu Tyr Leu Phe Pro Gly Tyr Pro Pro Thr
                165                 170

(2) INFORMATION FOR SEQ ID NO:27:

(i) SEQUENCE CHARACTERISTICS:
        (A) LENGTH: 172 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:27:

Met Leu Thr Val Gln Val Tyr Arg Thr Ser Gln Lys Cys Ser Ser Ser
 1               5                  10                  15

Lys His Val Val Glu Val Leu Leu Asp Pro Leu Gly Thr Ser Phe Cys
                20                  25                  30

Ser Leu Leu Pro Pro Leu Leu Leu Tyr Glu Thr Asp Arg Gly Val
            35                  40                  45

Asp Gln Gln Asp Gly Lys Asn His Thr Gln Ser Pro Gly Cys Glu Glu
        50                  55                  60

Ser Asp Ala Gly Lys Glu Glu Leu Met Lys Met Arg Leu Pro Thr Arg
65                  70                  75                  80

Ser Asp Met Ile Cys Gly Tyr Ala Cys Leu Lys Gly Asn Ala Ala Met
                85                  90                  95

Arg Asn Thr Lys Arg Gly Ser Trp Tyr Ile Glu Ala Leu Thr Gln Val
                100                 105                 110

Phe Ser Glu Arg Val Xaa Cys Asp Met His Val Ala Asp Met Leu Val
            115                 120                 125

Lys Val Asn Ala Leu Ile Lys Glu Arg Glu Gly Tyr Ala Pro Gly Thr
        130                 135                 140

Glu Phe His Arg Cys Lys Glu Met Ser Glu Tyr Cys Ser Thr Leu Cys
145                 150                 155                 160

```
Gln Gln Leu Tyr Leu Phe Pro Gly Tyr Pro Pro Thr
            165                 170
```